US012760309B2

(12) United States Patent
Miodek et al.

(10) Patent No.: US 12,760,309 B2
(45) Date of Patent: Oct. 13, 2026

(54) ANTI-CD3 APTAMERS FOR USE IN CELL TARGETING AND LABELING

(71) Applicant: Ixaka France, Villejuif (FR)

(72) Inventors: Anna Miodek, Gentilly (FR); Frédéric Mourlane, Nice (FR); Cécile Bauche, Paris (FR); Renaud Vaillant, Gentilly (FR)

( * ) Notice: Subject to any disclaimer, the term of this patent is extended or adjusted under 35 U.S.C. 154(b) by 1122 days.

(21) Appl. No.: 17/629,943

(22) PCT Filed: Jul. 27, 2020

(86) PCT No.: PCT/IB2020/000635
§ 371 (c)(1),
(2) Date: Jan. 25, 2022

(87) PCT Pub. No.: WO2021/019301
PCT Pub. Date: Feb. 4, 2021

(65) Prior Publication Data

US 2022/0251562 A1 Aug. 11, 2022

Related U.S. Application Data

(60) Provisional application No. 62/879,401, filed on Jul. 26, 2019, provisional application No. 62/879,413, filed on Jul. 26, 2019.

(30) Foreign Application Priority Data

Jul. 26, 2019 (WO) .................. PCT/IB2019/000890

(51) Int. Cl.
*C12N 15/115* (2010.01)
*A61K 31/7088* (2006.01)
*A61P 35/00* (2006.01)

(52) U.S. Cl.
CPC ........ *C12N 15/115* (2013.01); *A61K 31/7088* (2013.01); *A61P 35/00* (2018.01); *C12N 2310/16* (2013.01)

(58) Field of Classification Search
CPC ......................... C12N 15/115; C12N 2310/16; C12N 5/0636; C12N 15/86; C12N 2510/00; C12N 2740/15043; C12N 2320/13; A61K 39/00; C07K 14/7051
See application file for complete search history.

(56) References Cited

U.S. PATENT DOCUMENTS

| | | | | |
|---|---|---|---|---|
| 7,566,701 | B2 * | 7/2009 | Diener ................ | C12N 15/115 435/6.12 |
| 2019/0177716 | A1 | 6/2019 | Mallikaratchy | |

FOREIGN PATENT DOCUMENTS

| | | | |
|---|---|---|---|
| CN | 107129988 | A | 9/2017 |
| WO | 2006033854 | A2 | 3/2006 |

OTHER PUBLICATIONS

Wan et al., "An exploration of aptamer internalization mechanisms and their applications in drug delivery", Expert Opin Drug Deliv. Mar. 2019; 16(3):207-218.
Vorobyeva et al., "Aptamers Against Immunologic Targets: Diagnostic and Therapeutic Prospects", Nucleic Acid Therapeutics, vol. 26, No. 1, 2016, pp. 52-65.
Nozari et al., "Aptamers for CD Antigens: From Cell Profiling to Activity Modulation", Molecular Therapy. Nucleic Acids, 2017, vol. 6, pp. 29-44.
Zumrut et al., "Integrating Ligand-Receptor Interactions and In Vitro Evolution for Streamlined Discovery of Artificial Nucleic Acid Ligands", Molecular Therapy. Nucleic Acids, vol. 17, Sep. 2019, pp. 150-163.
Zumrut et al., "Integrating Ligand-Receptor Interactions and In Vitro Evolution for Streamlined Discovery of Artificial Nucleic Acid Ligands Supplemental Information", Molecular Therapy. Nucleic Acids, vol. 17, Sep. 2019, 38 pages.

* cited by examiner

*Primary Examiner* — Kimberly Chong
(74) *Attorney, Agent, or Firm* — Adams & Reese LLP

(57) ABSTRACT

High affinity aptamer sequences recognizing CD3 protein complex on cell surfaces are provided. The aptamers can be used as targeting moieties for delivery vehicles or as molecular components for immunotherapy, immunodiagnostics, or for isolating, purifying, or characterizing CD3+ T cells in a subject.

16 Claims, 61 Drawing Sheets

Specification includes a Sequence Listing.

| Cluster | Sequences | Round 0 | Round 1 | Round 2 | Round 3 | Round 4 | Round 5 | Round 6 |
|---|---|---|---|---|---|---|---|---|
| 1 | CCGGGTGGGGGTTTGGCACCGGGCCTGGCGCAGGGATTCG | 0,000 | 0,000 | 0,000 | 0,000 | 0,001 | 0,165 | 2,826 |
| 2 | GAGGGGTTTGGCATCGGGCCTGGCGCCATTCAAGCTATGC | 0,000 | 0,000 | 0,000 | 0,000 | 0,001 | 0,135 | 2,713 |
| 3 | GCGTAAGGGTTTGGCAGCGGGCCTGGCGGAACGCGTGTAT | 0,000 | 0,000 | 0,000 | 0,000 | 0,001 | 0,078 | 1,626 |
| 4 | GGAGTGGAGTATTCCGGGTTTGGCATCGGGCCTGGCGAAG | 0,000 | 0,000 | 0,000 | 0,000 | 0,001 | 0,065 | 0,915 |
| 5 | CGGCAGGGGTTTGGCTCCGGGTCTGGCGAACTGGCTGAGA | 0,000 | 0,000 | 0,000 | 0,000 | 0,000 | 0,052 | 0,882 |
| 6 | AAGGGATTGGCGTCGGGCCTGGCGTAAGGAGGCTATGCTC | 0,000 | 0,000 | 0,000 | 0,000 | 0,001 | 0,057 | 0,880 |
| 7 | GGGATTGGCGCTGGGCCTGGCAAGGAATCTTCTCGTTGTA | 0,000 | 0,000 | 0,000 | 0,000 | 0,001 | 0,062 | 0,874 |
| 8 | GGGATTGGCTTCGGGCCTGGCGAGTATTGTTTTCCTGGAG | 0,000 | 0,000 | 0,000 | 0,000 | 0,001 | 0,056 | 0,853 |
| 9 | GCATCGAAATGGGGTTGGCACCGGGCCTGGCGAATTGGAT | 0,000 | 0,000 | 0,000 | 0,000 | 0,001 | 0,055 | 0,836 |
| 10 | GAGACTAGAGGGATTGGCTTCGGGCCTGGCGTAC | 0,000 | 0,000 | 0,000 | 0,000 | 0,000 | 0,044 | 0,792 |
| 11 | GATGGAGGGTTTGGCGGTGGGCCTGGCAAGTTATCTCATA | 0,000 | 0,000 | 0,000 | 0,000 | 0,000 | 0,043 | 0,711 |
| 12 | TACGGCTAGGGTTTGGCGTTGGGCCTGGCAGGACCGTAAG | 0,000 | 0,000 | 0,000 | 0,000 | 0,000 | 0,044 | 0,698 |
| 13 | ATATGGGAGGGTGAGGGTTTGGCTGCGGGCCTGGCGGGAG | 0,000 | 0,000 | 0,000 | 0,000 | 0,000 | 0,044 | 0,655 |
| 14 | TGCGGCACATGTACGCGGAGGGATTGGCATAGGGTCTGGC | 0,000 | 0,000 | 0,000 | 0,000 | 0,000 | 0,044 | 0,645 |
| 15 | GGGGTTGGCTTTGGGCCTGGCAGTCATTTGTGAATCCTTA | 0,000 | 0,000 | 0,000 | 0,000 | 0,000 | 0,041 | 0,635 |
| 16 | TCCGACAAAAGGGATTGGCTTCGGGCCTGGCGGGGTTGCC | 0,000 | 0,000 | 0,000 | 0,000 | 0,000 | 0,041 | 0,595 |
| 17 | GGTCGGGGTTTGGCATCGGGACTGGCGTTATACAATCGT | 0,000 | 0,000 | 0,000 | 0,000 | 0,000 | 0,036 | 0,575 |
| 18 | GATGGGGTTTGGCGTCGGGCCTGGCGAATACATCTAAAAG | 0,000 | 0,000 | 0,000 | 0,000 | 0,000 | 0,034 | 0,575 |
| 19 | TACCGCGGGGATTGGCTCCGGGCCTGGCGTCGTAATCTGA | 0,000 | 0,000 | 0,000 | 0,000 | 0,000 | 0,033 | 0,474 |
| 20 | GGTACGGGTTTGGCTACGGGCCTGGCGGGTACCGCGTTAT | 0,000 | 0,000 | 0,000 | 0,000 | 0,000 | 0,025 | 0,449 |
| 21 | GGTCGGGTGCTACTGAGCGATTGGCTTTCCGGACTGGGGA | 0,000 | 0,000 | 0,000 | 0,000 | 0,000 | 0,016 | 0,423 |
| 22 | GGGGTTTGGCTGCGGGCCTGGCGCATGATTCAACGAGACA | 0,000 | 0,000 | 0,000 | 0,000 | 0,000 | 0,026 | 0,345 |
| 23 | CGACCACAGGGGTTTGGCTTCGGGACTGGCGGTGGGCACT | 0,000 | 0,000 | 0,000 | 0,000 | 0,000 | 0,021 | 0,309 |
| 24 | TATGGGTTTGGCATCGGGCCTGGCGGAATGGAAAATGTTA | 0,000 | 0,000 | 0,000 | 0,000 | 0,000 | 0,020 | 0,306 |
| 25 | AGACGGGTTTGGCTGCGGGCCTGGCGGTCGTCATTCCTCT | 0,000 | 0,000 | 0,000 | 0,000 | 0,000 | 0,020 | 0,300 |
| 26 | GAGGGGATTGGCATTTGGGCCTGGCAAATTCATCTATTCT | 0,000 | 0,000 | 0,000 | 0,000 | 0,000 | 0,018 | 0,268 |
| 27 | AGGGGTTTGGCGTCGGGCCTGGCGCAGCTCTTCTTGTGTTT | 0,000 | 0,000 | 0,000 | 0,000 | 0,000 | 0,025 | 0,264 |
| 28 | GGGATTGGCTTCGGGCCTGGCGTATCTTTTACATTACC | 0,000 | 0,000 | 0,000 | 0,000 | 0,000 | 0,021 | 0,258 |
| 29 | GGTGGACGGTATACAGGGGCTGCTCAGGATTGCGGATGAT | 0,000 | 0,000 | 0,000 | 0,000 | 0,000 | 0,017 | 0,253 |
| 30 | CCGTTTGAAGCGTTAGGGTTTGGCATCGGGCCTGGCGCAC | 0,000 | 0,000 | 0,000 | 0,000 | 0,000 | 0,021 | 0,249 |
| 31 | AGGGTTTGGCTACGGGCCTGGCGAGCTGTTTCCGCTACTC | 0,000 | 0,000 | 0,000 | 0,000 | 0,000 | 0,017 | 0,228 |
| 32 | GTGTTATGATACTATGCGTATGGATTGCAAAGGGCTGCTG | 0,000 | 0,000 | 0,000 | 0,000 | 0,000 | 0,012 | 0,218 |
| 33 | GAAGGGTTTGGCATTGGGCCTGGCAAGATAATTTGCAAGT | 0,000 | 0,000 | 0,000 | 0,000 | 0,000 | 0,018 | 0,211 |
| 34 | CGGCGAAGTGGCAGGGTTTGGCTTCGGGTCTGGCGGAACA | 0,000 | 0,000 | 0,000 | 0,000 | 0,000 | 0,015 | 0,192 |
| 35 | GAGGGTTTGGCAGTGGGCCTGGCATCAATTCTTTGTTTTC | 0,000 | 0,000 | 0,000 | 0,000 | 0,000 | 0,016 | 0,178 |
| 36 | TACTGAGGGTTTGGCATTGGGCCTGGCATATTGGTATTT | 0,000 | 0,000 | 0,000 | 0,000 | 0,000 | 0,011 | 0,169 |
| 37 | ATGGGTTTGGCACCGGGTCTGGCGGATTCGATAGGTGGTT | 0,000 | 0,000 | 0,000 | 0,000 | 0,000 | 0,012 | 0,164 |
| 38 | GGGGGTTTGGCTCTGGGCCTGGCATAACGAACCTTCGGAG | 0,000 | 0,000 | 0,000 | 0,000 | 0,000 | 0,014 | 0,163 |
| 39 | TGCCCGAGAGGACTGCTTAGGCTTGCGAGTAGGGAACGCT | 0,000 | 0,000 | 0,000 | 0,000 | 0,000 | 0,012 | 0,156 |
| 40 | AGTGGGATTGGCTTCGGGCCTGGCGTTCGCAACATGTTTA | 0,000 | 0,000 | 0,000 | 0,000 | 0,000 | 0,015 | 0,139 |
| 41 | GGGGATTGGCACTGGGACTGGCACCTTTTTAACATGTATG | 0,000 | 0,000 | 0,000 | 0,000 | 0,000 | 0,013 | 0,138 |
| 42 | GCAATTAAGGGATTGGCTCCGGGCCTGGCGCCACGCATGG | 0,000 | 0,000 | 0,000 | 0,000 | 0,000 | 0,009 | 0,135 |
| 43 | TGGGGTTTGGCAGCGGGTCTGGCGATCATAATGGTGTGCG | 0,000 | 0,000 | 0,000 | 0,000 | 0,000 | 0,014 | 0,134 |
| 44 | ACGGGGGATTGGCTTTGGGCCTGGCAATTAATTTACTGTT | 0,000 | 0,000 | 0,000 | 0,000 | 0,000 | 0,011 | 0,133 |
| 45 | GAGCGCTTGGCAGCCGGTCTGGGGACATCAGAGGTGATGG | 0,000 | 0,000 | 0,000 | 0,000 | 0,000 | 0,008 | 0,121 |

FIG. 1

CELTIC_1s

CELTIC_3

CELTIC_21

```
Cluster21       GGTCGGGTGCTACTGAGCGATTGGCTTTCCGGACTGGGGA---------------  40
Cluster3        ------------GCGTAAGGGTTTGGCAGCGGGCCTGGCGGAACGCGTGTAT---  40
Cluster1        ----------CCGGGTGGGGGTTTGGCACCGGGCCTGGCGCAGGGATTCG-----  40
Cluster2        ---------------GAGGGGTTTGGCATCGGGCCTGGCGCCATTCAAGCTATGC  40
                                  * ** *    * ** **** *

Cluster3        --GCGTAAGGGTTTGGCAGCGGGCCTGGCGGAACGCGTGTAT--- 40
Cluster1        CCGGGTGGGGGTTTGGCACCGGGCCTGGCGCAGGGATTCG----- 40
Cluster2        -----GAGGGGTTTGGCATCGGGCCTGGCGCCATTCAAGCTATGC 40
                       ********** ***********
```

FIG. 6

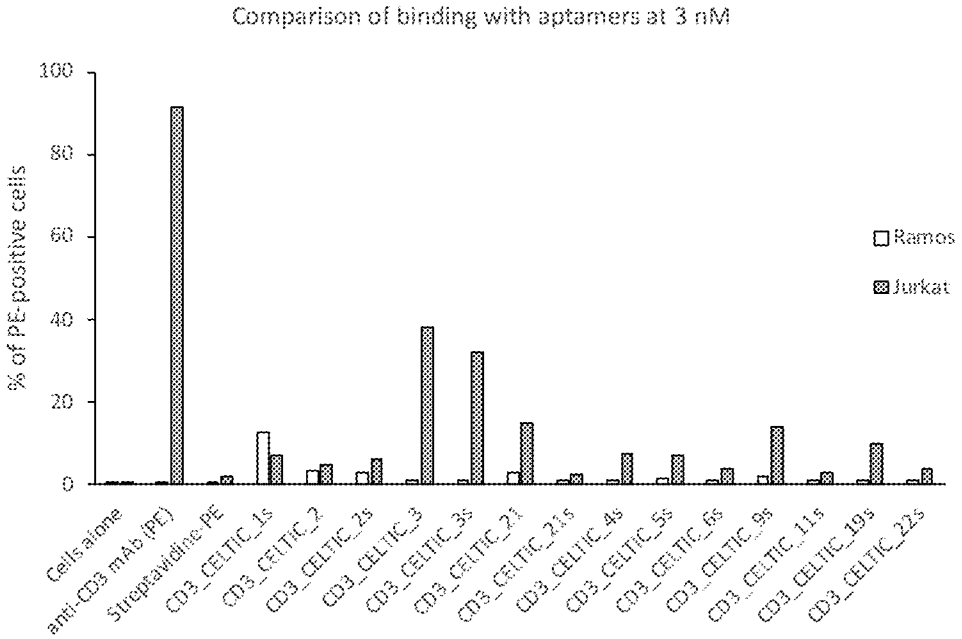
9A
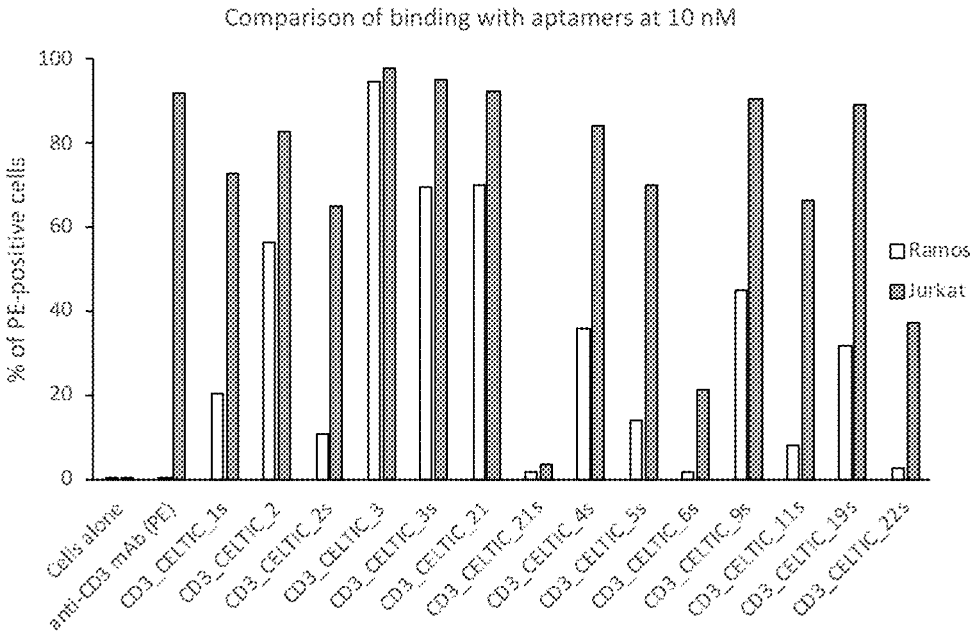
9B
FIGS. 9 A-B

10A
L 24 4 2 1 30 10 0 L 24 4 2 1 30 10 0 L 24 4 2 1 30 10
0
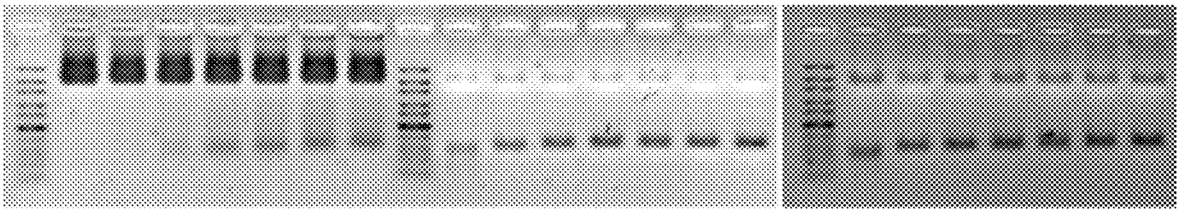
Serum SELEX - 5 % serum RPMI - 10 % serum
10B
L 24 4 2 1 30 10 0 L 24 4 2 1 30 10 0 L 24 4 2 1 30 10
0
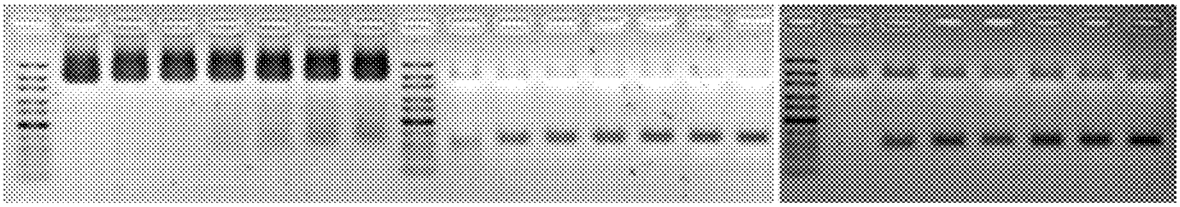
Serum SELEX - 5 % serum RPMI - 10 % serum
10C
L 24 4 2 1 30 10 0 L 24 4 2 1 30 10 0 L 24 4 2 1 30 10
0
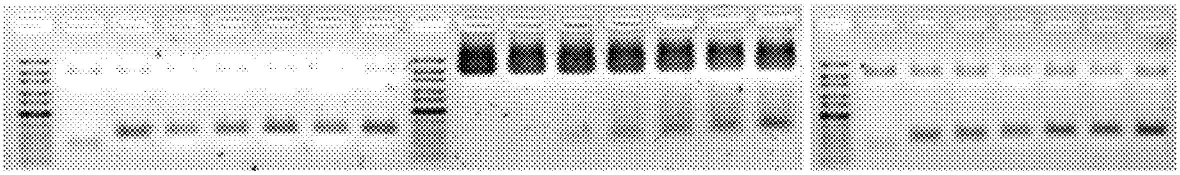
SELEX - 5 % serum Serum RPMI - 10 %
serum
10D
L 24 4 2 1 30 10 0 L 24 4 2 1 30 10 0 L 24 4 2 1 30 10
0
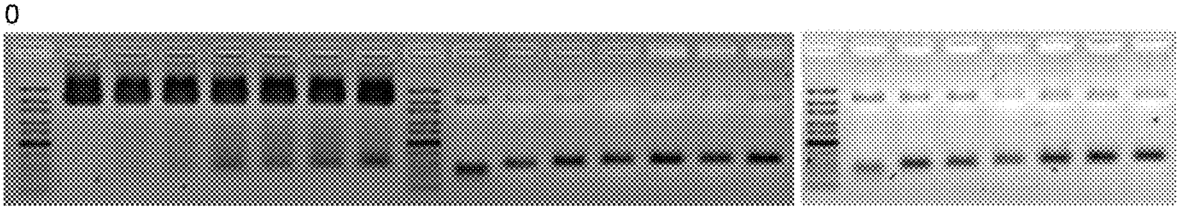
Serum SELEX - 5 % serum RPMI - 10 % serum
FIGS. 10 A-D

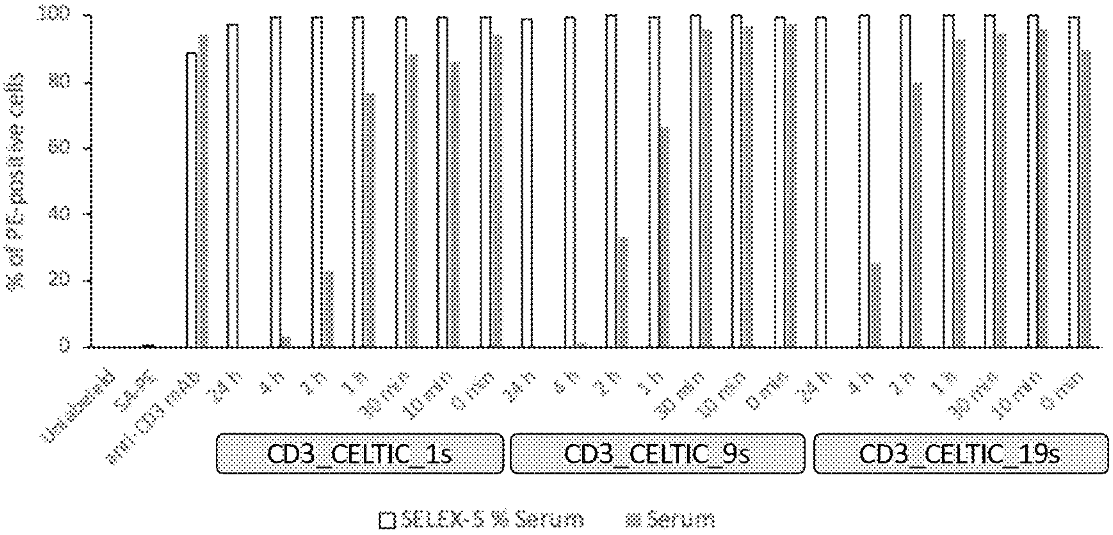
11A
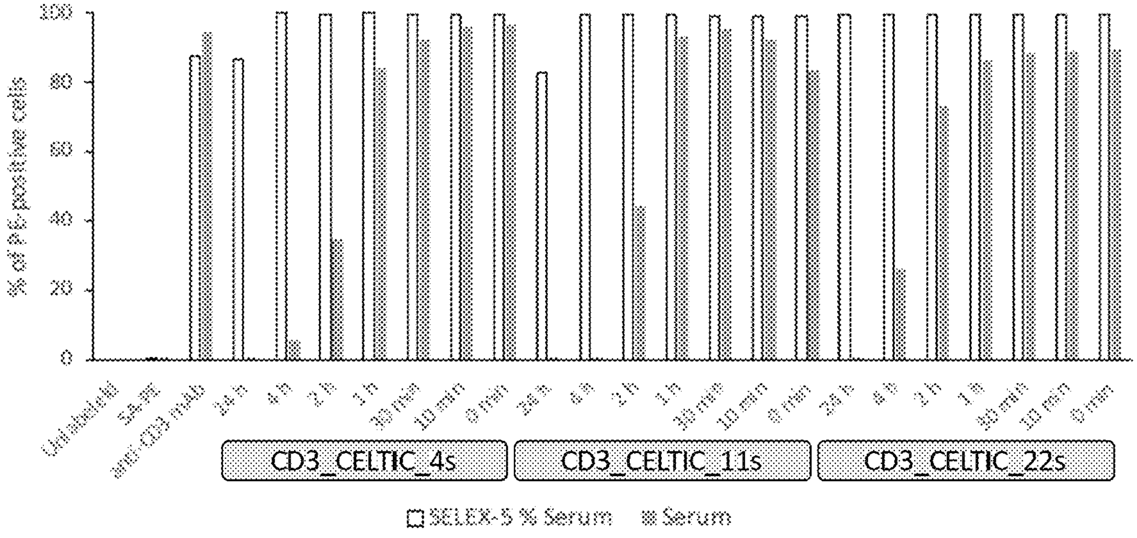
11B
FIGS. 11 A-B

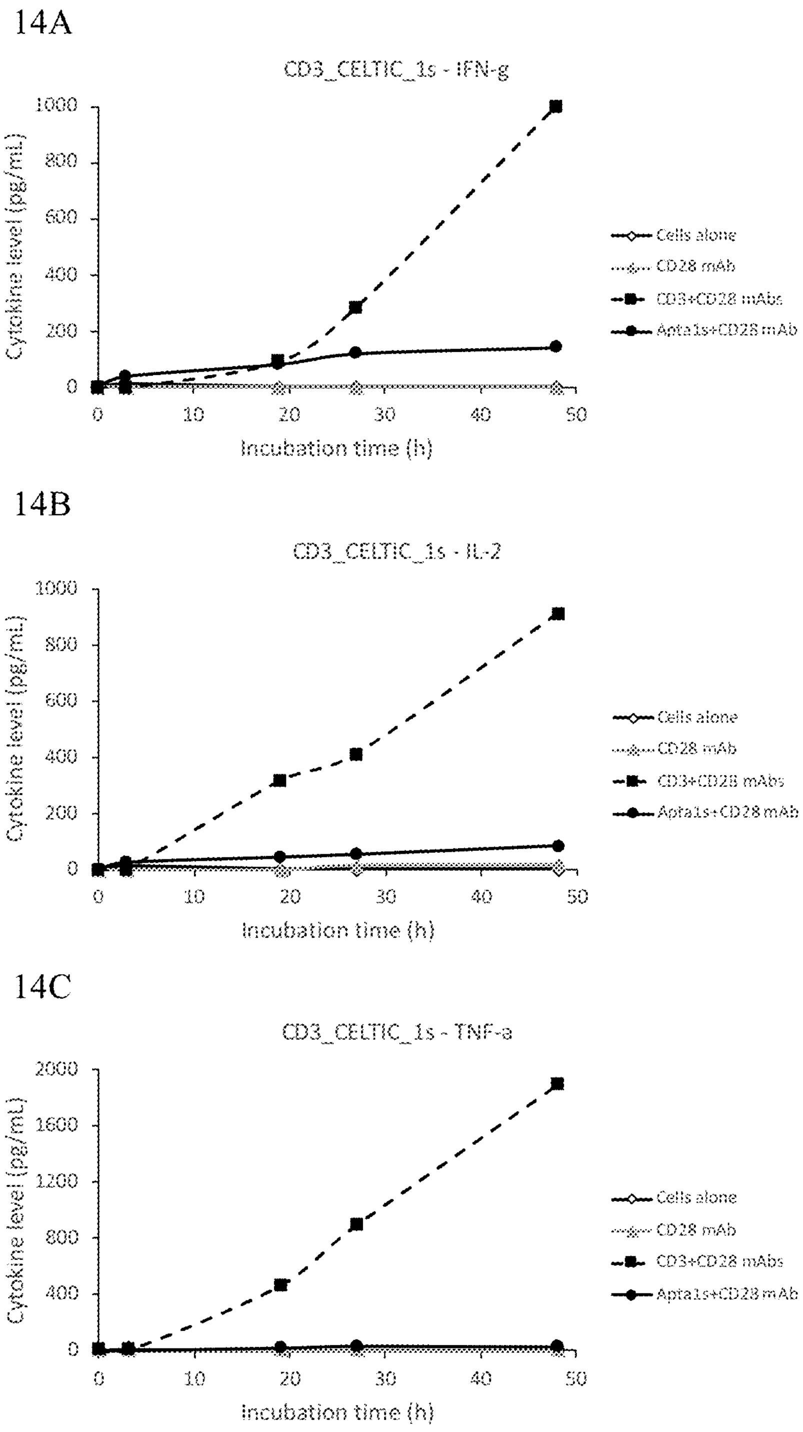
FIGS. 14A-C

14D
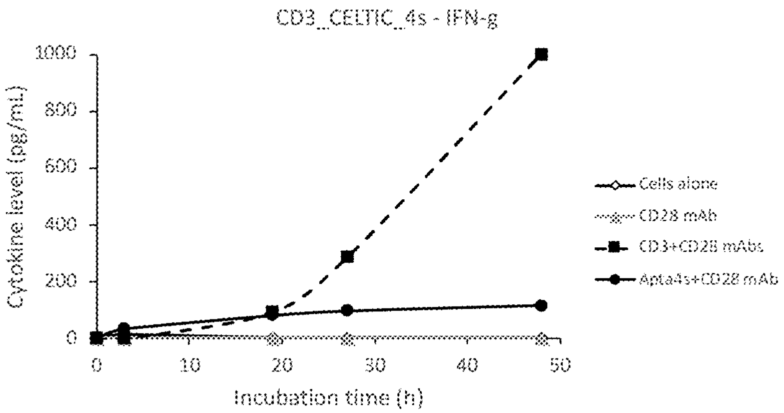
14E
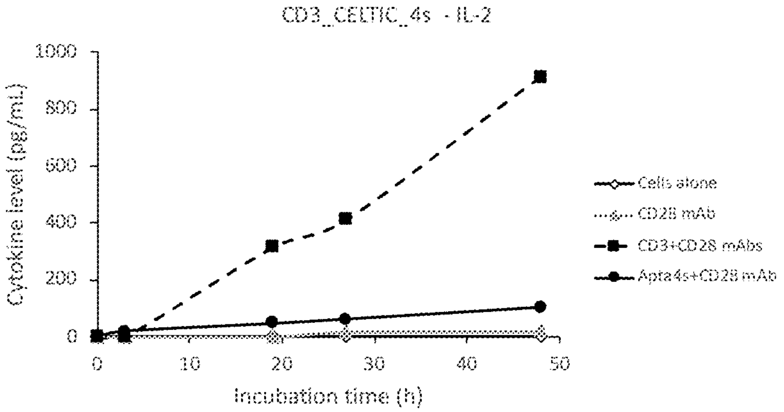
14F
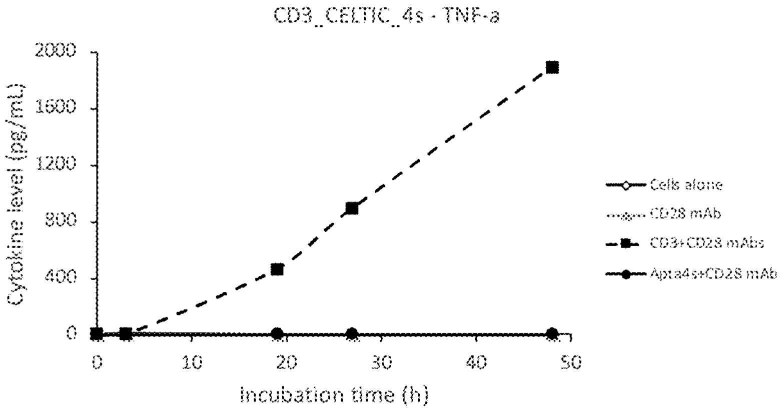
FIGS. 14D-F

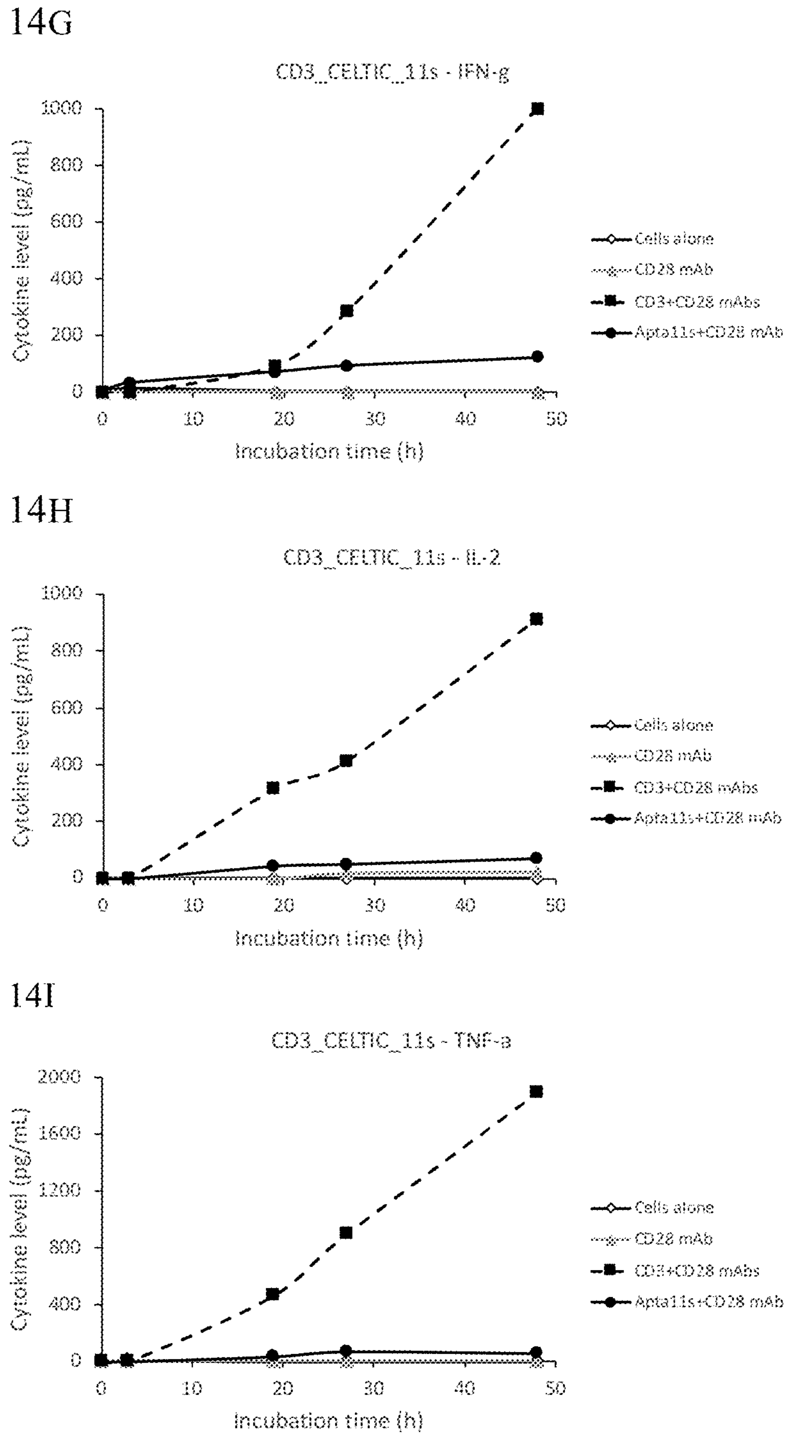
FIGS. 14G-I

14J

14K

14L

15A
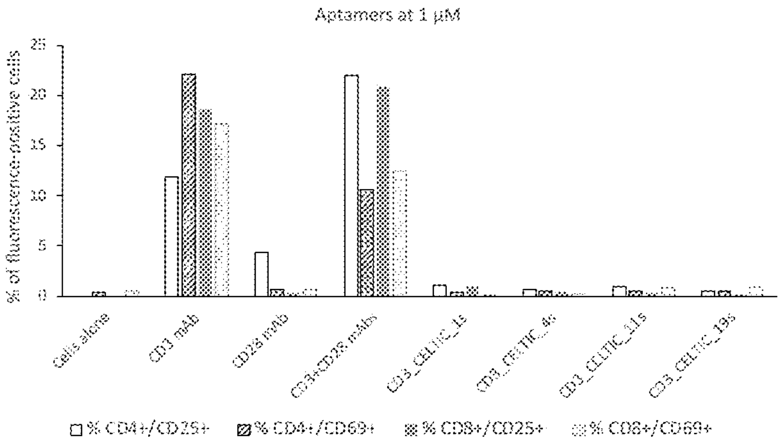
15B
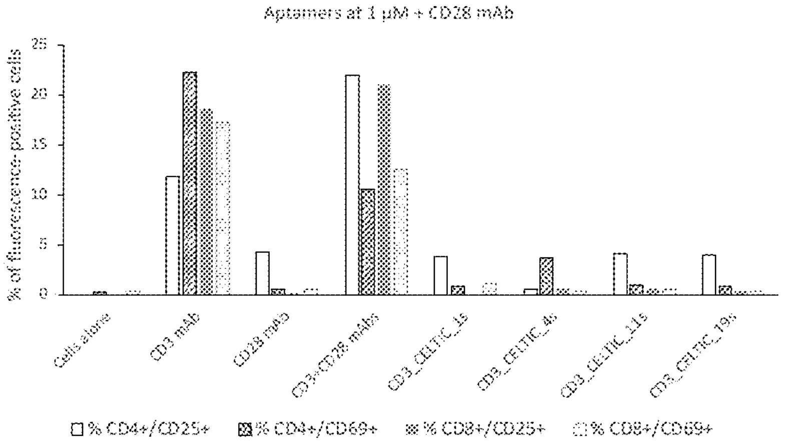
15C
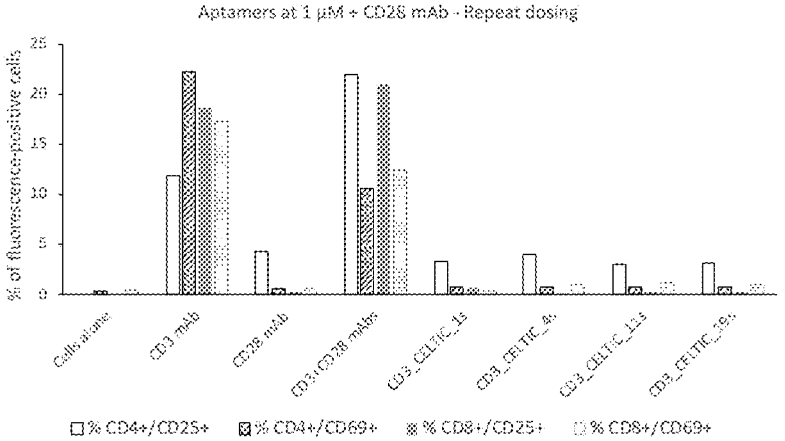
FIGS. 15 A-C

16A
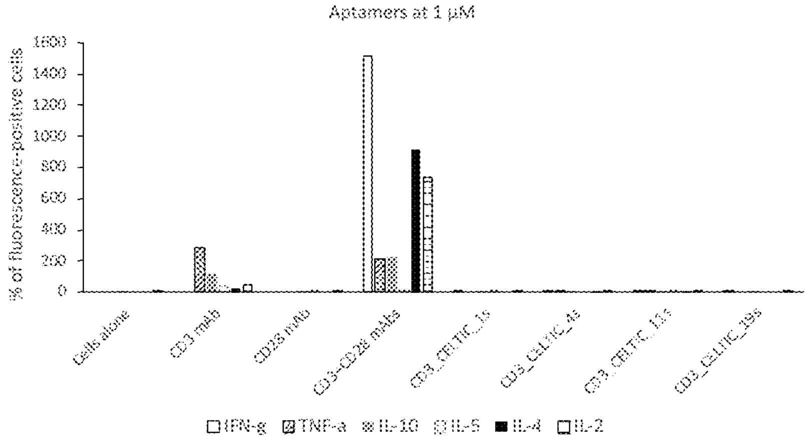
16B
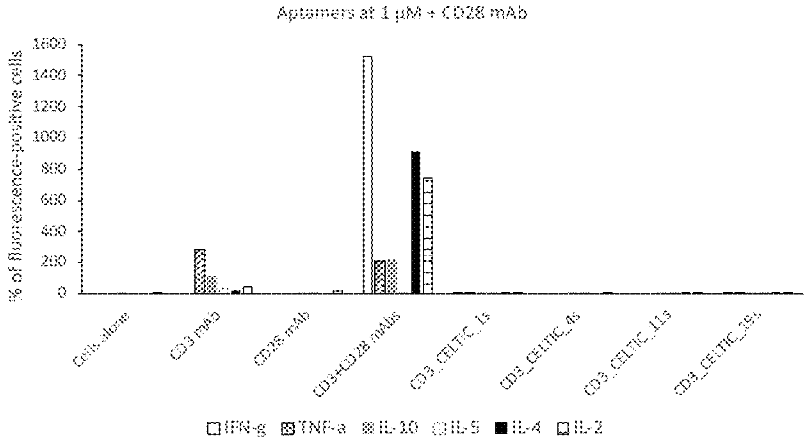
16C
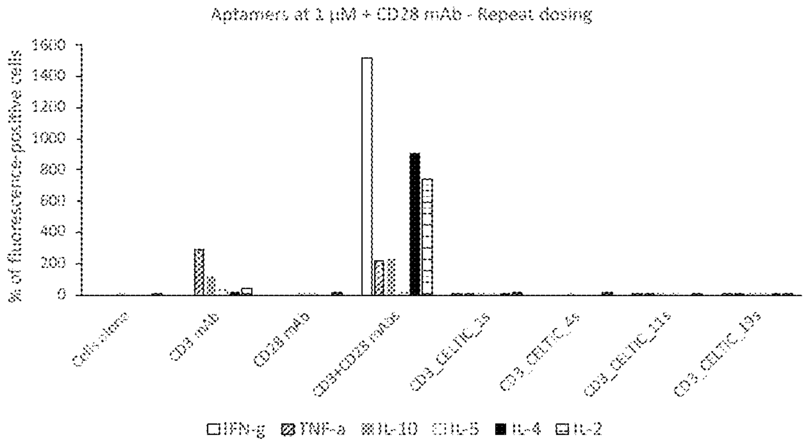
FIGS. 16 A-C 17.1A
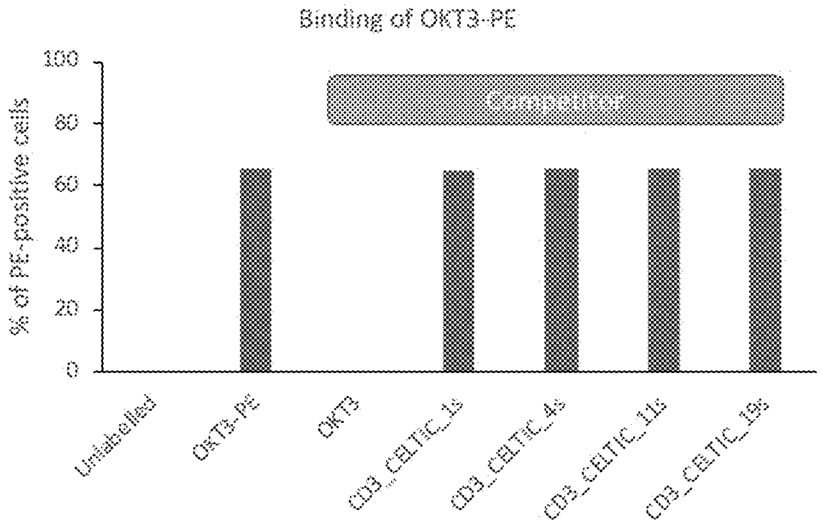
17.1B
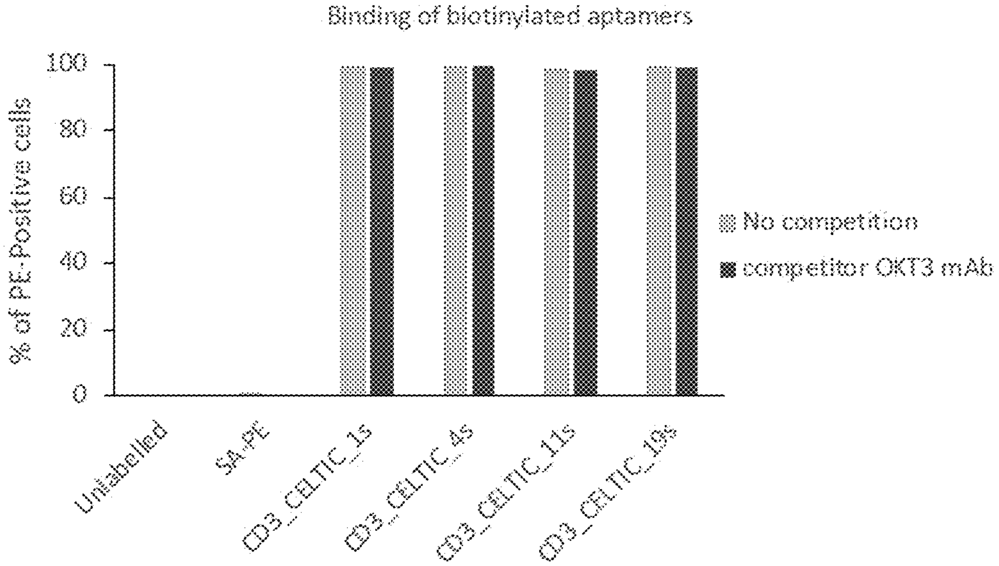
FIGS. 17.1A-B 17.2A
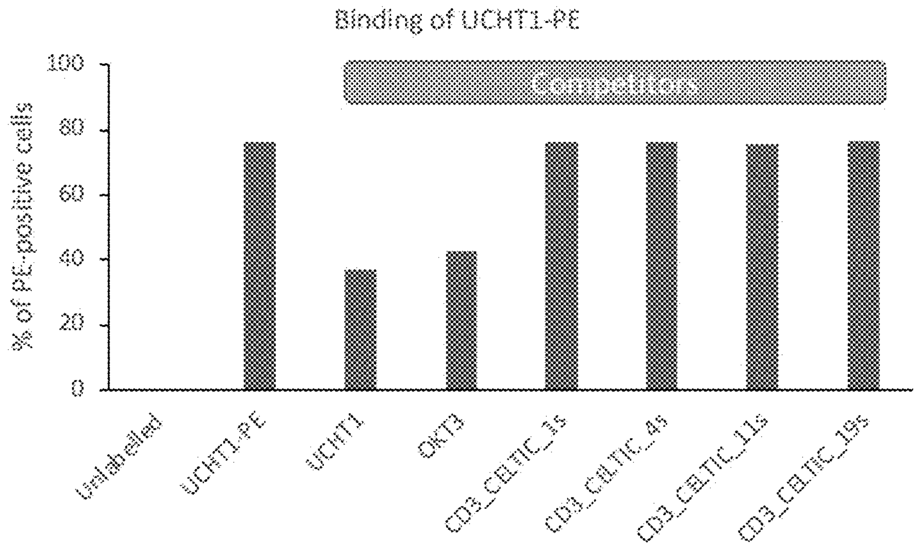
17.2B
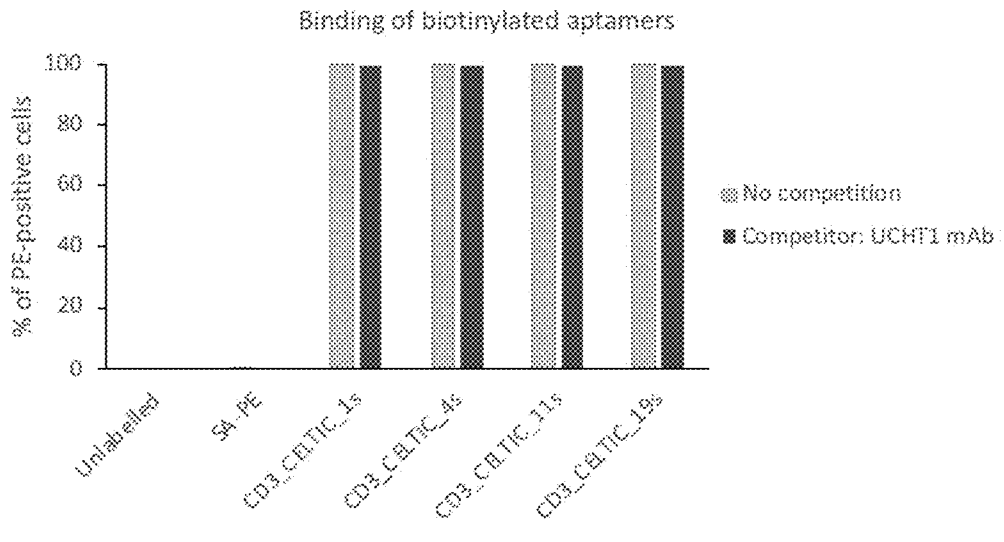
FIGS. 17.2.A-B 17.3A
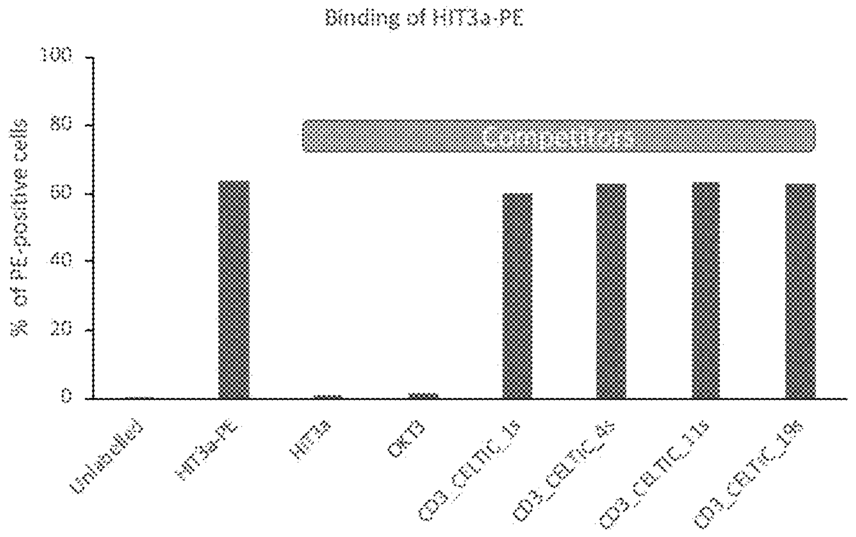
17.3B
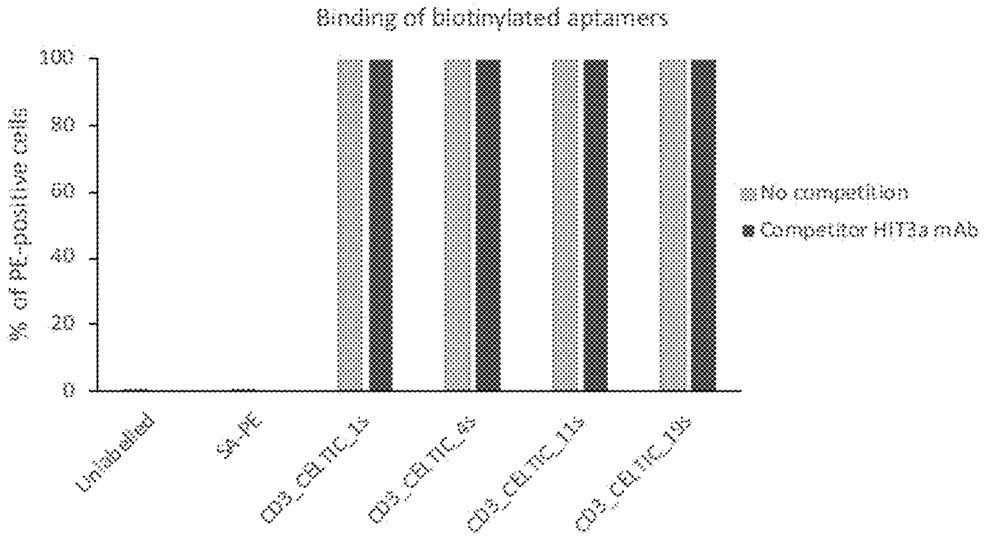
FIGS. 17.3.A-B

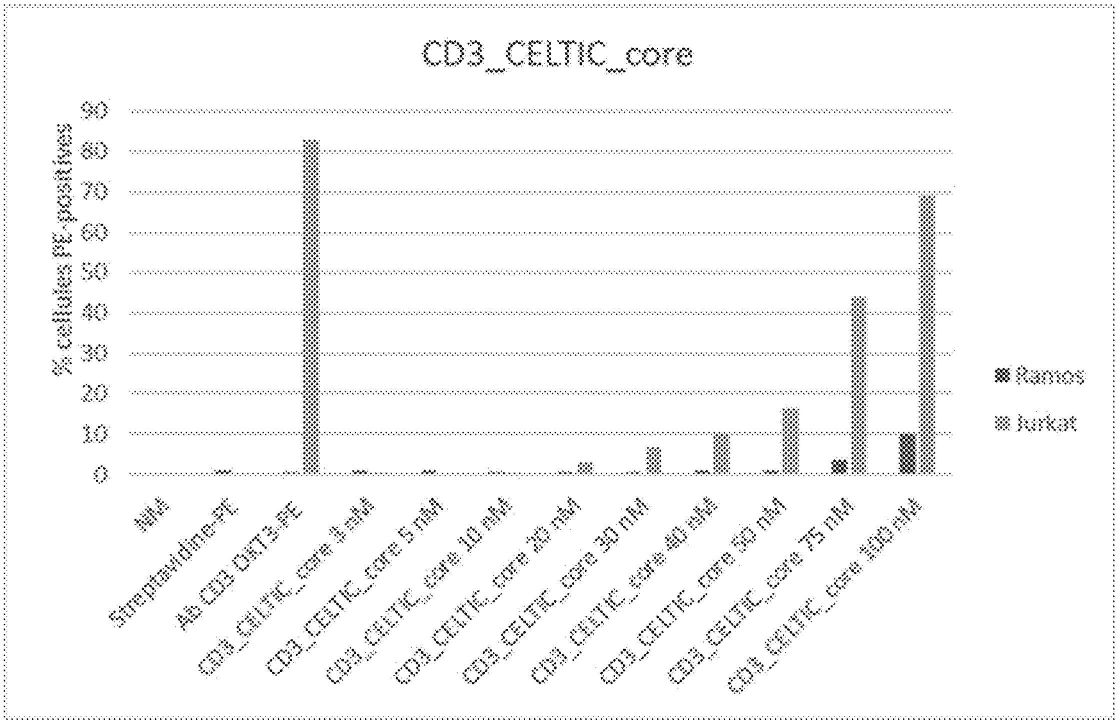
FIG. 17.4

```
          GGGTTTGGCATCGGGCCTGGC
1         GGGTTTGGCACCGGGCCTGGCGC
2         GGGTTTGGCACCGGGCCTGGC
3                   CCGGGCCTGGCC
4         GGGTTTGGCATCGGGCCTGGCG
5         GGGTTTGGCGGTGGGCCTGGC
6      TTTGGGTTTGGCACCGGGCCTGGC
T      TTTGGGTTTGGCATCGGGCCTGGC
7         GGGTTT_GCACCGGGCCTGGC
8         GGGTTTG_CACCGGGCCTGGC
9         GGGTTTGG_ACCGGGCCTGGC
10        GGGTTTGGCACC_GGCCTGGC
11        GGGTTTGGCACCGG_CCTGGC
12        GGGTTTGGCACCGGG_CTGGC
13        GGGTTTGGCACCGGGC_TGGC
```

FIG. 17.5

17.6A
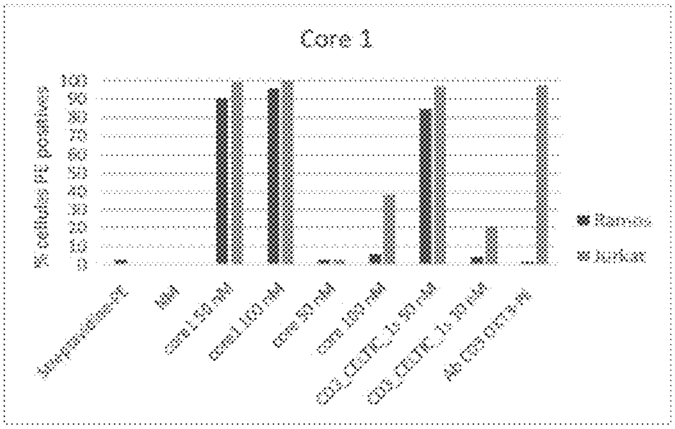
17.6B
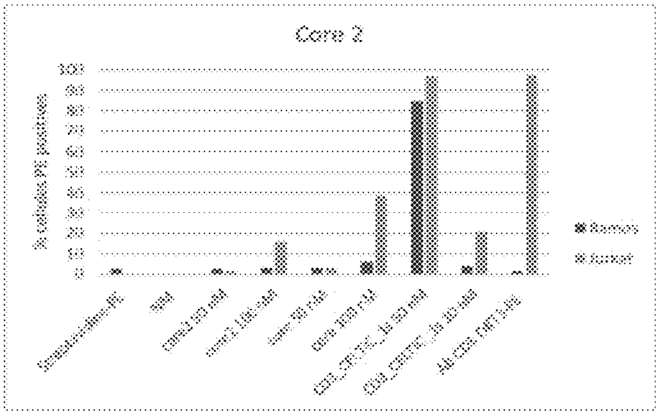
17.6C
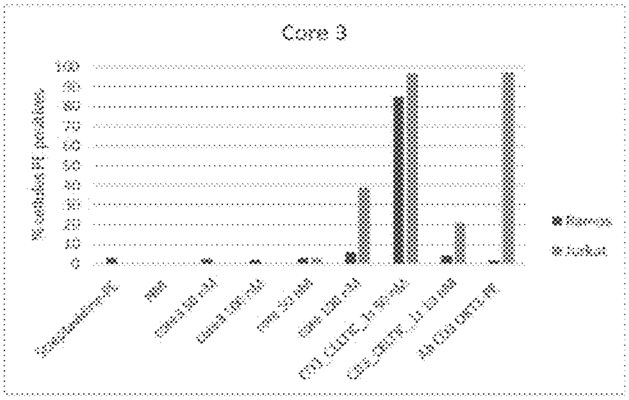
FIGS. 17.6 A-C 17.6D
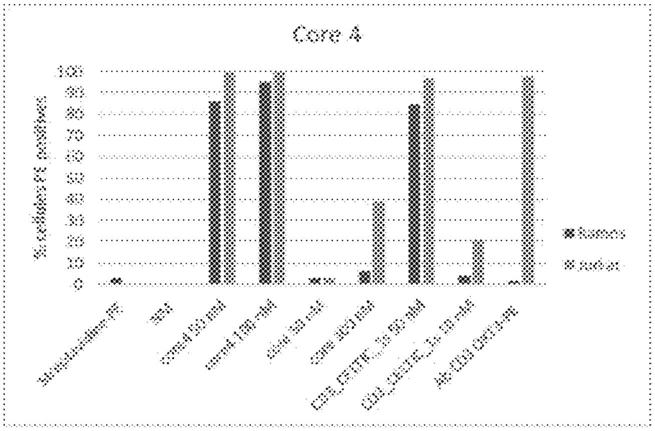
17.6E
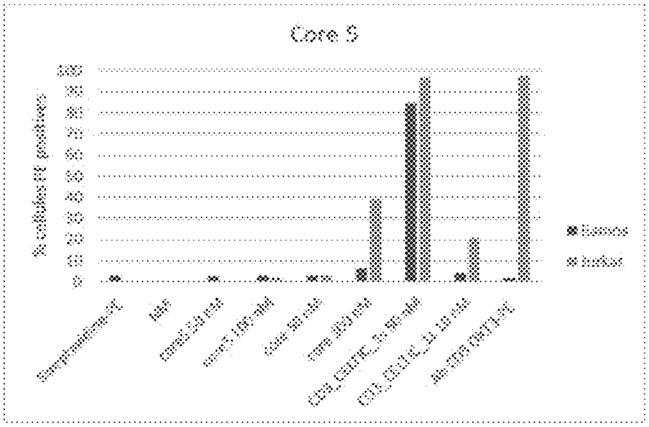
17.6F
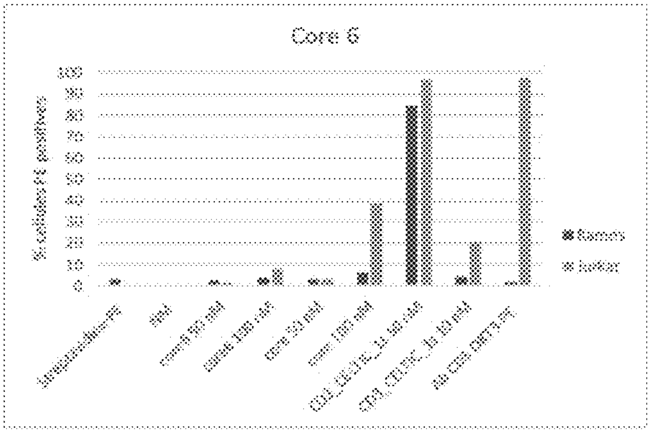
FIGS. 17.6 D-F 17.6G
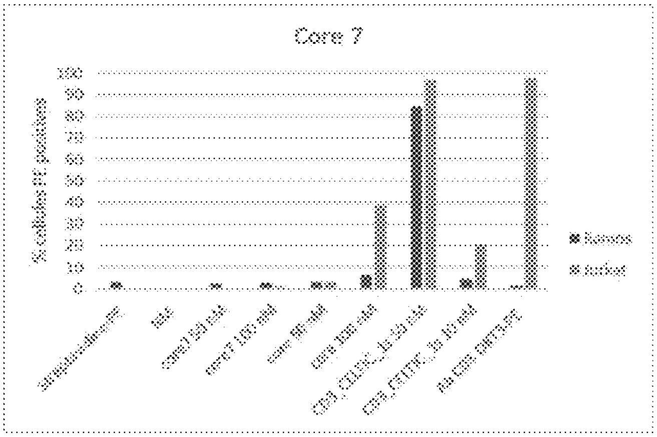
17.6H
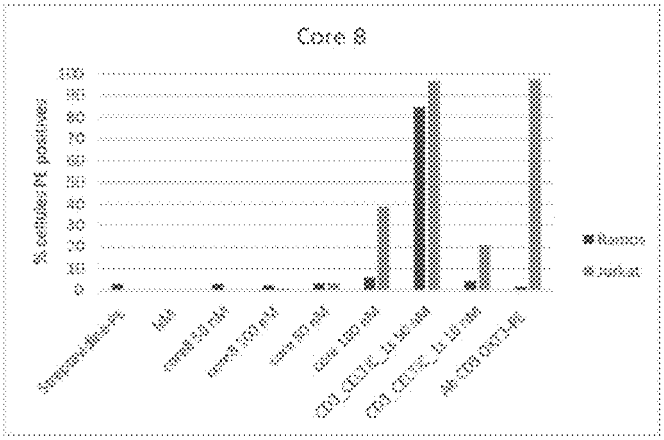
17.6I
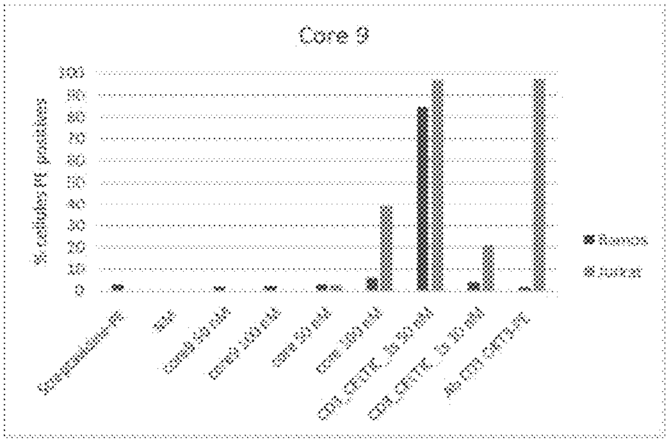
FIGS. 17.6 G-I 17.6J
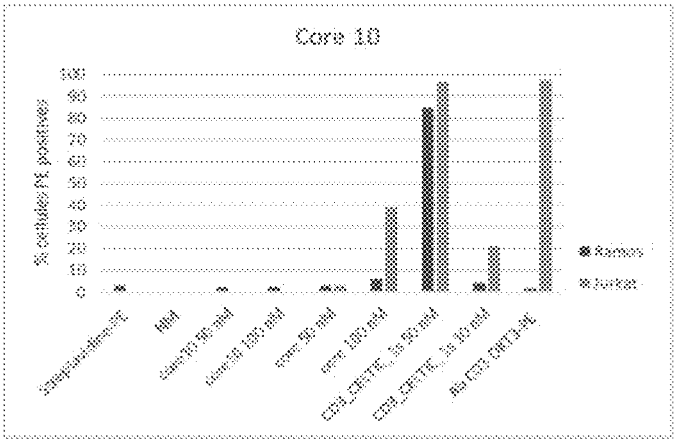
17.6K
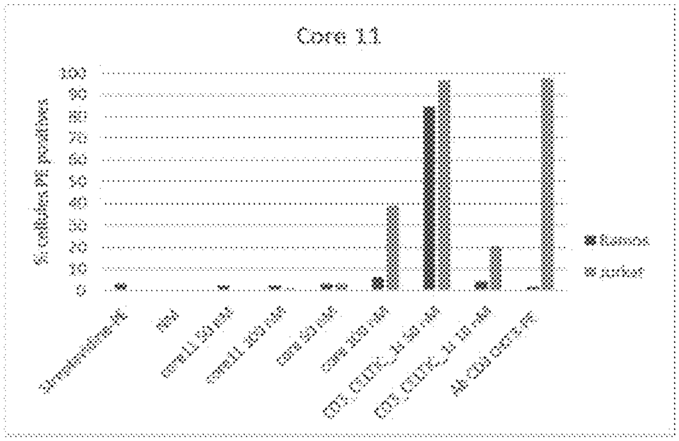
17.6L
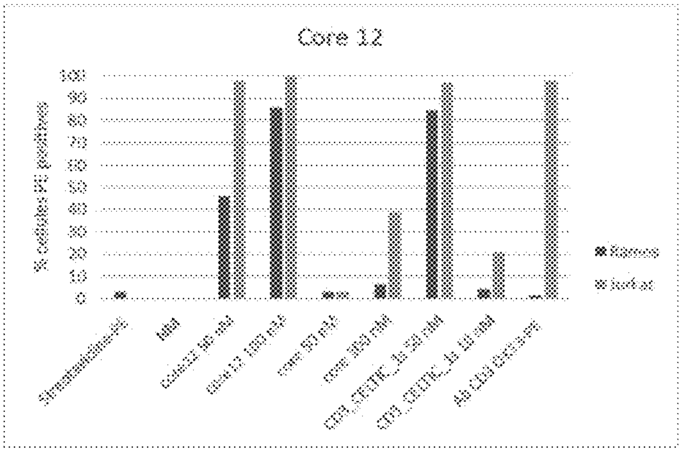
FIGS. 17.6 J-L 17.6M
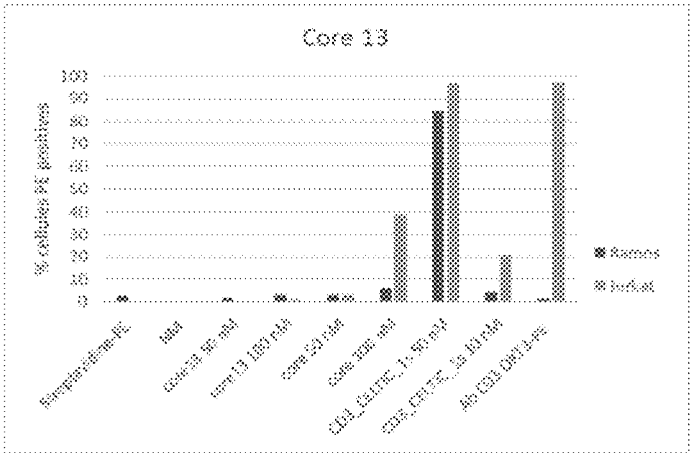
17.6N
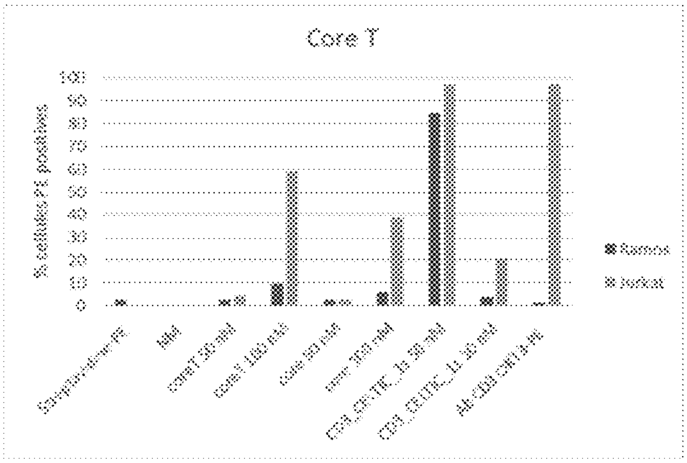
FIGS. 17.6 M-N

```
0       GGGTTTGGCATCGGGCCTGGC
1       GGGTTTGGCACCGGGCCTGGCGC
2       GGGTTTGGCACCGGGCCTGGC
3                 CCGGGCCTGGCC
4       GGGTTTGGCATCGGGCCTGGCG
5       GGGTTTGGCGGTGGGCCTGGC
6    TTTGGGTTTGGCACCGGGCCTGGC
7    TTTGGGTTTGGCATCGGGCCTGGC
7       GGGTTT_GCACCGGGCCTGGC
8       GGGTTTG_CACCGGGCCTGGC
9       GGGTTTGG_ACCGGGCCTGGC
10      GGGTTTGGCACC_GGCCTGGC
11      GGGTTTGGCACCGG_CCTGGC
12      GGGTTTGGCACCGGG_CTGGC
13      GGGTTTGGCACCGGGC_TGGC
14      _GGTTTGGCATCGGGCCTGGC
15      G_GTTTGGCATCGGGCCTGGC
16      GG_TTTGGCATCGGGCCTGGC
17      GGG_TTGGCATCGGGCCTGGC
18      GGGT_TGGCATCGGGCCTGGC
19      GGGTT_GGCATCGGGCCTGGC
20      GGGTTT_GCATCGGGCCTGGC
21      GGGTTTG_CATCGGGCCTGGC
22      GGGTTTGG_ATCGGGCCTGGC
23      GGGTTTGGC_TCGGGCCTGGC
24      GGGTTTGGCA_CGGGCCTGGC
25      GGGTTTGGCAT_GGGCCTGGC
26      GGGTTTGGCATC_GGCCTGGC
27      GGGTTTGGCATCG_GCCTGGC
28      GGGTTTGGCATCGG_CCTGGC
29      GGGTTTGGCATCGGG_CTGGC
30      GGGTTTGGCATCGGGC_TGGC
31      GGGTTTGGCATCGGGCC_GGC
32      GGGTTTGGCATCGGGCCT_GC
33      GGGTTTGGCATCGGGCCTG_C
34      GGGTTTGGCATCGGGCCTGG_
35      GGGTTTGGGATCGGGCCTGGC
36      GGGTTTGGCATCGGGCCTGGG
37      GGGTTTGGGATCGGGCCTGGG
38      GGGTTTGGCATCGGGACTGGC
39      GGGTTTGGCATCGGGGCTGGC
40      GGGTTTGGCATCGGGTCTGGC
41      GGGTTTGGCATCGGGCTGGC
42      GGGTTTGGCA_CGGG_CTGGC
43      GGGTTTGGCAGCGGG_CTGGC
44      GGGTTTGGCAACGGG_CTGGC
```

FIG. 18

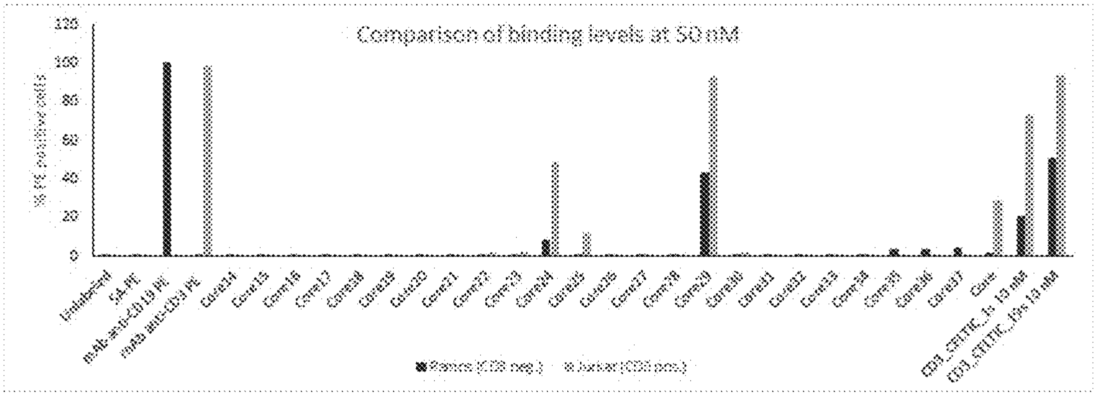
19A
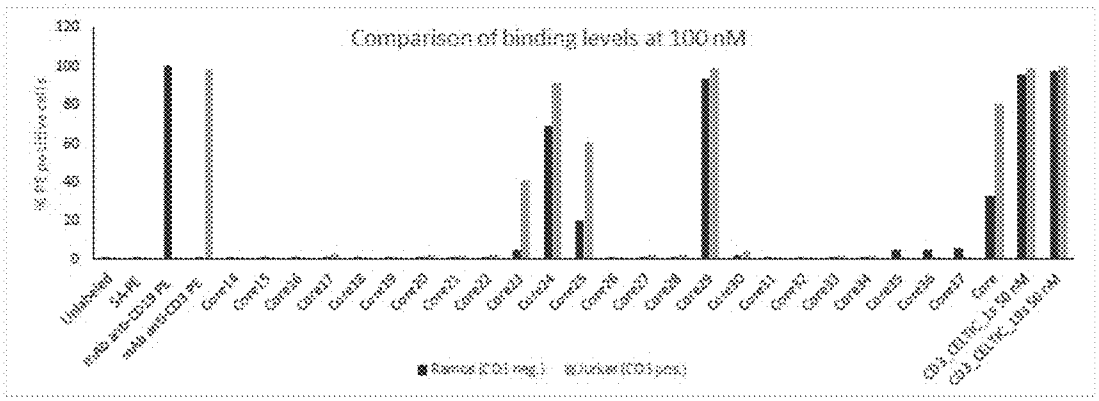
19B
FIGS. 19 A-B

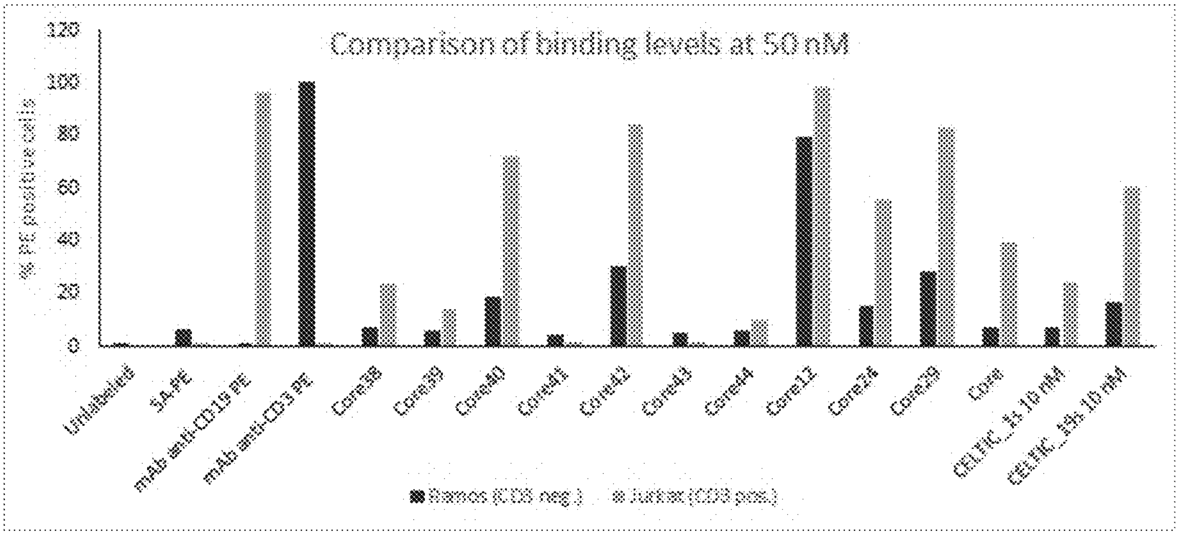
19C
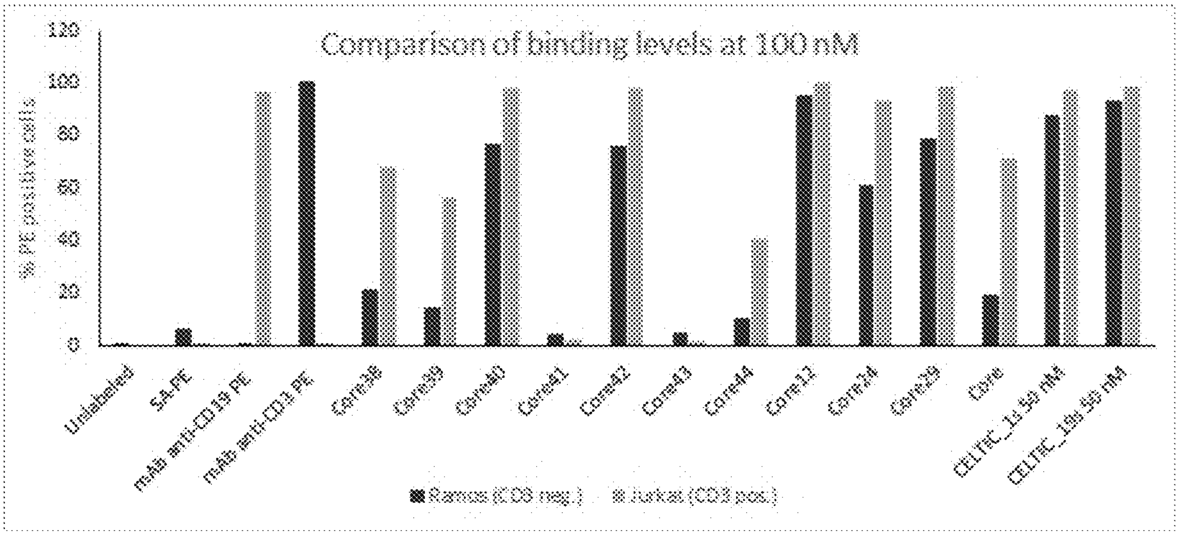
19D
FIGS. 19 C-D

| | | |
|---|---|---|
| c | GGGTTTGGCATCGGGCCTGGC | |
| 1 | GGGTTTGGCACCGGGCCTGGCGC | Binds everywhere |
| 2 | GGGTTTGGCACCGGGCCTGGC | No binding |
| 3 | CCGGGCCTGGCC | No binding |
| 4 | GGGTTTGGCATCGGGCCTGGCG | Binds everywhere |
| 5 | GGGTTTGGCGGTGGGCCTGGC | No binding |
| 6 | TTTGGGTTTGGCACCGGGCCTGGC | No binding |
| T | TTTGGGTTTGGCATCGGGCCTGGC | As good as core |
| 7 | GGGTTT_GCACCGGGCCTGGC | No binding |
| 8 | GGGTTTG_CACCGGGCCTGGC | No binding |
| 9 | GGGTTTGG_ACCGGGCCTGGC | No binding |
| 10 | GGGTTTGGCACC_GGCCTGGC | No binding |
| 11 | GGGTTTGGCACCGG_CCTGGC | No binding |
| 12 | GGGTTTGGCACCGGG_CTGGC | Better than core - less specific |
| 13 | GGGTTTGGCACCGGGC_TGGC | No binding |
| 14 | _GGTTTGGCATCGGGCCTGGC | No binding |
| 15 | G_GTTTGGCATCGGGCCTGGC | No binding |
| 16 | GG_TTTGGCATCGGGCCTGGC | No binding |
| 17 | GGG_TTGGCATCGGGCCTGGC | No binding |
| 18 | GGGT_TGGCATCGGGCCTGGC | No binding |
| 19 | GGGTT_GGCATCGGGCCTGGC | No binding |
| 20 | GGGTTT_GCATCGGGCCTGGC | No binding |
| 21 | GGGTTTG_CATCGGGCCTGGC | No binding |
| 22 | GGGTTTGG_ATCGGGCCTGGC | No binding |
| 23 | GGGTTTGGC_TCGGGCCTGGC | Loss of affinity |
| 24 | GGGTTTGGCA_CGGGCCTGGC | As good as core |
| 25 | GGGTTTGGCAT_GGGCCTGGC | Loss of affinity |
| 26 | GGGTTTGGCATC_GGCCTGGC | No binding |
| 27 | GGGTTTGGCATCG_GCCTGGC | No binding |
| 28 | GGGTTTGGCATCGG_CCTGGC | No binding |
| 29 | GGGTTTGGCATCGGG_CTGGC | Better than core |
| 30 | GGGTTTGGCATCGGGC_TGGC | No binding |
| 31 | GGGTTTGGCATCGGGCC_GGC | No binding |
| 32 | GGGTTTGGCATCGGGCCT_GC | No binding |
| 33 | GGGTTTGGCATCGGGCCTG_C | No binding |
| 34 | GGGTTTGGCATCGGGCCTGG_ | No binding |
| 35 | GGGTTTGGGATCGGGCCTGGC | No binding |
| 36 | GGGTTTGGCATCGGGCCTGGG | No binding |
| 37 | GGGTTTGGGATCGGGCCTGGG | No binding |
| 38 | GGGTTTGGCATCGGGACTGGC | As good as core |
| 39 | GGGTTTGGCATCGGGGCTGGC | Loss of affinity |
| 40 | GGGTTTGGCATCGGGTCTGGC | Better than core |
| 41 | GGGTTTGGCATCGGGCTGGC | No binding |
| 42 | GGGTTTGGCA_CGGG_CTGGC | Better than core |
| 43 | GGGTTTGGCAGCGGG_CTGGC | No binding |
| 44 | GGGTTTGGCAACGGG_CTGGC | Loss of affinity |

FIG. 20

21A
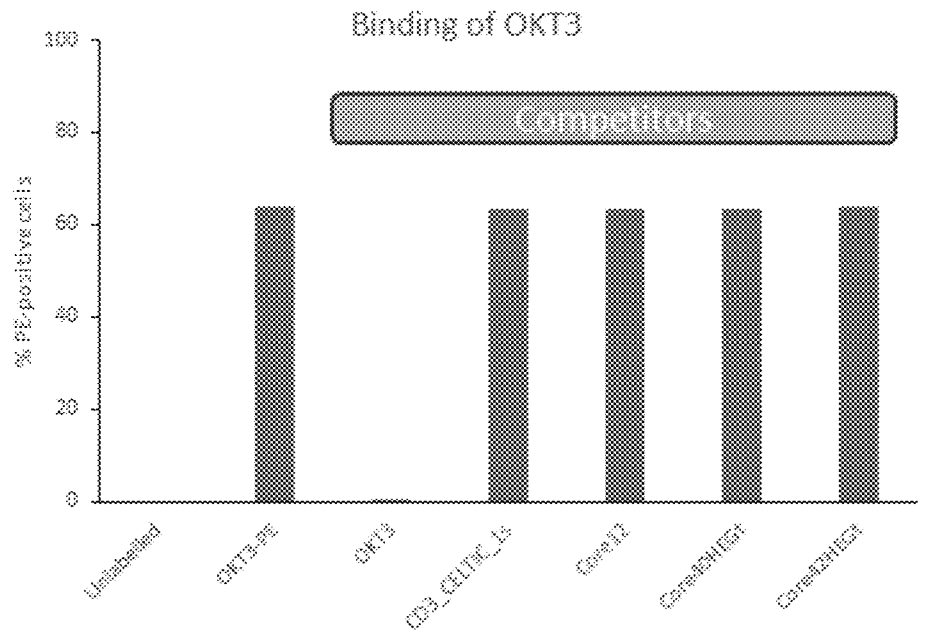
21B
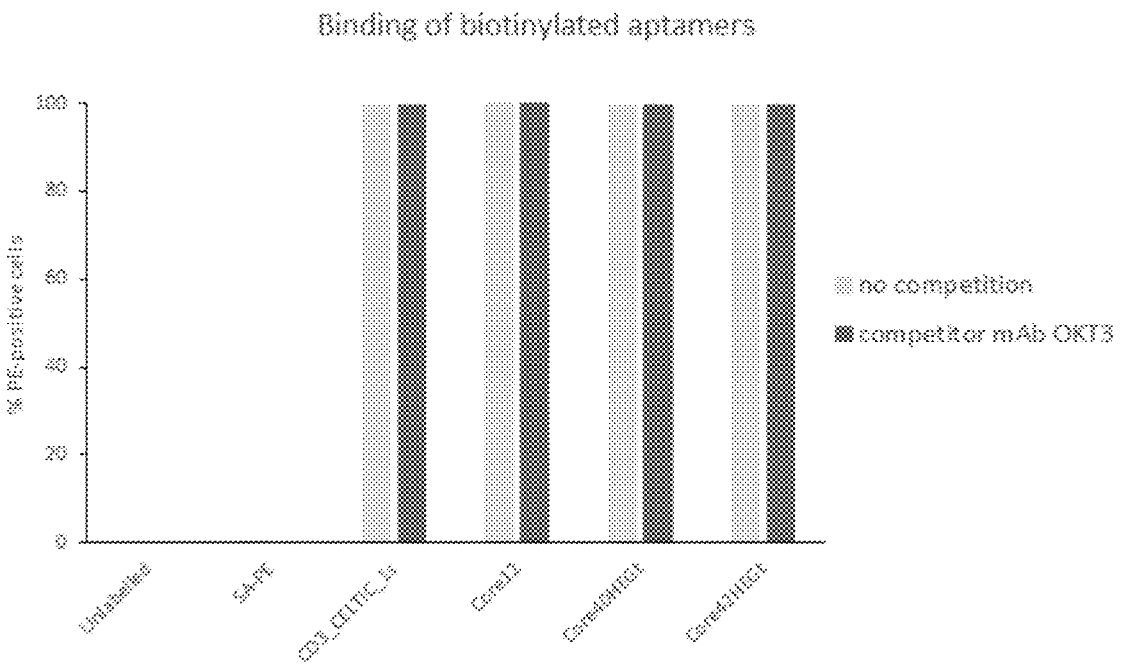
FIGS. 21 A-B

21C
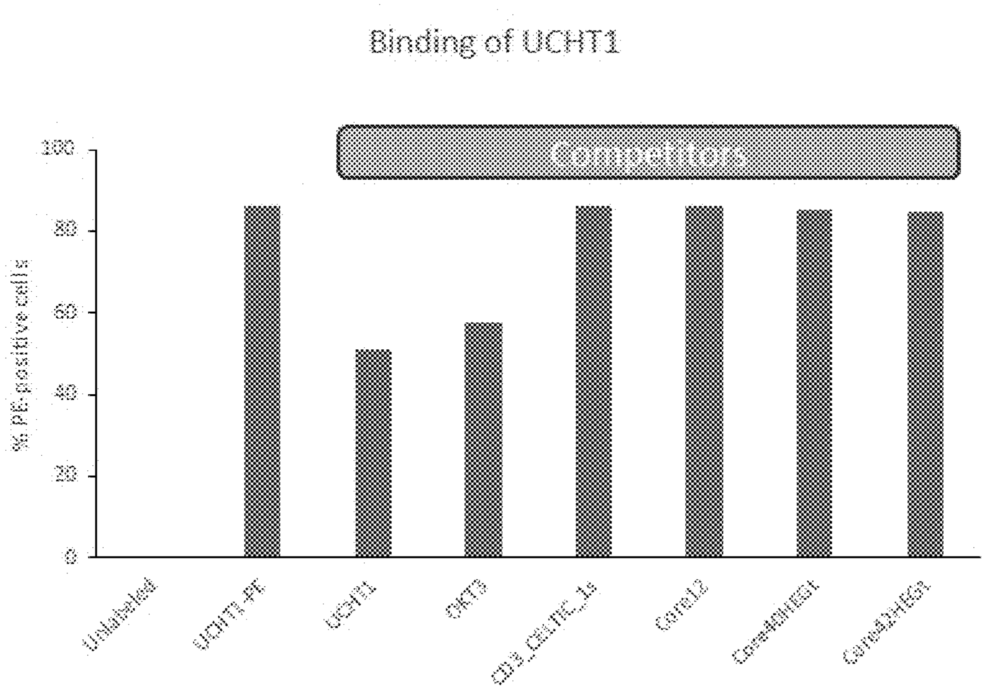
21D
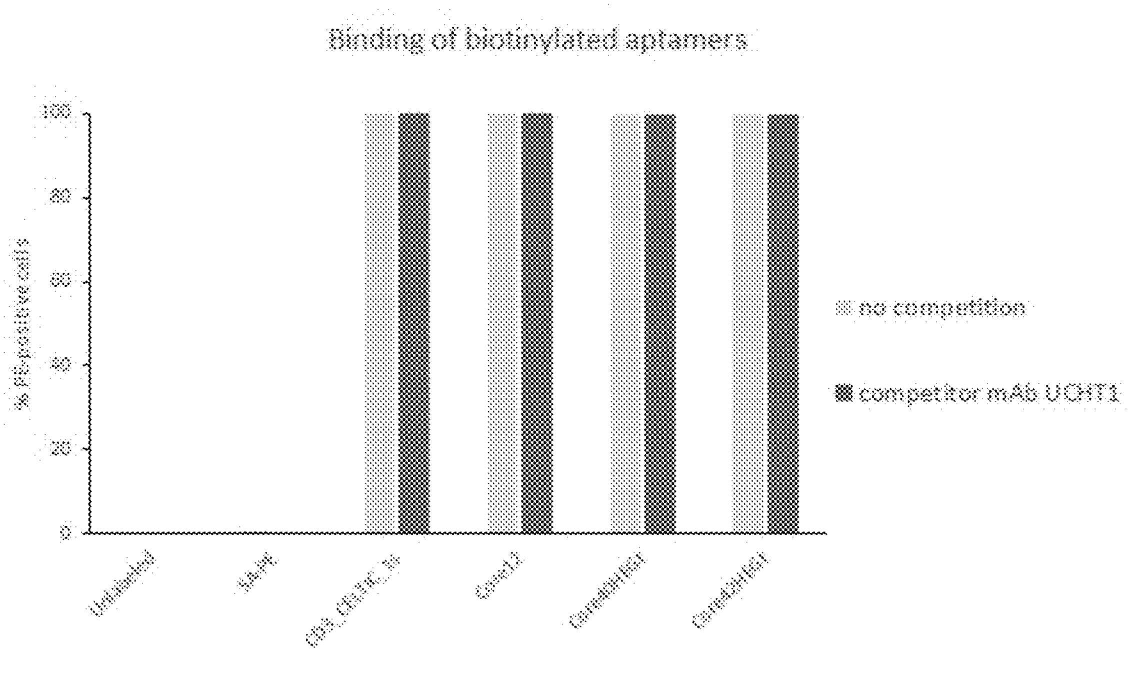
FIGS. 21 C-D

21E
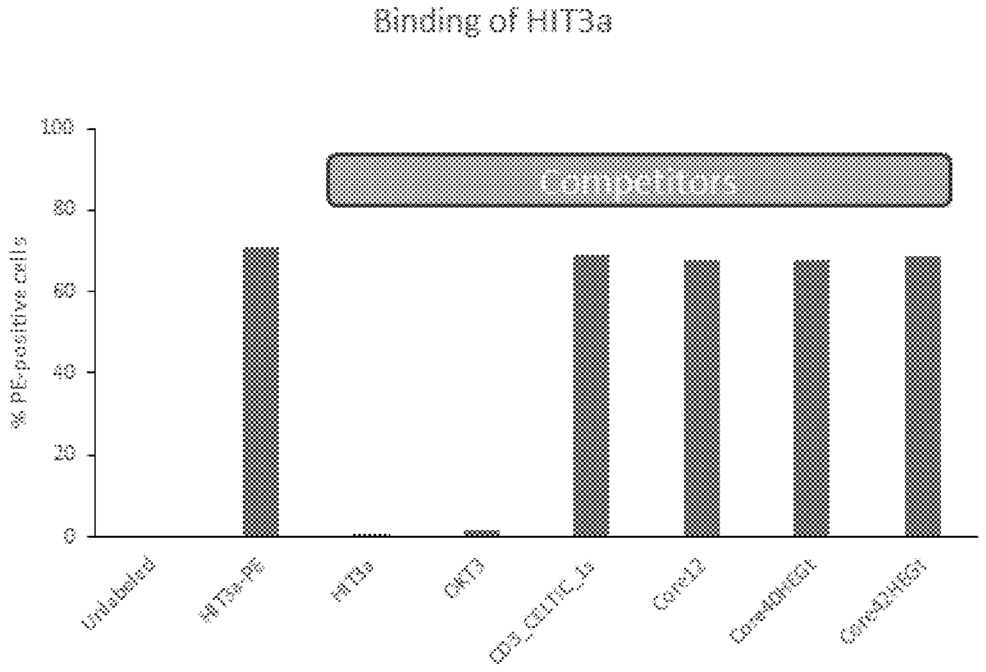
21F
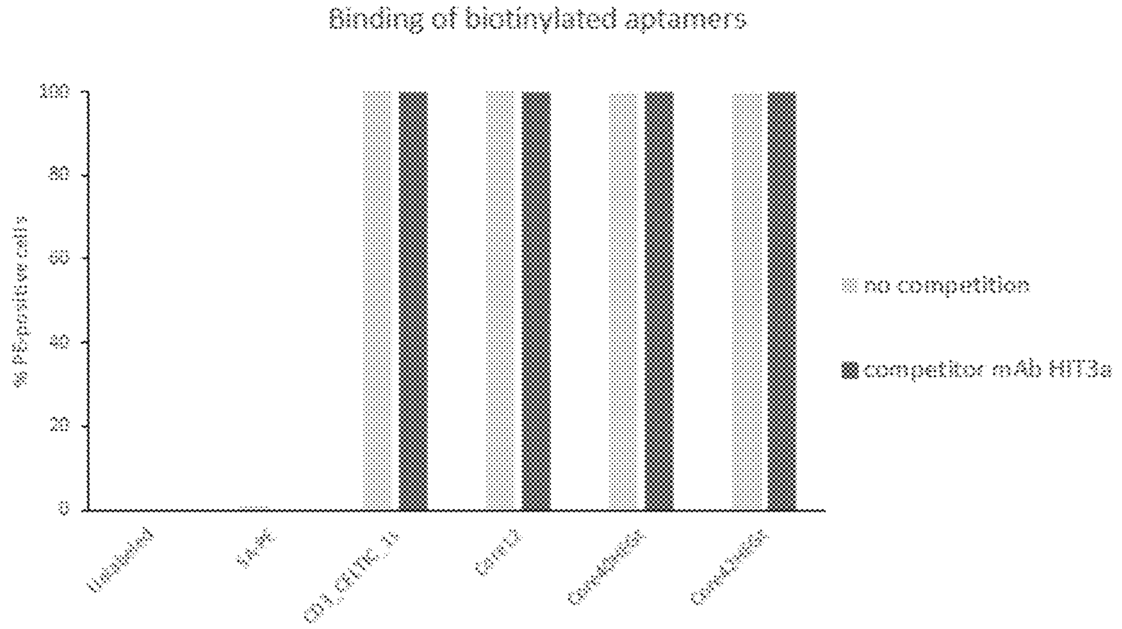
FIGS. 21 E-F

22A
CoreHEG:
L 24 4 2 1 30 10 0 L 24 4 2 1 30 10 0 L 24 4 2 1 30 10 0
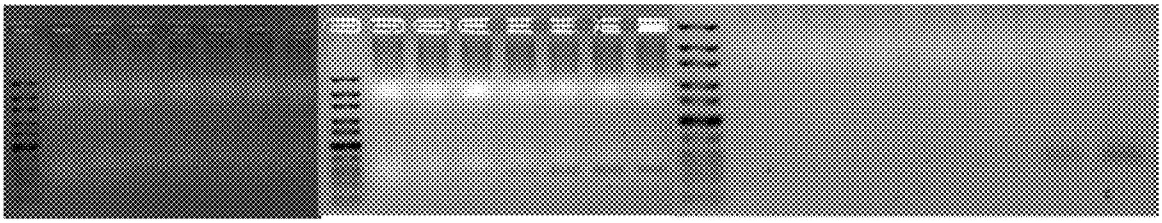
SELEX _ 5 % serum RPMI - 10 % serum serum
22B
Core12:
L 24 4 2 1 30 10 0 L 24 4 2 1 30 10 0 L 24 4 2 1 30 10
0
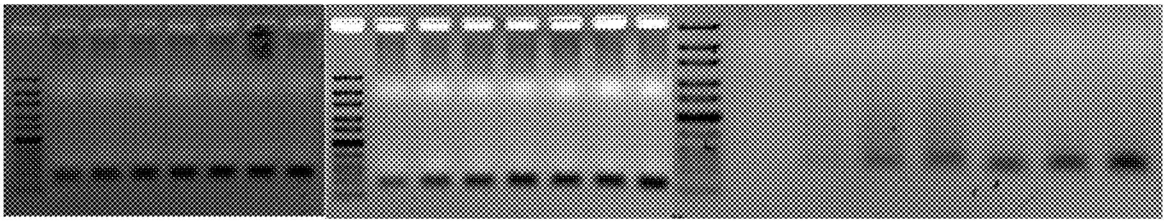
SELEX _ 5 % serum RPMI - 10 % serum serum
22C
Core24HEG:
L 24 4 2 1 30 10 0 L 24 4 2 1 30 10 0 L 24 4 2 1 30 10
0
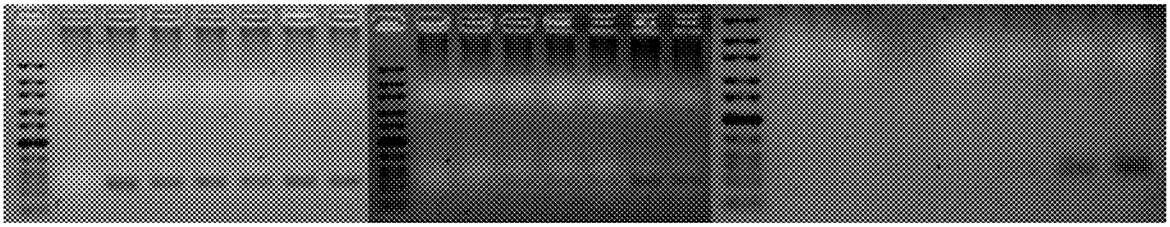
SELEX _ 5 % serum RPMI - 10 % serum serum
FIGS. 22 A-C 22D
Core29HEG:
L 24 4 2 1 30 10 0 L 24 4 2 1 30 10 0 L 24 4 2 1 30 10
0
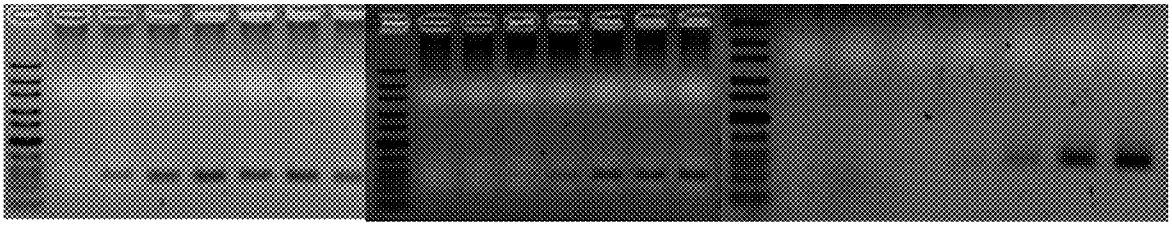
SELEX _ 5 % serum RPMI - 10 % serum serum
22E
Core40HEG:
L 24 4 2 1 30 10 0 L 24 4 2 1 30 10 0 L 24 4 2 1 30 10
0
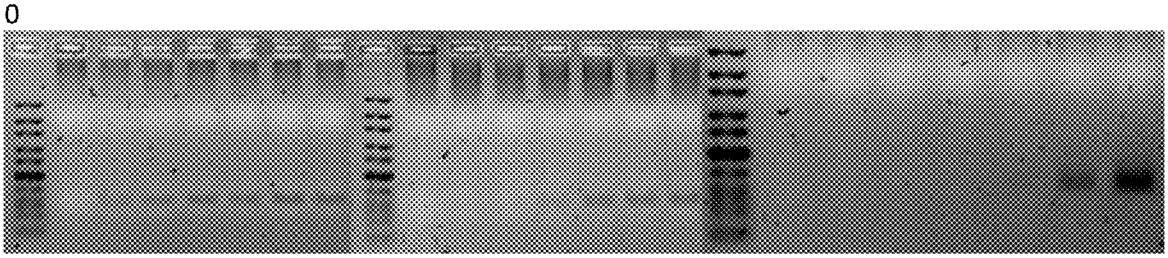
SELEX _ 5 % serum RPMI - 10 % serum serum
22F
Core42HEG:
L 24 4 2 1 30 10 0 L 24 4 2 1 30 10 0 L 24 4 2 1 30 10
0
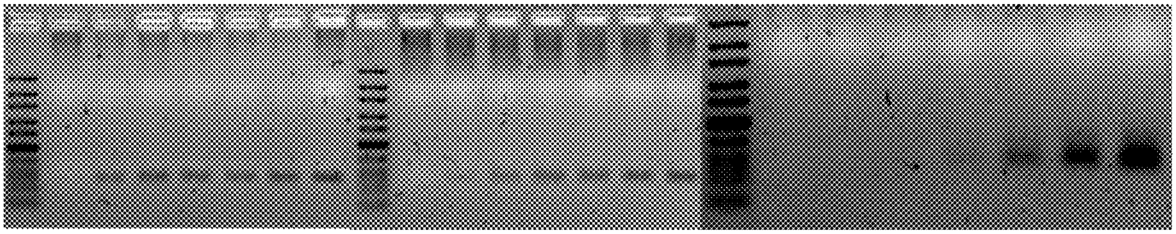
FIGS. 22 D-F 23A
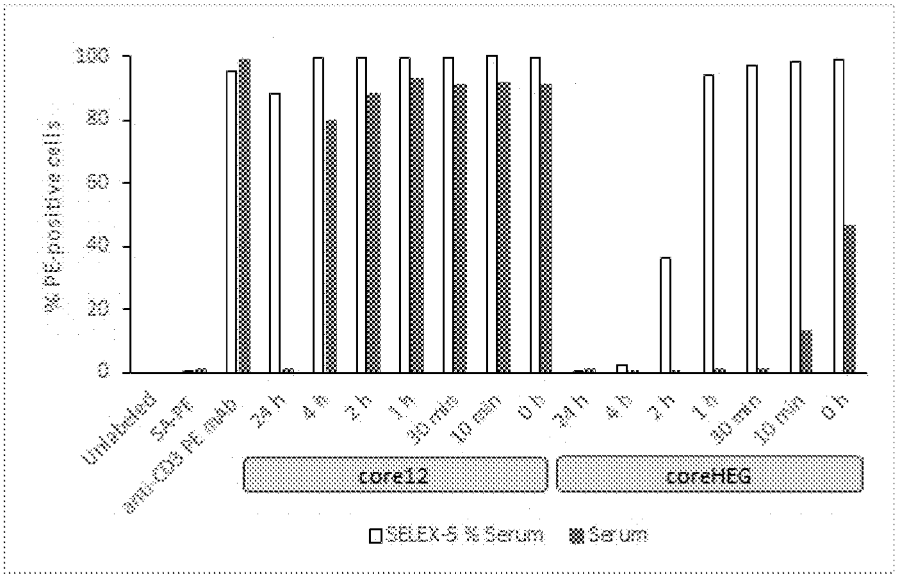
23B
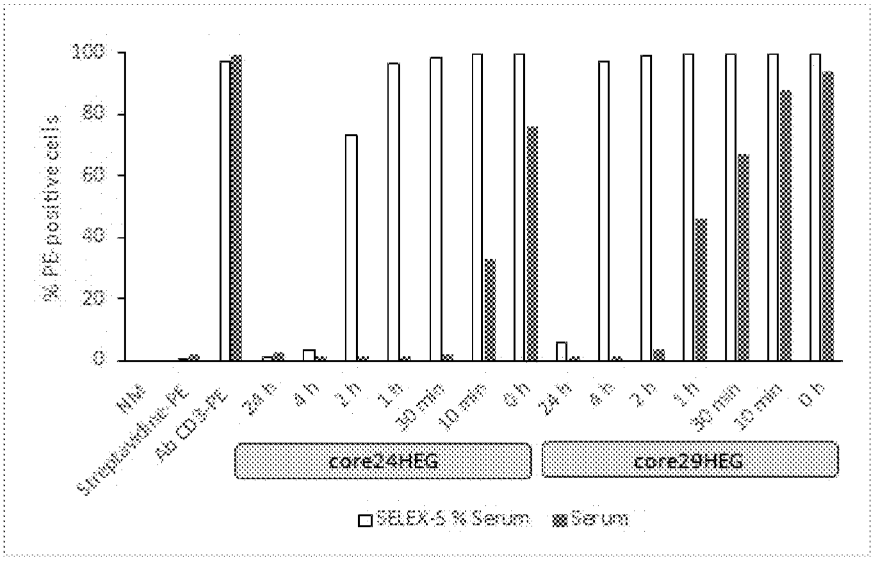
FIGS. 23 A-B

23C

24A
Core40HEG:
L 24 4 2 1 30 10 0 L 24 4 2 1 30 10 0 L 24 4 2 1 30 10
0
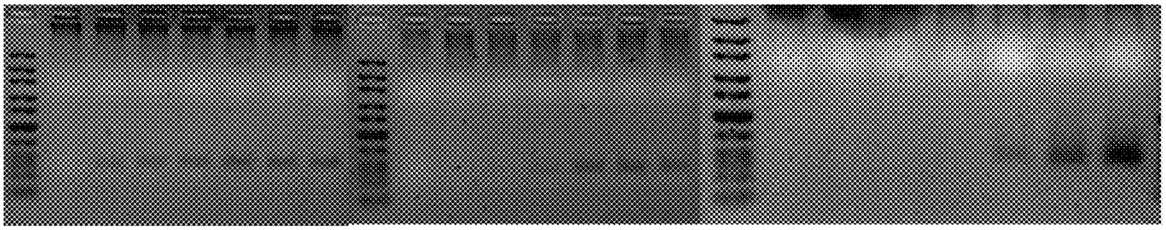
SELEX _ 5 % serum RPMI - 10 % serum serum
24B
core40HEGt
L 24 4 2 1 30 10 0 L 24 4 2 1 30 10 0 L 24 4 2 1 30 10
0
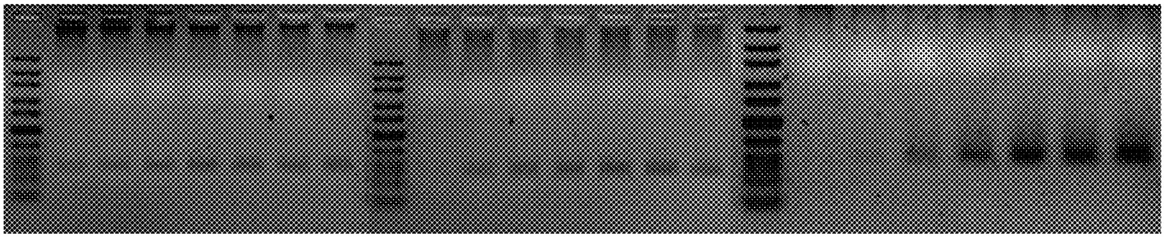
SELEX _ 5 % serum RPMI - 10 % serum serum
24C
Core42HEG:
L 24 4 2 1 30 10 0 L 24 4 2 1 30 10 0 L 24 4 2 1 30 10
0
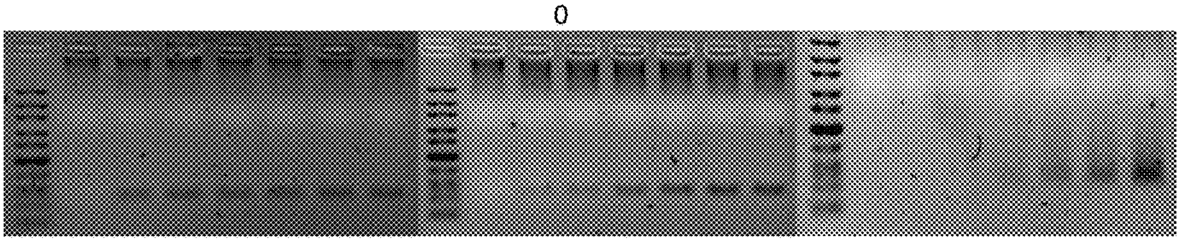
SELEX _ 5 % serum RPMI - 10 % serum serum
24D
core42HEGt
L 24 4 2 1 30 10 0 L 24 4 2 1 30 10 0 L 24 4 2 1 30 10
0
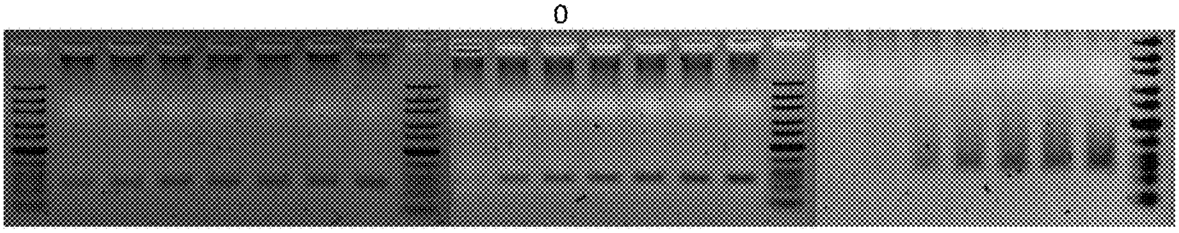
SELEX _ 5 % serum RPMI - 10 % serum serum
FIGS. 24 A-D 25A
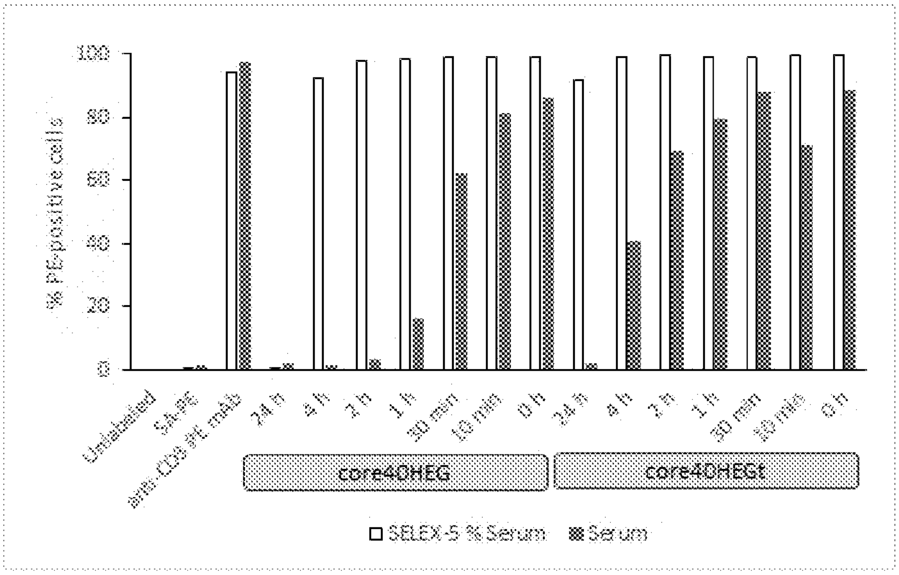
25B
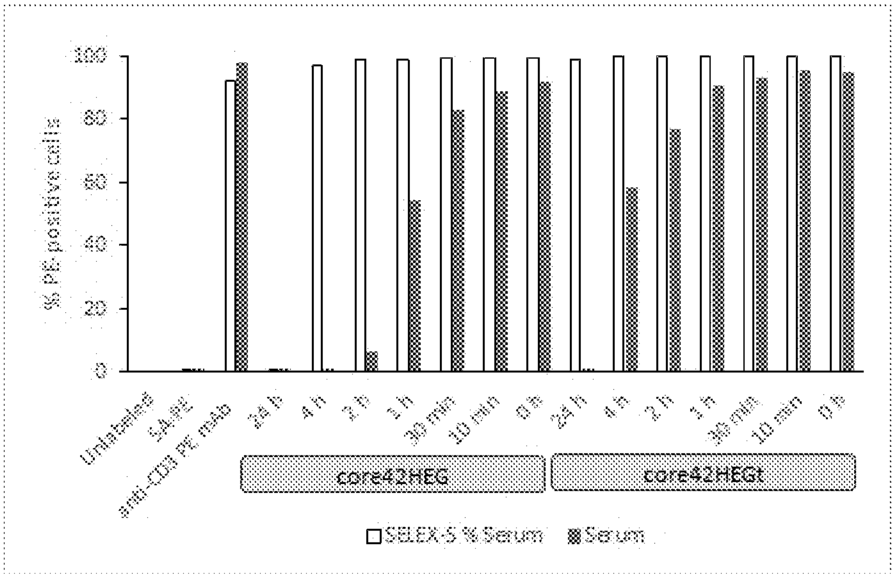
FIGS. 25 A-B

```
                   1                                                       57
ARACD3-0010209 (1) ---UCUAAGCAAUAUUGUUU-GCUUUU-GCAGCGAUUCU-GUUUC-GAUAUAUUA--
ARACD3-2980001 (1) ---UUCAAGAUAAUGUAAUU-AUUUUU-GCAGCGAUUCUUGUUUU-GUUCGAUUU--
ARACD3-0270039 (1) -----CAAAGUUCAAGAUUGAGCUUUUUGCAGCGAUUCUUGUUUU--AUCAAACGA-
ARACD3-3130001 (1) GAUGAUAU-CUUUAAUAUC--AAUU---GCAGCGAUUCUUGUUUGAGAAUAAAC---
ARACD3-3700006 (1) ---UAUAGACUUUAAUGUCUCAUUUUC-GCAGCGAUUCUUGUUU---AUUUAACAUA
                         *                ** *********** ****       *
```

FIG. 27

29A
29B
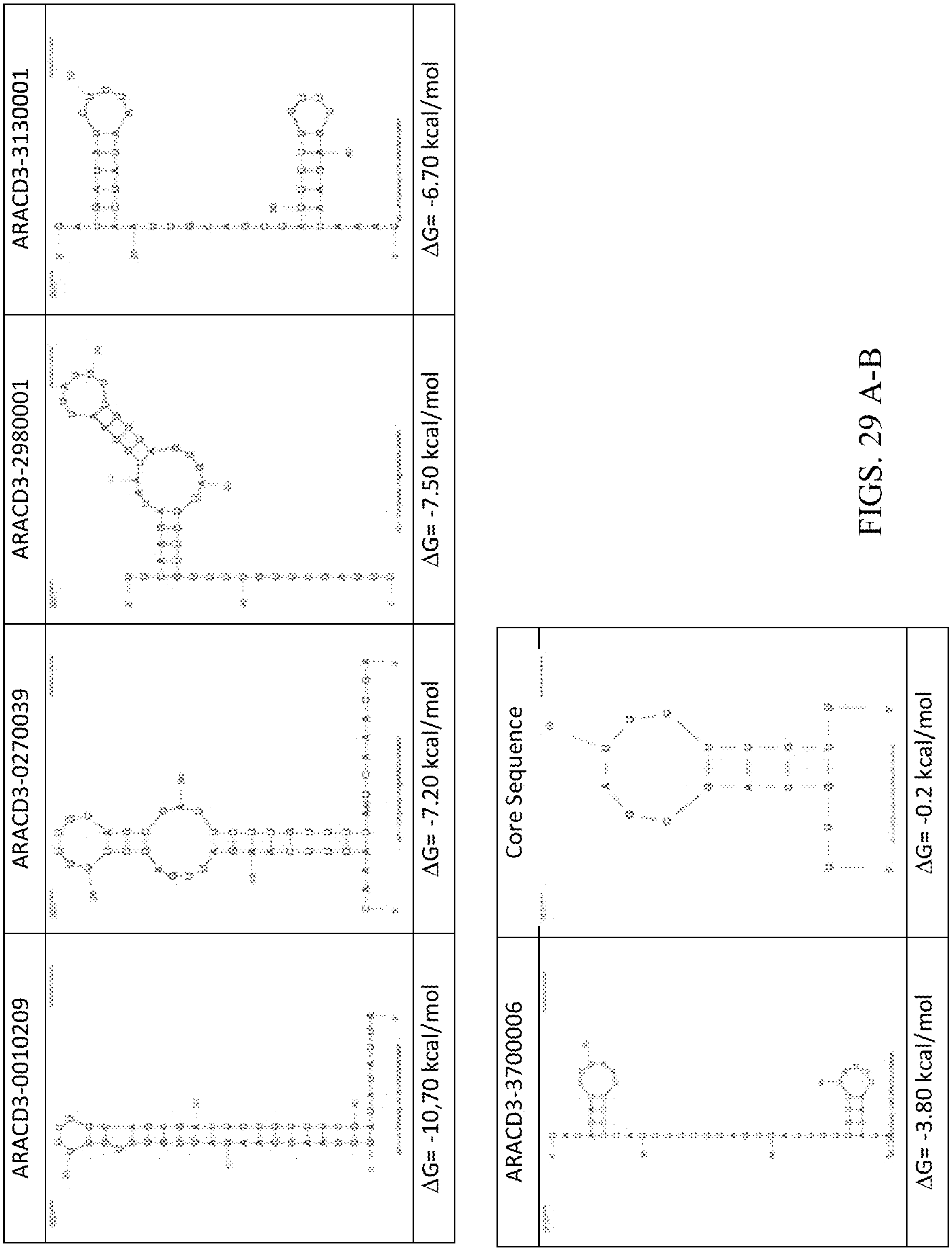
FIGS. 29 A-B

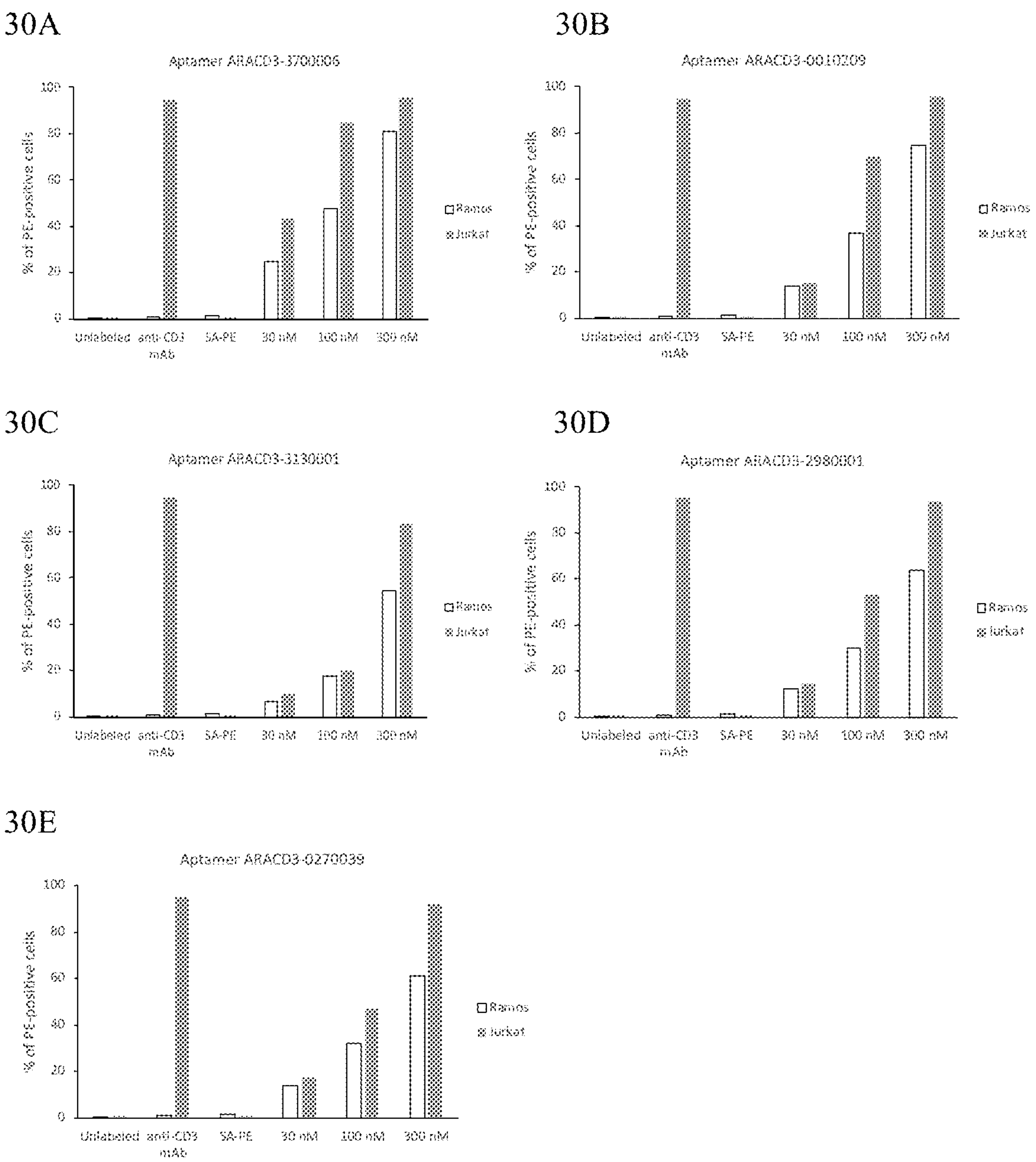
FIGS. 30A-E

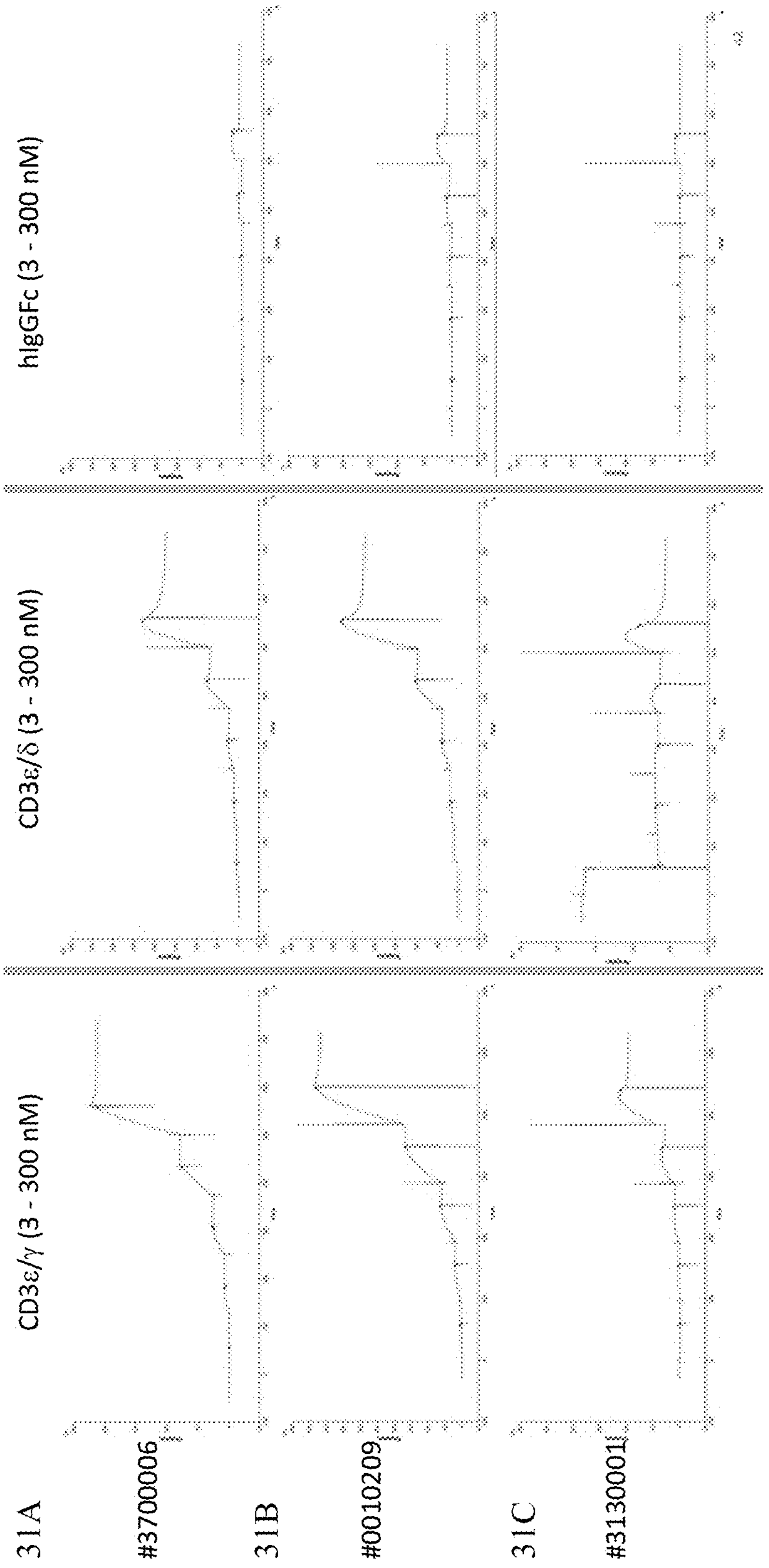
FIGS. 31A-C

32A
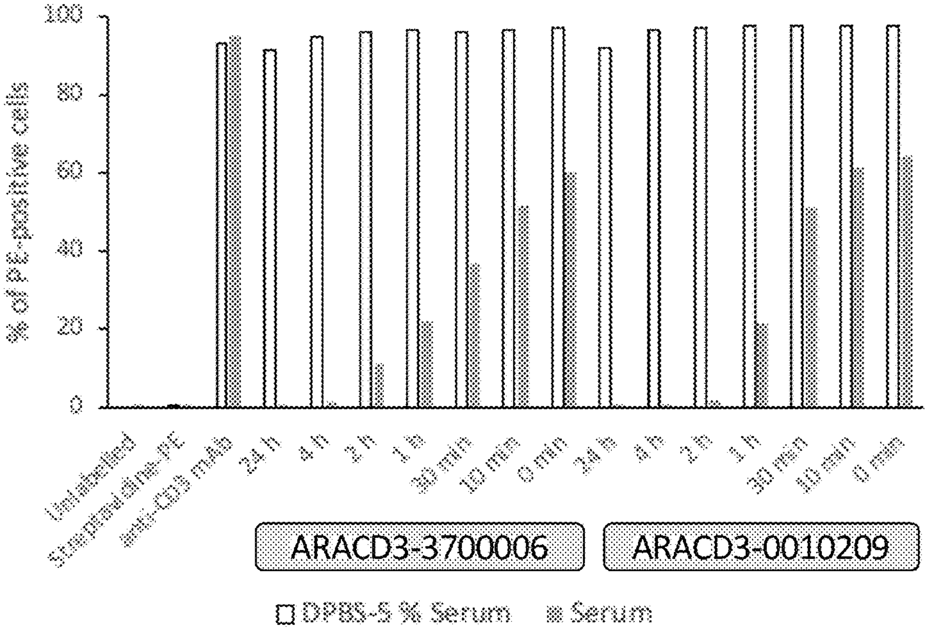
32B
ARAC D3-3700006
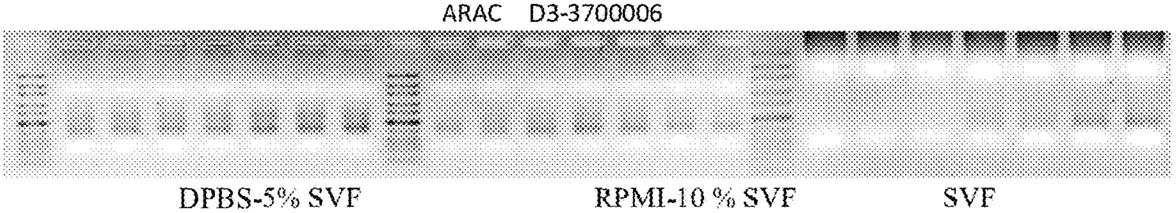
DPBS-5% SVF RPMI-10 % SVF SVF
32C
ARACD3-0010209
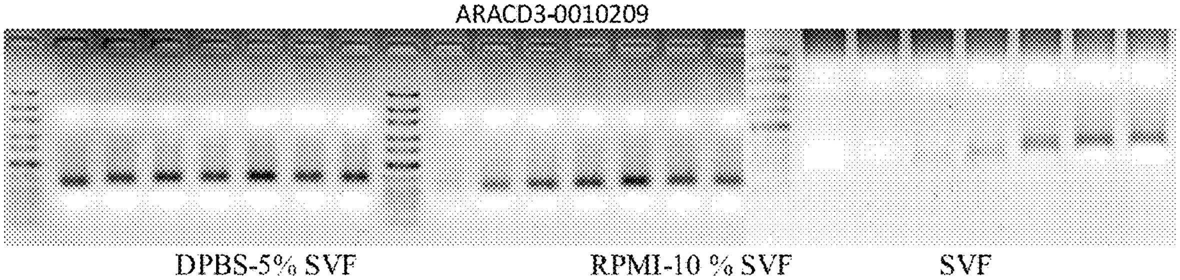
DPBS-5% SVF RPMI-10 % SVF SVF
FIGS. 32 A-C 34A
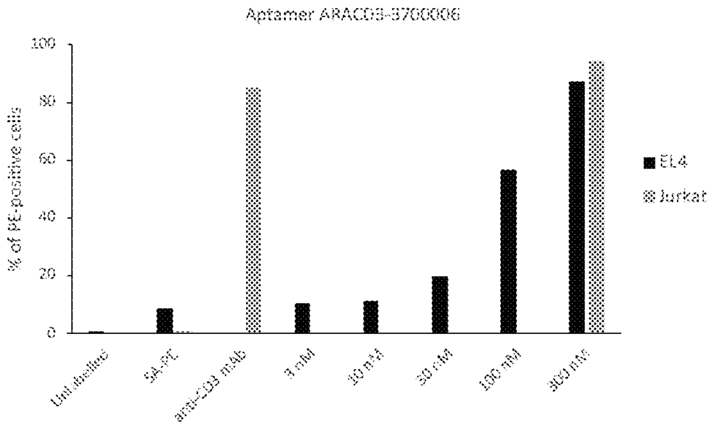
34B
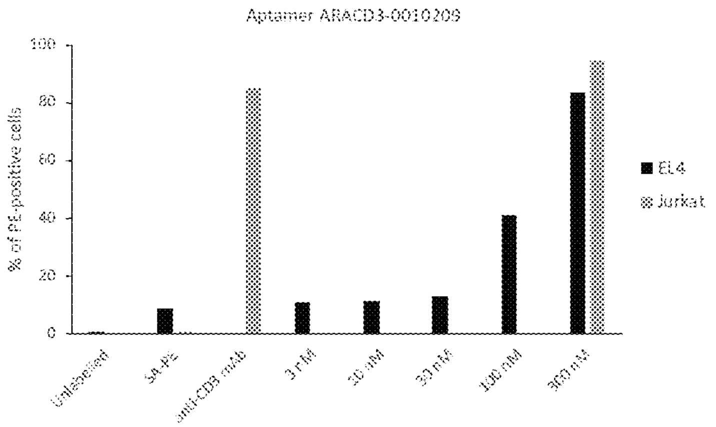
FIGS. 34 A-B

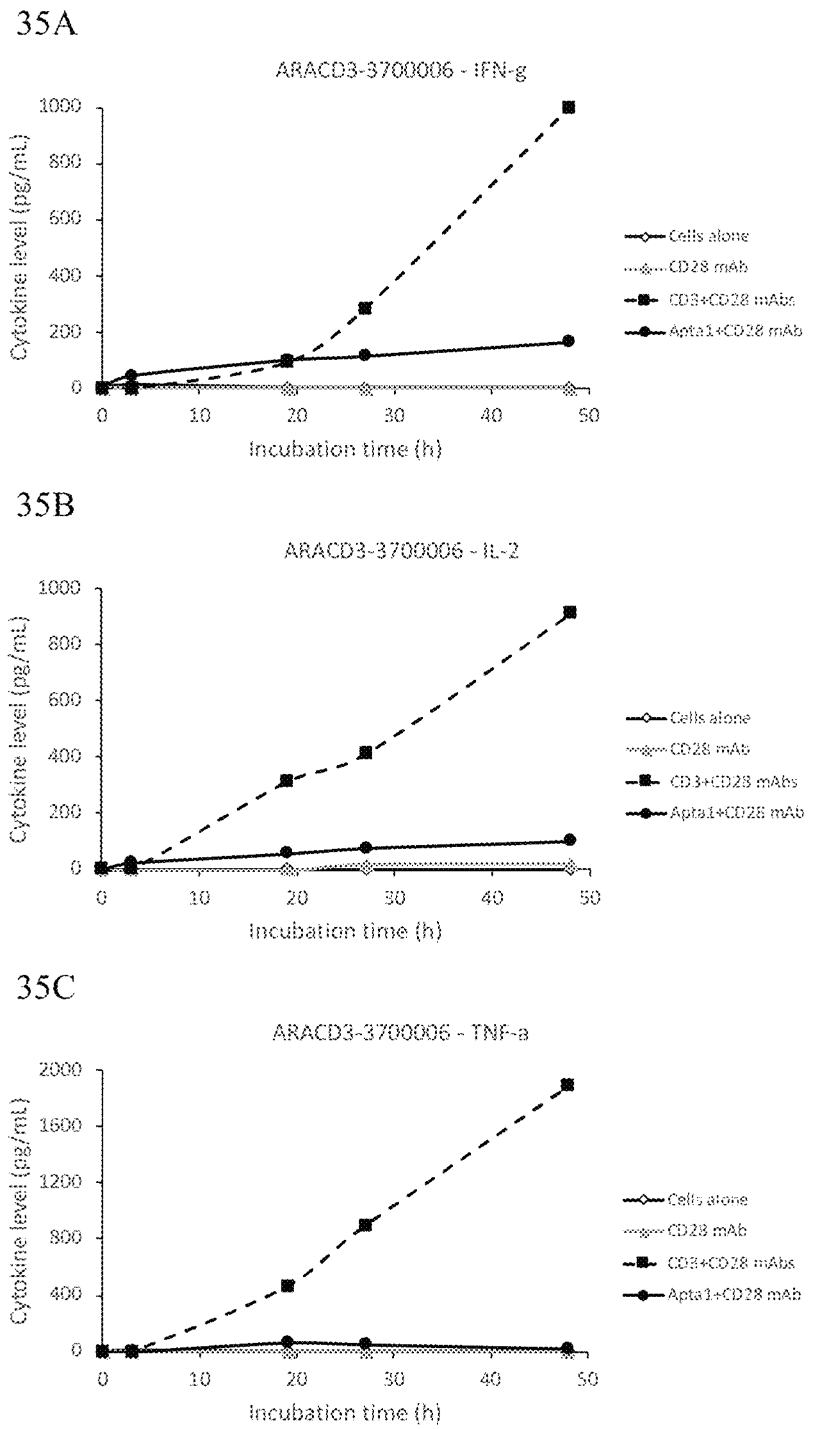
FIGS. 35A-C

35D
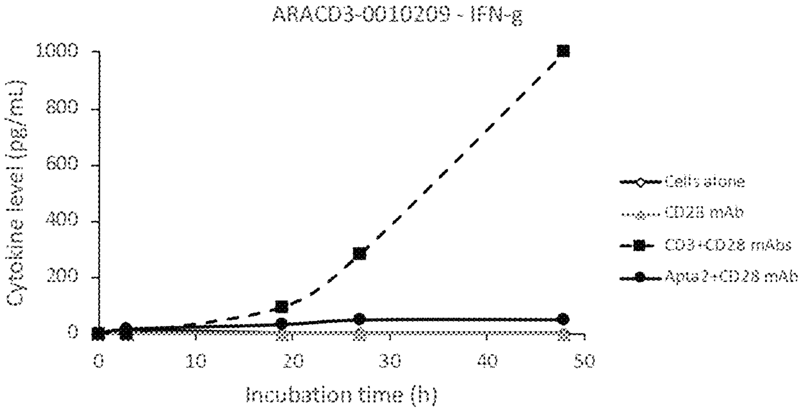
35E
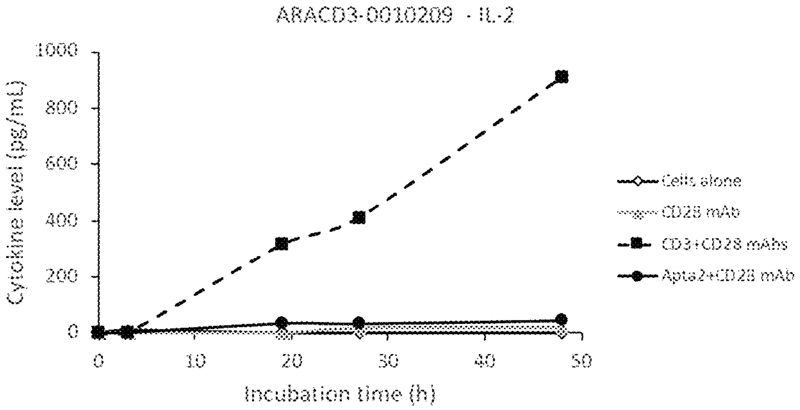
35F
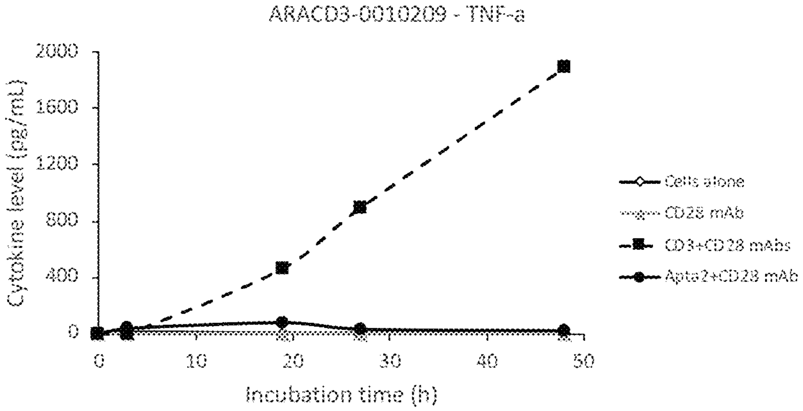
FIGS. 35D-F

36A
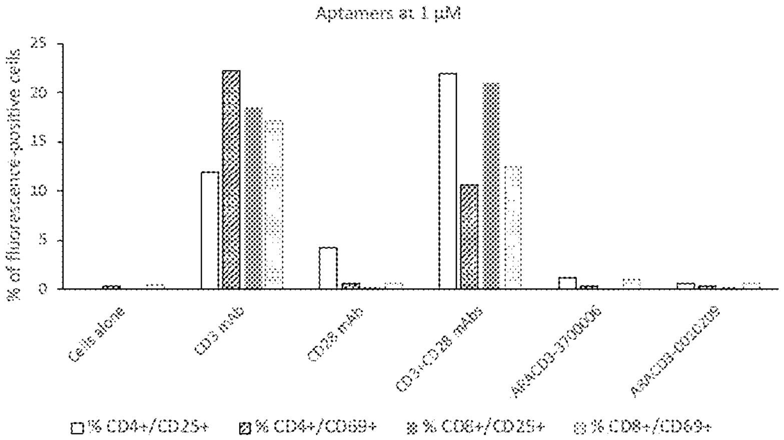
36B
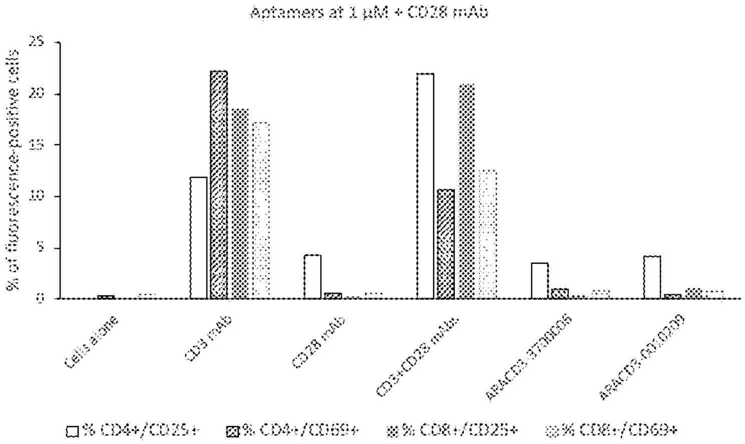
36C
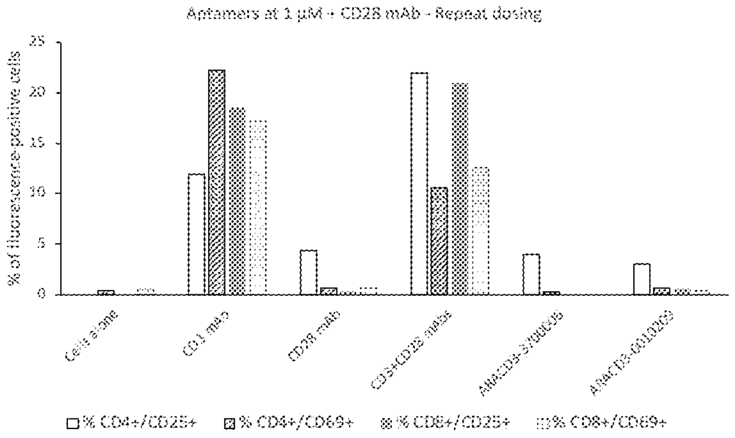
FIGS. 36 A-C

37A
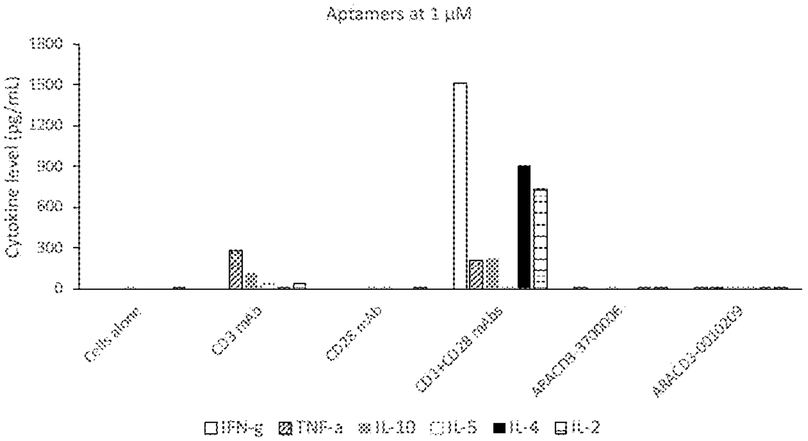
37B
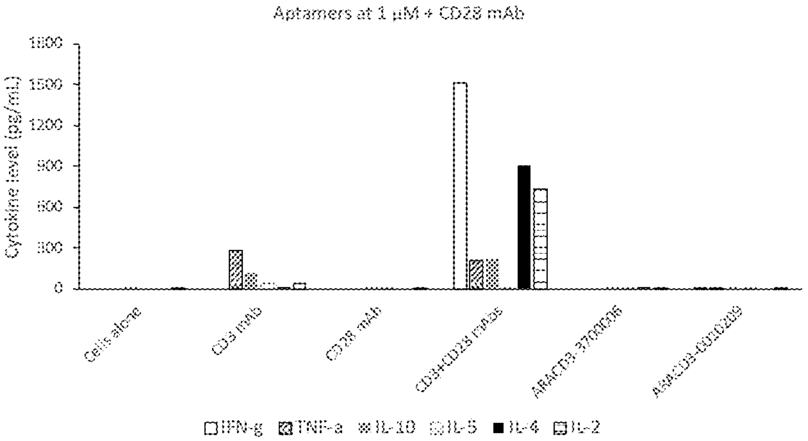
37C
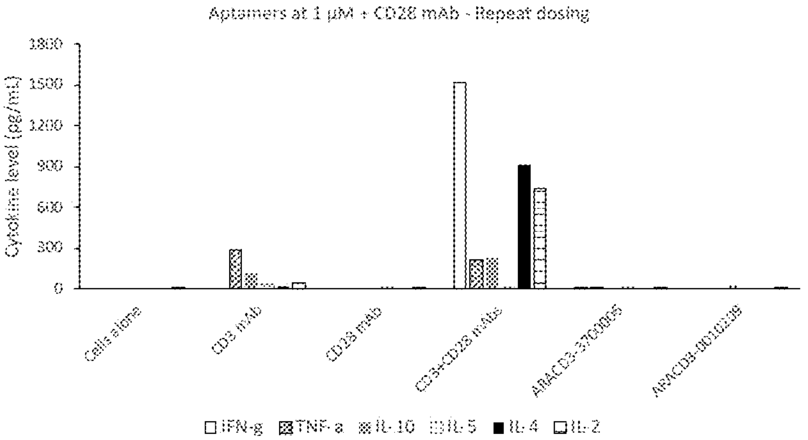
FIGS. 37 A-C

38A
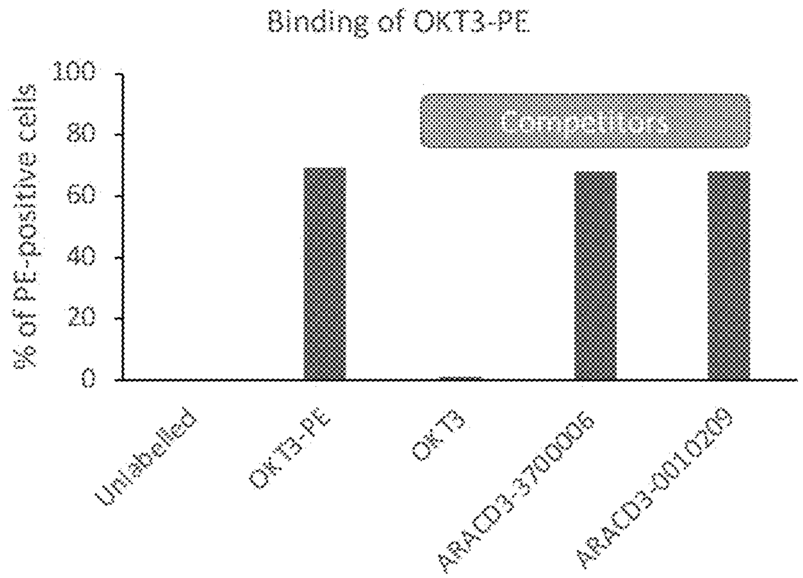
38B
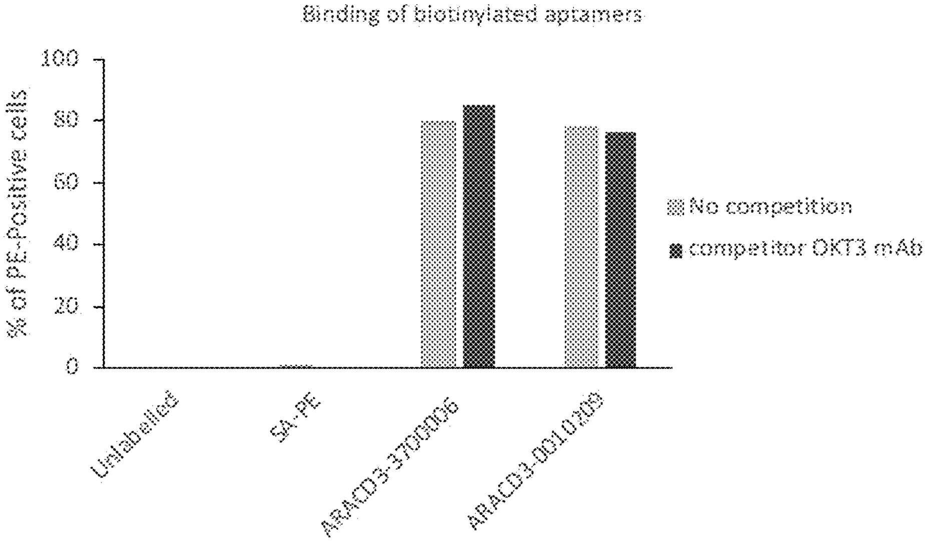
FIGS. 38 A-B

38C
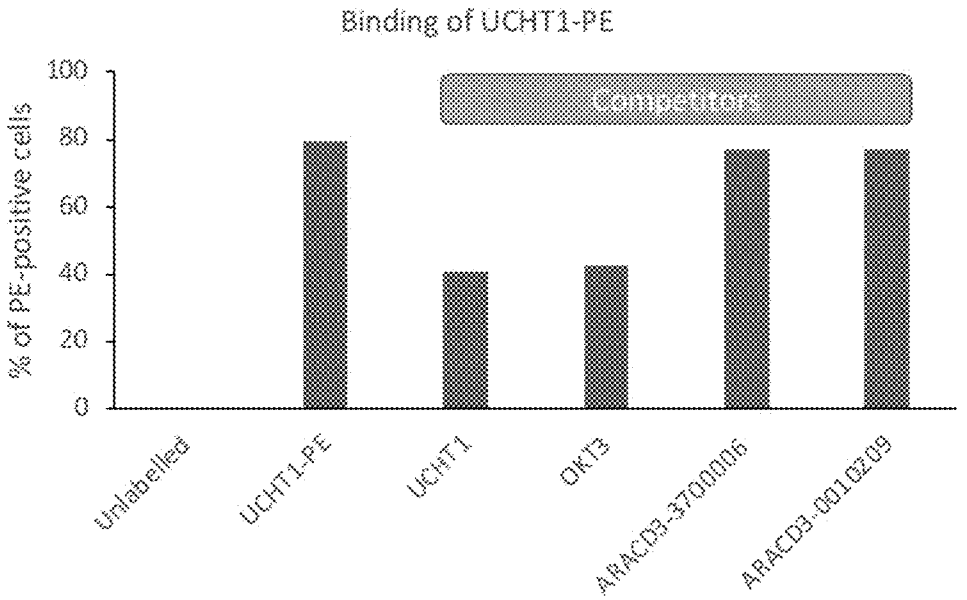
38D
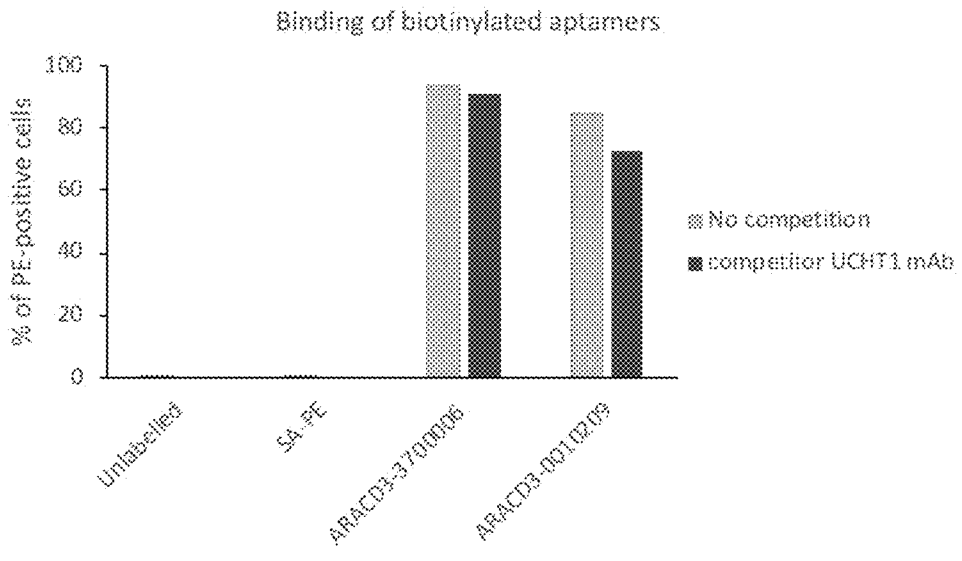
FIGS. 38 C-D

38E
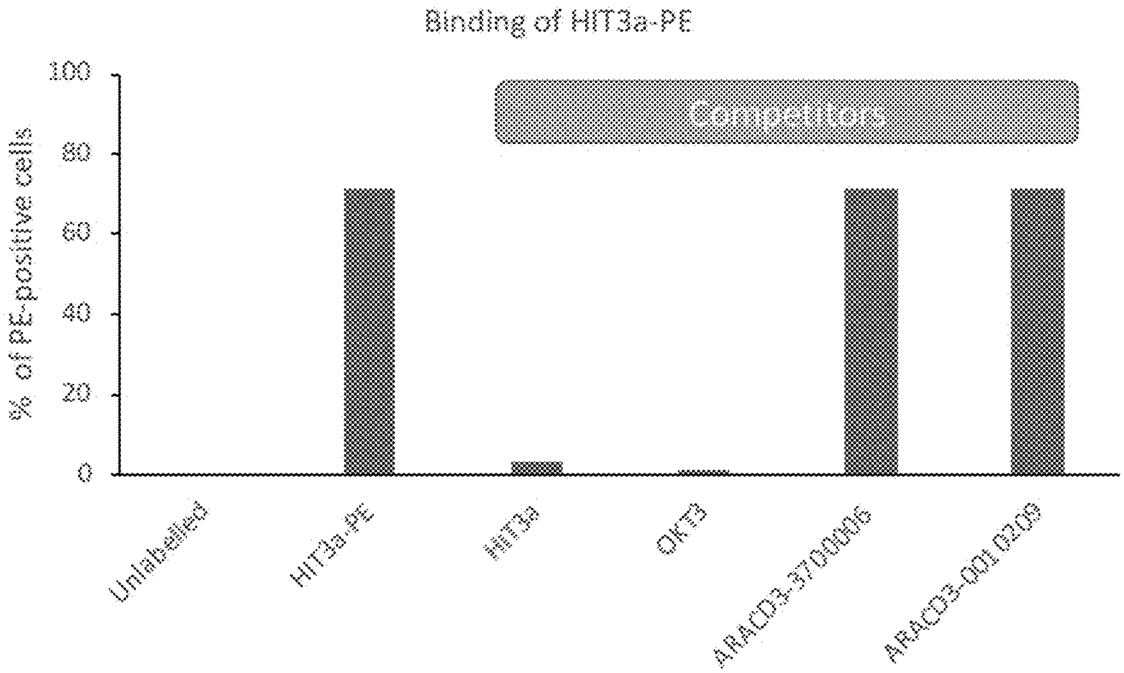
38F
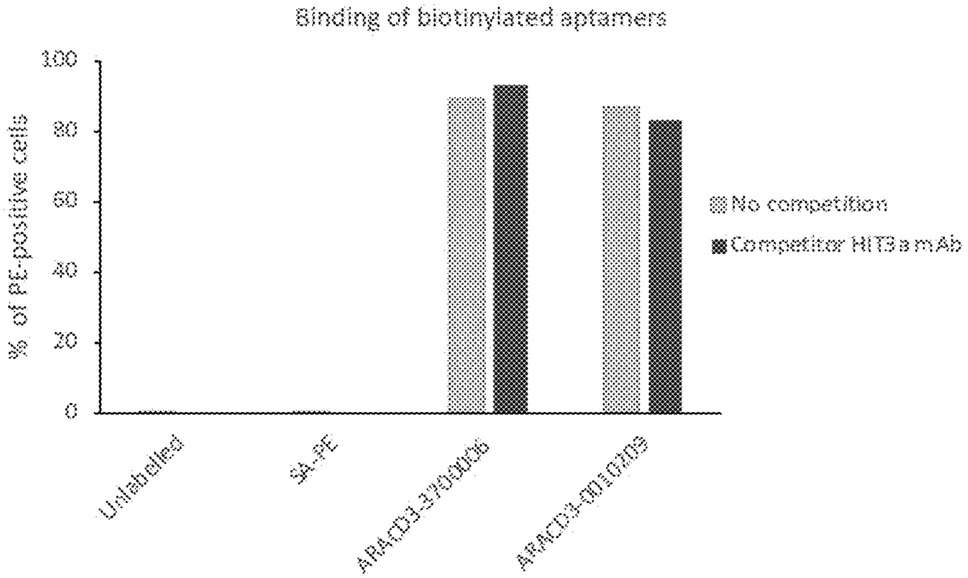
FIGS. 38 E-F

SEQUENCE LISTING

<160> NUMBER OF SEQ ID NOS: 122

<210> SEQ ID NO 1
<211> LENGTH: 40
<212> TYPE: DNA
<213> ORGANISM: Artificial Sequence
<220> FEATURE:
<223> OTHER INFORMATION: Cluster 1 aptamer

<400> SEQUENCE: 1
ccgggtgggg gtttggcacc gggcctggcg cagggattcg 40

<210> SEQ ID NO 2
<211> LENGTH: 40
<212> TYPE: DNA
<213> ORGANISM: Artificial Sequence
<220> FEATURE:
<223> OTHER INFORMATION: Cluster 2 aptamer

<400> SEQUENCE: 2
gaggggtttg gcatcgggcc tggcgccatt caagctatgc 40

<210> SEQ ID NO 3
<211> LENGTH: 40
<212> TYPE: DNA
<213> ORGANISM: Artificial Sequence
<220> FEATURE:
<223> OTHER INFORMATION: Cluster 3 aptamer

<400> SEQUENCE: 3
gcgtaagggt ttggcagcgg gcctggcgga acgcgtgtat 40

<210> SEQ ID NO 4
<211> LENGTH: 40
<212> TYPE: DNA
<213> ORGANISM: Artificial Sequence
<220> FEATURE:

<223> OTHER INFORMATION: Cluster 4 aptamer

<400> SEQUENCE: 4
ggagtggagt attccgggtt tggcatcggg cctggcgaag 40

<210> SEQ ID NO 5
<211> LENGTH: 40
<212> TYPE: DNA
<213> ORGANISM: Artificial Sequence
<220> FEATURE:
<223> OTHER INFORMATION: Cluster 5 aptamer

<400> SEQUENCE: 5
cggcaggggt ttggctccgg gtctggcgaa ctggctgaga 40

<210> SEQ ID NO 6
<211> LENGTH: 40
<212> TYPE: DNA
<213> ORGANISM: Artificial Sequence
<220> FEATURE:
<223> OTHER INFORMATION: Cluster 6 aptamer

<400> SEQUENCE: 6
aagggattgg cgtcgggcct ggcgtaagga ggctatgctc 40

<210> SEQ ID NO 7
<211> LENGTH: 40
<212> TYPE: DNA
<213> ORGANISM: Artificial Sequence
<220> FEATURE:
<223> OTHER INFORMATION: Cluster 7 aptamer

<400> SEQUENCE: 7
gggattggcg ctgggcctgg caaggaatct tctcgttgta 40

<210> SEQ ID NO 8
<211> LENGTH: 40
<212> TYPE: DNA
<213> ORGANISM: Artificial Sequence
<220> FEATURE:
<223> OTHER INFORMATION: Cluster 8

<400> SEQUENCE: 8
gggattggct tcgggcctgg cgagtattgt tttcctggag 40

<210> SEQ ID NO 9
<211> LENGTH: 40
<212> TYPE: DNA
<213> ORGANISM: Artificial Sequence
<220> FEATURE:
<223> OTHER INFORMATION: Cluster 9 aptamer

<400> SEQUENCE: 9
gcatcgaaat ggggttggca ccgggcctgg cgaattggat 40

<210> SEQ ID NO 10
<211> LENGTH: 34
<212> TYPE: DNA
<213> ORGANISM: Artificial Sequence
<220> FEATURE:
<223> OTHER INFORMATION: Cluster 10 aptamer

<400> SEQUENCE: 10
gagactagag ggattggctt cgggcctggc gtac 34

<210> SEQ ID NO 11
<211> LENGTH: 40
<212> TYPE: DNA
<213> ORGANISM: Artificial Sequence
<220> FEATURE:
<223> OTHER INFORMATION: Cluster 11 aptamer

<400> SEQUENCE: 11
gatggagggt ttggcggtgg gcctggcaag ttatctcata 40

<210> SEQ ID NO 12
<211> LENGTH: 40
<212> TYPE: DNA
<213> ORGANISM: Artificial Sequence
<220> FEATURE:
<223> OTHER INFORMATION: Cluster 12 aptamer

<400> SEQUENCE: 12
tacggctagg gtttggcgtt gggcctggca ggaccgtaag 40

<210> SEQ ID NO 13
<211> LENGTH: 40
<212> TYPE: DNA
<213> ORGANISM: Artificial Sequence
<220> FEATURE:
<223> OTHER INFORMATION: Cluster 13 aptamer

<400> SEQUENCE: 13
atatgggagg gtgagggttt ggctgcgggc ctggcgggag 40

<210> SEQ ID NO 14
<211> LENGTH: 40
<212> TYPE: DNA
<213> ORGANISM: Artificial Sequence
<220> FEATURE:
<223> OTHER INFORMATION: Cluster 14 aptamer

<400> SEQUENCE: 14
tgcggcacat gtacgcggag ggattggcat agggtctggc 40

<210> SEQ ID NO 15
<211> LENGTH: 40
<212> TYPE: DNA
<213> ORGANISM: Artificial Sequence
<220> FEATURE:
<223> OTHER INFORMATION: Cluster 15 aptamer

<400> SEQUENCE: 15
ggggttggct ttgggcctgg cagtcatttg tgaatcctta 40

<210> SEQ ID NO 16
<211> LENGTH: 40
<212> TYPE: DNA
<213> ORGANISM: Artificial Sequence
<220> FEATURE:
<223> OTHER INFORMATION: Cluster 16 aptamer

<400> SEQUENCE: 16
tccgacaaaa gggattggct tcgggcctgg cggggttgcc 40

<210> SEQ ID NO 17
<211> LENGTH: 39
<212> TYPE: DNA
<213> ORGANISM: Artificial Sequence
<220> FEATURE:
<223> OTHER INFORMATION: Cluster 17 aptamer

<400> SEQUENCE: 17
ggtcggggtt tggcatcggg actggcgtta tacaatcgt 39

<210> SEQ ID NO 18
<211> LENGTH: 40
<212> TYPE: DNA
<213> ORGANISM: Artificial Sequence
<220> FEATURE:
<223> OTHER INFORMATION: Cluster 18 aptamer

<400> SEQUENCE: 18
gatggggttt ggcgtcgggc ctggcgaata catctaaaag 40

<210> SEQ ID NO 19
<211> LENGTH: 40
<212> TYPE: DNA
<213> ORGANISM: Artificial Sequence
<220> FEATURE:
<223> OTHER INFORMATION: Cluster 19 aptamer

<400> SEQUENCE: 19
taccgcgggg attggctccg ggcctggcgt cgtaatctga 40

<210> SEQ ID NO 20
<211> LENGTH: 40
<212> TYPE: DNA
<213> ORGANISM: Artificial Sequence
<220> FEATURE:
<223> OTHER INFORMATION: Cluster 20 aptamer

<400> SEQUENCE: 20
ggggtttggc tgcgggcctg gcgcatgatt caacgagaca 40

<210> SEQ ID NO 21
<211> LENGTH: 40
<212> TYPE: DNA
<213> ORGANISM: Artificial Sequence
<220> FEATURE:
<223> OTHER INFORMATION: Cluster 21 aptamer

<400> SEQUENCE: 21
ggtcgggtgc tactgagcga ttggctttcc ggactgggga 40

<210> SEQ ID NO 22
<211> LENGTH: 40
<212> TYPE: DNA
<213> ORGANISM: Artificial Sequence
<220> FEATURE:
<223> OTHER INFORMATION: Cluster 22 aptamer

<400> SEQUENCE: 22
cgaccacagg ggtttggctt cgggactggc ggtgggcact 40

<210> SEQ ID NO 23
<211> LENGTH: 40
<212> TYPE: DNA
<213> ORGANISM: Artificial Sequence
<220> FEATURE:
<223> OTHER INFORMATION: Cluster 23 aptamer

<400> SEQUENCE: 23
cgaccacagg ggtttggctt cgggactggc ggtgggcact 40

<210> SEQ ID NO 24
<211> LENGTH: 40

<212> TYPE: DNA
<213> ORGANISM: Artificial Sequence
<220> FEATURE:
<223> OTHER INFORMATION: Cluster 24 aptamer

<400> SEQUENCE: 24
tatgggtttg gcatcgggcc tggcggaatg gaaaatgtta 40

<210> SEQ ID NO 25
<211> LENGTH: 40
<212> TYPE: DNA
<213> ORGANISM: Artificial Sequence
<220> FEATURE:
<223> OTHER INFORMATION: Cluster 25 aptamer

<400> SEQUENCE: 25
agacgggttt ggctgcgggc ctggcggtcg tcattcctct 40

<210> SEQ ID NO 26
<211> LENGTH: 40
<212> TYPE: DNA
<213> ORGANISM: Artificial Sequence
<220> FEATURE:
<223> OTHER INFORMATION: Cluster 26 aptamer

<400> SEQUENCE: 26
gaggggattg gcatttgggc ctggcaaatt catctattct 40

<210> SEQ ID NO 27
<211> LENGTH: 41
<212> TYPE: DNA
<213> ORGANISM: Artificial Sequence
<220> FEATURE:
<223> OTHER INFORMATION: Cluster 27 aptamer

<400> SEQUENCE: 27
aggggtttgg cgtcgggcct ggcgcagctc ttcttgtgtt t 41

<210> SEQ ID NO 28
<211> LENGTH: 38
<212> TYPE: DNA
<213> ORGANISM: Artificial Sequence
<220> FEATURE:
<223> OTHER INFORMATION: Cluster 28 aptamer

<400> SEQUENCE: 28
gggattggct tcgggcctgg cgtatctttt acattacc 38

<210> SEQ ID NO 29
<211> LENGTH: 40
<212> TYPE: DNA
<213> ORGANISM: Artificial Sequence
<220> FEATURE:
<223> OTHER INFORMATION: Cluster 29 aptamer

<400> SEQUENCE: 29
ggtggacggt atacaggggc tgctcaggat tgcggatgat 40

<210> SEQ ID NO 30
<211> LENGTH: 40
<212> TYPE: DNA
<213> ORGANISM: Artificial Sequence
<220> FEATURE:
<223> OTHER INFORMATION: Cluster 30 aptamer

<400> SEQUENCE: 30
ccgtttgaag cgttagggtt tggcatcggg cctggcgcac 40

<210> SEQ ID NO 31
<211> LENGTH: 40
<212> TYPE: DNA
<213> ORGANISM: Artificial Sequence
<220> FEATURE:
<223> OTHER INFORMATION: Cluster 31 aptamer

<400> SEQUENCE: 31
agggtttggc tacgggcctg gcgagctgtt tccgctactc 40

<210> SEQ ID NO 32
<211> LENGTH: 40
<212> TYPE: DNA
<213> ORGANISM: Artificial Sequence
<220> FEATURE:
<223> OTHER INFORMATION: Cluster 32 aptamer

<400> SEQUENCE: 32
gtgttatgat actatgcgta tggattgcaa agggctgctg 40

<210> SEQ ID NO 33
<211> LENGTH: 40
<212> TYPE: DNA
<213> ORGANISM: Artificial Sequence
<220> FEATURE:
<223> OTHER INFORMATION: Cluster 33 aptamer

<400> SEQUENCE: 33
gaagggtttg gcattgggcc tggcaagata atttgcaagt 40

<210> SEQ ID NO 34
<211> LENGTH: 40
<212> TYPE: DNA
<213> ORGANISM: Artificial Sequence
<220> FEATURE:
<223> OTHER INFORMATION: Cluster 34 aptamer

<400> SEQUENCE: 34
cggcgaagtg gcagggtttg gcttcgggtc tggcggaaca 40

<210> SEQ ID NO 35
<211> LENGTH: 40
<212> TYPE: DNA
<213> ORGANISM: Artificial Sequence
<220> FEATURE:
<223> OTHER INFORMATION: Cluster 35 aptamer

<400> SEQUENCE: 35
gagggtttgg cagtgggcct ggcatcaatt ctttgttttc 40

<210> SEQ ID NO 36
<211> LENGTH: 39
<212> TYPE: DNA
<213> ORGANISM: Artificial Sequence
<220> FEATURE:
<223> OTHER INFORMATION: Cluster 36 aptamer

<400> SEQUENCE: 36
tactgagggt ttggcattgg gcctggcata ttggtattt 39

<210> SEQ ID NO 37
<211> LENGTH: 40
<212> TYPE: DNA
<213> ORGANISM: Artificial Sequence
<220> FEATURE:
<223> OTHER INFORMATION: Cluster 37 aptamer

<400> SEQUENCE: 37
atgggtttgg caccgggtct ggcggattcg ataggtggtt 40

<210> SEQ ID NO 38
<211> LENGTH: 40
<212> TYPE: DNA
<213> ORGANISM: Artificial Sequence
<220> FEATURE:
<223> OTHER INFORMATION: Cluster 38 aptamer

<400> SEQUENCE: 38
gggggtttgg ctctgggcct ggcataacga accttcggag 40

<210> SEQ ID NO 39
<211> LENGTH: 40
<212> TYPE: DNA
<213> ORGANISM: Artificial Sequence
<220> FEATURE:
<223> OTHER INFORMATION: Cluster 39 aptamer

<400> SEQUENCE: 39
tgcccgagag gactgcttag gcttgcgagt agggaacgct 40

<210> SEQ ID NO 40
<211> LENGTH: 40
<212> TYPE: DNA
<213> ORGANISM: Artificial Sequence
<220> FEATURE:
<223> OTHER INFORMATION: Cluster 40 aptamer

<400> SEQUENCE: 40
agtgggattg gcttcgggcc tggcgttcgc aacatgttta 40

<210> SEQ ID NO 41
<211> LENGTH: 40
<212> TYPE: DNA
<213> ORGANISM: Artificial Sequence
<220> FEATURE:
<223> OTHER INFORMATION: Cluster 41 aptamer

<400> SEQUENCE: 41
ggggattggc actgggactg gcaccttttt aacatgtatg 40

<210> SEQ ID NO 42
<211> LENGTH: 40
<212> TYPE: DNA
<213> ORGANISM: Artificial Sequence
<220> FEATURE:
<223> OTHER INFORMATION: Cluster 42 aptamer

<400> SEQUENCE: 42
gcaattaagg gattggctcc gggcctggcg ccacgcatgg 40

<210> SEQ ID NO 43
<211> LENGTH: 40
<212> TYPE: DNA
<213> ORGANISM: Artificial Sequence
<220> FEATURE:
<223> OTHER INFORMATION: Cluster 43 aptamer

<400> SEQUENCE: 43
tggggtttgg cagcgggtct ggcgatcata atggtgtgcg 40

<210> SEQ ID NO 44
<211> LENGTH: 40
<212> TYPE: DNA
<213> ORGANISM: Artificial Sequence
<220> FEATURE:
<223> OTHER INFORMATION: Cluster 44 aptamer

<400> SEQUENCE: 44
acgggggatt ggctttgggc ctggcaatta atttactgtt 40

<210> SEQ ID NO 45
<211> LENGTH: 40
<212> TYPE: DNA
<213> ORGANISM: Artificial Sequence
<220> FEATURE:
<223> OTHER INFORMATION: Cluster 45 aptamer

<400> SEQUENCE: 45
gagcgcttgg cagccggtct ggggacatca gaggtgatgg 40

<210> SEQ ID NO 46
<211> LENGTH: 43
<212> TYPE: DNA
<213> ORGANISM: Artificial Sequence
<220> FEATURE:
<223> OTHER INFORMATION: CELTIC_1s aptamer

<400> SEQUENCE: 46
tttccgggtg ggggtttggc accgggcctg gcgcagggat tcg 43

<210> SEQ ID NO 47
<211> LENGTH: 40
<212> TYPE: DNA
<213> ORGANISM: Artificial Sequence
<220> FEATURE:
<223> OTHER INFORMATION: CELTIC_2s aptamer

<400> SEQUENCE: 47
gaggggtttg gcatcgggcc tggcgccatt caagctatgc 40

<210> SEQ ID NO 48
<211> LENGTH: 40
<212> TYPE: DNA
<213> ORGANISM: Artificial Sequence
<220> FEATURE:
<223> OTHER INFORMATION: CELTIC_3s aptamer

<400> SEQUENCE: 48
gcgtaagggt ttggcagcgg gcctggcgga acgcgtgtat 40

<210> SEQ ID NO 49
<211> LENGTH: 40
<212> TYPE: DNA
<213> ORGANISM: Artificial Sequence
<220> FEATURE:
<223> OTHER INFORMATION: CELTIC_21s aptamer

<400> SEQUENCE: 49
ggtcgggtgc tactgagcga ttggctttcc ggactgggga 40

<210> SEQ ID NO 50
<211> LENGTH: 40
<212> TYPE: DNA
<213> ORGANISM: Artificial Sequence
<220> FEATURE:
<223> OTHER INFORMATION: CELTIC_4s aptamer

<400> SEQUENCE: 50
ggagtggagt attccgggtt tggcatcggg cctggcgaag 40

<210> SEQ ID NO 51
<211> LENGTH: 40
<212> TYPE: DNA
<213> ORGANISM: Artificial Sequence
<220> FEATURE:
<223> OTHER INFORMATION: CELTIC_5s aptamer

<400> SEQUENCE: 51
cggcaggggt ttggctccgg gtctggcgaa ctggctgaga 40

<210> SEQ ID NO 52
<211> LENGTH: 40
<212> TYPE: DNA
<213> ORGANISM: Artificial Sequence
<220> FEATURE:
<223> OTHER INFORMATION: CELTIC_6s sequence

<400> SEQUENCE: 52
aagggattgg cgtcgggcct ggcgtaagga ggctatgctc 40

<210> SEQ ID NO 53
<211> LENGTH: 40
<212> TYPE: DNA
<213> ORGANISM: Artificial Sequence
<220> FEATURE:
<223> OTHER INFORMATION: CELTIC_9s aptamer

<400> SEQUENCE: 53
gcatcgaaat ggggttggca ccgggcctgg cgaattggat 40

<210> SEQ ID NO 54
<211> LENGTH: 40
<212> TYPE: DNA
<213> ORGANISM: Artificial Sequence
<220> FEATURE:
<223> OTHER INFORMATION: CELTIC_11s aptamer

<400> SEQUENCE: 54
gatggagggt ttggcggtgg gcctggcaag ttatctcata 40

<210> SEQ ID NO 55
<211> LENGTH: 40
<212> TYPE: DNA
<213> ORGANISM: Artificial Sequence
<220> FEATURE:
<223> OTHER INFORMATION: CELTIC_19s aptamer

<400> SEQUENCE: 55
taccgcgggg attggctccg ggcctggcgt cgtaatctga 40

<210> SEQ ID NO 56
<211> LENGTH: 40
<212> TYPE: DNA
<213> ORGANISM: Artificial Sequence
<220> FEATURE:
<223> OTHER INFORMATION: CELTIC_22s aptamer

<400> SEQUENCE: 56
cgaccacagg ggtttggctt cgggactggc ggtgggcact 40

<210> SEQ ID NO 57

<211> LENGTH: 21
<212> TYPE: DNA
<213> ORGANISM: Artificial Sequence
<220> FEATURE:
<223> OTHER INFORMATION: CELTIC core aptamer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 57
gggnttggcn nngggnctgg c 21

<210> SEQ ID NO 58
<211> LENGTH: 23
<212> TYPE: DNA
<213> ORGANISM: Artificial Sequence
<220> FEATURE:
<223> OTHER INFORMATION: CELTIC core_1 aptamer

<400> SEQUENCE: 58
gggtttggca ccgggcctgg cgc 23

<210> SEQ ID NO 59
<211> LENGTH: 21
<212> TYPE: DNA
<213> ORGANISM: Artificial Sequence
<220> FEATURE:
<223> OTHER INFORMATION: CELTIC core_2 aptamer

<400> SEQUENCE: 59
gggtttggca ccgggcctgg c 21

<210> SEQ ID NO 60
<211> LENGTH: 12
<212> TYPE: DNA
<213> ORGANISM: Artificial Sequence
<220> FEATURE:
<223> OTHER INFORMATION: CELTIC core_3 aptamer

<400> SEQUENCE: 60
ccgggcctgg cc 12

<210> SEQ ID NO 61
<211> LENGTH: 22
<212> TYPE: DNA
<213> ORGANISM: Artificial Sequence
<220> FEATURE:
<223> OTHER INFORMATION: CELTIC core_4 aptamer

<400> SEQUENCE: 61
gggtttggca tcgggcctgg cg 22

<210> SEQ ID NO 62
<211> LENGTH: 21
<212> TYPE: DNA
<213> ORGANISM: Artificial Sequence
<220> FEATURE:
<223> OTHER INFORMATION: CELTIC core_5 aptamer

<400> SEQUENCE: 62
gggtttggcg gtgggcctgg c 21

<210> SEQ ID NO 63
<211> LENGTH: 24
<212> TYPE: DNA
<213> ORGANISM: Artificial Sequence
<220> FEATURE:
<223> OTHER INFORMATION: CELTIC core_6 aptamer

<400> SEQUENCE: 63
tttgggtttg gcaccgggcc tggc 24

<210> SEQ ID NO 64
<211> LENGTH: 24
<212> TYPE: DNA
<213> ORGANISM: Artificial Sequence
<220> FEATURE:
<223> OTHER INFORMATION: CELTIC core_T aptamer

<400> SEQUENCE: 64
tttgggtttg gcatcgggcc tggc 24

<210> SEQ ID NO 65
<211> LENGTH: 21
<212> TYPE: DNA
<213> ORGANISM: Artificial Sequence
<220> FEATURE:
<223> OTHER INFORMATION: CELTIC core_7 aptamer
<220> FEATURE:
<221> NAME/KEY: misc_feature
<222> LOCATION: (7)..(7)
<223> OTHER INFORMATION: n is a, c, g, or t

<400> SEQUENCE: 65
gggtttngca ccgggcctgg c 21

<210> SEQ ID NO 66
<211> LENGTH: 21
<212> TYPE: DNA
<213> ORGANISM: Artificial Sequence
<220> FEATURE:
<223> OTHER INFORMATION: CELTIC core_8 aptamer
<220> FEATURE:
<221> NAME/KEY: misc_feature
<222> LOCATION: (8)..(8)
<223> OTHER INFORMATION: n is a, c, g, or t

<400> SEQUENCE: 66
gggtttgnca ccgggcctgg c 21

<210> SEQ ID NO 67
<211> LENGTH: 21
<212> TYPE: DNA
<213> ORGANISM: Artificial Sequence
<220> FEATURE:
<223> OTHER INFORMATION: CELTIC core_9 aptamer
<220> FEATURE:
<221> NAME/KEY: misc_feature
<222> LOCATION: (9)..(9)
<223> OTHER INFORMATION: n is a, c, g, or t

<400> SEQUENCE: 67
gggtttggna ccgggcctgg c 21

<210> SEQ ID NO 68
<211> LENGTH: 21
<212> TYPE: DNA

<213> ORGANISM: Artificial Sequence
<220> FEATURE:
<223> OTHER INFORMATION: CELTIC core_10 aptamer
<220> FEATURE:
<221> NAME/KEY: misc_feature
<222> LOCATION: (13)..(13)
<223> OTHER INFORMATION: n is a, c, g, or t

<400> SEQUENCE: 68
gggtttggca ccnggcctgg c 21

<210> SEQ ID NO 69
<211> LENGTH: 21
<212> TYPE: DNA
<213> ORGANISM: Artificial Sequence
<220> FEATURE:
<223> OTHER INFORMATION: CELTIC core_11 aptamer
<220> FEATURE:
<221> NAME/KEY: misc_feature
<222> LOCATION: (15)..(15)
<223> OTHER INFORMATION: n is a, c, g, or t

<400> SEQUENCE: 69
gggtttggca ccggncctgg c 21

<210> SEQ ID NO 70
<211> LENGTH: 21
<212> TYPE: DNA
<213> ORGANISM: Artificial Sequence
<220> FEATURE:
<223> OTHER INFORMATION: CELTIC core_12 aptamer
<220> FEATURE:
<221> NAME/KEY: misc_feature
<222> LOCATION: (16)..(16)
<223> OTHER INFORMATION: n is a, c, g, or t

<400> SEQUENCE: 70
gggtttggca ccgggnctgg c 21

<210> SEQ ID NO 71
<211> LENGTH: 21
<212> TYPE: DNA
<213> ORGANISM: Artificial Sequence
<220> FEATURE:
<223> OTHER INFORMATION: CELTIC core_13 aptamer
<220> FEATURE:
<221> NAME/KEY: misc_feature
<222> LOCATION: (17)..(17)
<223> OTHER INFORMATION: n is a, c, g, or t

<400> SEQUENCE: 71
gggtttggca ccgggcntgg c 21

<210> SEQ ID NO 72
<211> LENGTH: 21
<212> TYPE: DNA
<213> ORGANISM: Artificial Sequence
<220> FEATURE:
<223> OTHER INFORMATION: CELTIC core_14 aptamer
<220> FEATURE:
<221> NAME/KEY: misc_feature
<222> LOCATION: (1)..(1)
<223> OTHER INFORMATION: n is a, c, g, or t

<400> SEQUENCE: 72
nggtttggca tcgggcctgg c 21

<210> SEQ ID NO 73
<211> LENGTH: 21

<212> TYPE: DNA
<213> ORGANISM: Artificial Sequence
<220> FEATURE:
<223> OTHER INFORMATION: CELTIC core_15 aptamer
<220> FEATURE:
<221> NAME/KEY: misc_feature
<222> LOCATION: (2)..(2)
<223> OTHER INFORMATION: n is a, c, g, or t

<400> SEQUENCE: 73
gngtttggca tcgggcctgg c 21

<210> SEQ ID NO 74
<211> LENGTH: 21
<212> TYPE: DNA
<213> ORGANISM: Artificial Sequence
<220> FEATURE:
<223> OTHER INFORMATION: CELTIC core_16 aptamer
<220> FEATURE:
<221> NAME/KEY: misc_feature
<222> LOCATION: (3)..(3)
<223> OTHER INFORMATION: n is a, c, g, or t

<400> SEQUENCE: 74
ggntttggca tcgggcctgg c 21

<210> SEQ ID NO 75
<211> LENGTH: 21
<212> TYPE: DNA
<213> ORGANISM: Artificial Sequence
<220> FEATURE:
<223> OTHER INFORMATION: CELTIC core_17 aptamer
<220> FEATURE:
<221> NAME/KEY: misc_feature
<222> LOCATION: (4)..(4)
<223> OTHER INFORMATION: n is a, c, g, or t

<400> SEQUENCE: 75
gggnttggca tcgggcctgg c 21

<210> SEQ ID NO 76
<211> LENGTH: 21
<212> TYPE: DNA
<213> ORGANISM: Artificial Sequence
<220> FEATURE:
<223> OTHER INFORMATION: CELTIC core_18 aptamer
<220> FEATURE:
<221> NAME/KEY: misc_feature
<222> LOCATION: (5)..(5)
<223> OTHER INFORMATION: n is a, c, g, or t

<400> SEQUENCE: 76
gggtntggca tcgggcctgg c 21

<210> SEQ ID NO 77
<211> LENGTH: 21
<212> TYPE: DNA
<213> ORGANISM: Artificial Sequence
<220> FEATURE:
<223> OTHER INFORMATION: CELTIC core_19 aptamer
<220> FEATURE:
<221> NAME/KEY: misc_feature
<222> LOCATION: (6)..(6)
<223> OTHER INFORMATION: n is a, c, g, or t

<400> SEQUENCE: 77
gggttnggca tcgggcctgg c 21

<210> SEQ ID NO 78

```
<211> LENGTH: 21
<212> TYPE: DNA
<213> ORGANISM: Artificial Sequence
<220> FEATURE:
<223> OTHER INFORMATION: CELTIC core_20 aptamer
<220> FEATURE:
<221> NAME/KEY: misc_feature
<222> LOCATION: (7)..(7)
<223> OTHER INFORMATION: n is a, c, g, or t

<400> SEQUENCE: 78

gggtttngca tcgggcctgg c                                          21


<210> SEQ ID NO 79
<211> LENGTH: 21
<212> TYPE: DNA
<213> ORGANISM: Artificial Sequence
<220> FEATURE:
<223> OTHER INFORMATION: CELTIC core_21 aptamer
<220> FEATURE:
<221> NAME/KEY: misc_feature
<222> LOCATION: (8)..(8)
<223> OTHER INFORMATION: n is a, c, g, or t

<400> SEQUENCE: 79

gggtttgnca tcgggcctgg c                                          21


<210> SEQ ID NO 80
<211> LENGTH: 21
<212> TYPE: DNA
<213> ORGANISM: Artificial Sequence
<220> FEATURE:
<223> OTHER INFORMATION: CELTIC core_22 aptamer
<220> FEATURE:
<221> NAME/KEY: misc_feature
<222> LOCATION: (9)..(9)
<223> OTHER INFORMATION: n is a, c, g, or t

<400> SEQUENCE: 80

gggtttggna tcgggcctgg c                                          21


<210> SEQ ID NO 81
<211> LENGTH: 21
<212> TYPE: DNA
<213> ORGANISM: Artificial Sequence
<220> FEATURE:
<223> OTHER INFORMATION: CELTIC core_23 aptamer
<220> FEATURE:
<221> NAME/KEY: misc_feature
<222> LOCATION: (10)..(10)
<223> OTHER INFORMATION: n is a, c, g, or t

<400> SEQUENCE: 81

gggtttggcn tcgggcctgg c                                          21


<210> SEQ ID NO 82
<211> LENGTH: 21
<212> TYPE: DNA
<213> ORGANISM: Artificial Sequence
<220> FEATURE:
<223> OTHER INFORMATION: CELTIC core_24 aptamer
<220> FEATURE:
<221> NAME/KEY: misc_feature
<222> LOCATION: (11)..(11)
<223> OTHER INFORMATION: n is a, c, g, or t

<400> SEQUENCE: 82

gggtttggca ncgggcctgg c                                          21
```

<210> SEQ ID NO 83
<211> LENGTH: 21
<212> TYPE: DNA
<213> ORGANISM: Artificial Sequence
<220> FEATURE:
<223> OTHER INFORMATION: CELTIC core_25 aptamer
<220> FEATURE:
<221> NAME/KEY: misc_feature
<222> LOCATION: (12)..(12)
<223> OTHER INFORMATION: n is a, c, g, or t

<400> SEQUENCE: 83
gggtttggca tngggcctgg c 21

<210> SEQ ID NO 84
<211> LENGTH: 21
<212> TYPE: DNA
<213> ORGANISM: Artificial Sequence
<220> FEATURE:
<223> OTHER INFORMATION: CELTIC core_26 aptamer
<220> FEATURE:
<221> NAME/KEY: misc_feature
<222> LOCATION: (13)..(13)
<223> OTHER INFORMATION: n is a, c, g, or t

<400> SEQUENCE: 84
gggtttggca tcnggcctgg c 21

<210> SEQ ID NO 85
<211> LENGTH: 21
<212> TYPE: DNA
<213> ORGANISM: Artificial Sequence
<220> FEATURE:
<223> OTHER INFORMATION: CELTIC core_27 aptamer
<220> FEATURE:
<221> NAME/KEY: misc_feature
<222> LOCATION: (14)..(14)
<223> OTHER INFORMATION: n is a, c, g, or t

<400> SEQUENCE: 85
gggtttggca tcgngcctgg c 21

<210> SEQ ID NO 86
<211> LENGTH: 21
<212> TYPE: DNA
<213> ORGANISM: Artificial Sequence
<220> FEATURE:
<223> OTHER INFORMATION: CELTIC core_28 aptamer
<220> FEATURE:
<221> NAME/KEY: misc_feature
<222> LOCATION: (15)..(15)
<223> OTHER INFORMATION: n is a, c, g, or t

<400> SEQUENCE: 86
gggtttggca tcggncctgg c 21

<210> SEQ ID NO 87
<211> LENGTH: 21
<212> TYPE: DNA
<213> ORGANISM: Artificial Sequence
<220> FEATURE:
<223> OTHER INFORMATION: CELTIC core_29 aptamer
<220> FEATURE:
<221> NAME/KEY: misc_feature
<222> LOCATION: (16)..(16)
<223> OTHER INFORMATION: n is a, c, g, or t

<400> SEQUENCE: 87
gggtttggca tcgggnctgg c 21

<210> SEQ ID NO 88
<211> LENGTH: 21
<212> TYPE: DNA
<213> ORGANISM: Artificial Sequence
<220> FEATURE:
<223> OTHER INFORMATION: CELTIC core_30 aptamer
<220> FEATURE:
<221> NAME/KEY: misc_feature
<222> LOCATION: (17)..(17)
<223> OTHER INFORMATION: n is a, c, g, or t

<400> SEQUENCE: 88
gggtttggca tcgggcntgg c 21

<210> SEQ ID NO 89
<211> LENGTH: 21
<212> TYPE: DNA
<213> ORGANISM: Artificial Sequence
<220> FEATURE:
<223> OTHER INFORMATION: CELTIC core_31 aptamer
<220> FEATURE:
<221> NAME/KEY: misc_feature
<222> LOCATION: (18)..(18)
<223> OTHER INFORMATION: n is a, c, g, or t

<400> SEQUENCE: 89
gggtttggca tcgggccngg c 21

<210> SEQ ID NO 90
<211> LENGTH: 21
<212> TYPE: DNA
<213> ORGANISM: Artificial Sequence
<220> FEATURE:
<223> OTHER INFORMATION: CELTIC core_32 aptamer
<220> FEATURE:
<221> NAME/KEY: misc_feature
<222> LOCATION: (19)..(19)
<223> OTHER INFORMATION: n is a, c, g, or t

<400> SEQUENCE: 90
gggtttggca tcgggcctng c 21

<210> SEQ ID NO 91
<211> LENGTH: 21
<212> TYPE: DNA
<213> ORGANISM: Artificial Sequence
<220> FEATURE:
<223> OTHER INFORMATION: CELTIC core_33 aptamer
<220> FEATURE:
<221> NAME/KEY: misc_feature
<222> LOCATION: (20)..(20)
<223> OTHER INFORMATION: n is a, c, g, or t

<400> SEQUENCE: 91
gggtttggca tcgggcctgn c 21

<210> SEQ ID NO 92
<211> LENGTH: 21
<212> TYPE: DNA
<213> ORGANISM: Artificial Sequence
<220> FEATURE:
<223> OTHER INFORMATION: CELTIC core_34 aptamer
<220> FEATURE:
<221> NAME/KEY: misc_feature
<222> LOCATION: (21)..(21)
<223> OTHER INFORMATION: n is a, c, g, or t

<400> SEQUENCE: 92
gggtttggca tcgggcctgg n 21

<210> SEQ ID NO 93
<211> LENGTH: 21
<212> TYPE: DNA
<213> ORGANISM: Artificial Sequence
<220> FEATURE:
<223> OTHER INFORMATION: CELTIC core_35 aptamer

<400> SEQUENCE: 93
gggtttggga tcgggcctgg c 21

<210> SEQ ID NO 94
<211> LENGTH: 21
<212> TYPE: DNA
<213> ORGANISM: Artificial Sequence
<220> FEATURE:
<223> OTHER INFORMATION: CELTIC core_36 aptamer

<400> SEQUENCE: 94
gggtttggca tcgggcctgg g 21

<210> SEQ ID NO 95
<211> LENGTH: 21
<212> TYPE: DNA
<213> ORGANISM: Artificial Sequence
<220> FEATURE:
<223> OTHER INFORMATION: CELTIC core_37 aptamer

<400> SEQUENCE: 95
gggtttggga tcgggcctgg g 21

<210> SEQ ID NO 96
<211> LENGTH: 21
<212> TYPE: DNA
<213> ORGANISM: Artificial Sequence
<220> FEATURE:
<223> OTHER INFORMATION: CELTIC core_38 aptamer

<400> SEQUENCE: 96
gggtttggca tcgggactgg c 21

<210> SEQ ID NO 97
<211> LENGTH: 21
<212> TYPE: DNA
<213> ORGANISM: Artificial Sequence
<220> FEATURE:
<223> OTHER INFORMATION: CELTIC core_39 aptamer

<400> SEQUENCE: 97
gggtttggca tcggggctgg c 21

<210> SEQ ID NO 98
<211> LENGTH: 21
<212> TYPE: DNA
<213> ORGANISM: Artificial Sequence
<220> FEATURE:
<223> OTHER INFORMATION: CELTIC core_40 aptamer

<400> SEQUENCE: 98
gggtttggca tcgggtctgg c 21

<210> SEQ ID NO 99
<211> LENGTH: 20
<212> TYPE: DNA
<213> ORGANISM: Artificial Sequence
<220> FEATURE:

<223> OTHER INFORMATION: CELTIC core_41 aptamer

<400> SEQUENCE: 99
gggtttggca tcgggctggc 20

<210> SEQ ID NO 100
<211> LENGTH: 21
<212> TYPE: DNA
<213> ORGANISM: Artificial Sequence
<220> FEATURE:
<223> OTHER INFORMATION: CELTIC core_42 aptamer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 100
gggtttggca ncgggnctgg c 21

<210> SEQ ID NO 101
<211> LENGTH: 21
<212> TYPE: DNA
<213> ORGANISM: Artificial Sequence
<220> FEATURE:
<223> OTHER INFORMATION: CELTIC core_43 aptamer
<220> FEATURE:
<221> NAME/KEY: misc_feature
<222> LOCATION: (16)..(16)
<223> OTHER INFORMATION: n is a, c, g, or t

<400> SEQUENCE: 101
gggtttggca gcgggnctgg c 21

<210> SEQ ID NO 102
<211> LENGTH: 21
<212> TYPE: DNA
<213> ORGANISM: Artificial Sequence
<220> FEATURE:
<223> OTHER INFORMATION: CELTIC core_44 aptamer
<220> FEATURE:
<221> NAME/KEY: misc_feature
<222> LOCATION: (16)..(16)
<223> OTHER INFORMATION: n is a, c, g, or t

<400> SEQUENCE: 102
gggtttggca acgggnctgg c 21

<210> SEQ ID NO 103
<211> LENGTH: 48
<212> TYPE: RNA
<213> ORGANISM: Artificial Sequence
<220> FEATURE:
<223> OTHER INFORMATION: ARACD3-0010209 aptamer

<400> SEQUENCE: 103
ucuaagcaau auuguuugcu uuugcagcga uucuguuucg auauauua 48

<210> SEQ ID NO 104
<211> LENGTH: 49
<212> TYPE: RNA
<213> ORGANISM: Artificial Sequence
<220> FEATURE:
<223> OTHER INFORMATION: ARACD3-2980001 aptamer

<400> SEQUENCE: 104
uucaagauaa uguaauuauu uuugcagcga uucuuguuuu guucgauuu 49

<210> SEQ ID NO 105
<211> LENGTH: 49
<212> TYPE: RNA
<213> ORGANISM: Artificial Sequence
<220> FEATURE:
<223> OTHER INFORMATION: ARACD3-0270039 aptamer

<400> SEQUENCE: 105
caaaguucaa gauugagcuu uuugcagcga uucuuguuuu aucaaacga 49

<210> SEQ ID NO 106
<211> LENGTH: 48
<212> TYPE: RNA
<213> ORGANISM: Artificial Sequence
<220> FEATURE:
<223> OTHER INFORMATION: ARACD3-3130001 aptamer

<400> SEQUENCE: 106
gaugauaucu uuaauaucaa uugcagcgau ucuuguuuga gaauaaac 48

<210> SEQ ID NO 107
<211> LENGTH: 50
<212> TYPE: RNA
<213> ORGANISM: Artificial Sequence
<220> FEATURE:
<223> OTHER INFORMATION: ARACD3-3700006 aotamer

<400> SEQUENCE: 107
uauagacuuu aaugucucau uuucgcagcg auucuuguuu auuuaacaua 50

<210> SEQ ID NO 108
<211> LENGTH: 17
<212> TYPE: RNA
<213> ORGANISM: Artificial Sequence
<220> FEATURE:
<223> OTHER INFORMATION: Core sequence RNA aptamer
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (14)..(15)
<223> OTHER INFORMATION: n is a, c, g, or u

<400> SEQUENCE: 108
ungcagcgau ucunnuu 17

<210> SEQ ID NO 109
<211> LENGTH: 19
<212> TYPE: DNA
<213> ORGANISM: Artificial Sequence
<220> FEATURE:
<223> OTHER INFORMATION: Consensus-1 aptamer

<400> SEQUENCE: 109
grdtkgsydb hsgghctgg 19

<210> SEQ ID NO 110
<211> LENGTH: 21
<212> TYPE: DNA
<213> ORGANISM: Artificial Sequence
<220> FEATURE:
<223> OTHER INFORMATION: Consensus-2 aptamer

<400> SEQUENCE: 110
gggrttggcr bhggghctgg c 21

<210> SEQ ID NO 111
<211> LENGTH: 21
<212> TYPE: DNA
<213> ORGANISM: Artificial Sequence
<220> FEATURE:
<223> OTHER INFORMATION: Consensus-3 aptamer

<400> SEQUENCE: 111
gdttdgsywb csggmctggs g 21

<210> SEQ ID NO 112
<211> LENGTH: 21
<212> TYPE: DNA
<213> ORGANISM: Artificial Sequence
<220> FEATURE:
<223> OTHER INFORMATION: Consensus-4 aptamer

<400> SEQUENCE: 112
gggtttggca bcgggcctgg c 21

<210> SEQ ID NO 113
<211> LENGTH: 16
<212> TYPE: RNA
<213> ORGANISM: Artificial Sequence
<220> FEATURE:
<223> OTHER INFORMATION: Consensus-5 aptamer
<220> FEATURE:
<221> NAME/KEY: misc_feature
<222> LOCATION: (12)..(12)
<223> OTHER INFORMATION: n is a, c, g, or u

<400> SEQUENCE: 113
gcagcgauuc unguuu 16

<210> SEQ ID NO 114
<211> LENGTH: 86
<212> TYPE: DNA
<213> ORGANISM: Artificial Sequence
<220> FEATURE:
<223> OTHER INFORMATION: DNA aptamer library
<220> FEATURE:
<221> NAME/KEY: misc_feature
<222> LOCATION: (24)..(63)
<223> OTHER INFORMATION: n is a, c, g, or t

<400> SEQUENCE: 114
tagggaagag aaggacatat gatnnnnnnn nnnnnnnnnn nnnnnnnnnn nnnnnnnnnn 60
nnnttgacta gtacatgacc acttga 86

<210> SEQ ID NO 115
<211> LENGTH: 23
<212> TYPE: DNA
<213> ORGANISM: Artificial Sequence
<220> FEATURE:
<223> OTHER INFORMATION: forward primer for DNA SELEX

<400> SEQUENCE: 115
tagggaagag aaggacatat gat 23

<210> SEQ ID NO 116
<211> LENGTH: 23
<212> TYPE: DNA
<213> ORGANISM: Artificial Sequence
<220> FEATURE:
<223> OTHER INFORMATION: reverse primer for DNA SELEX

<400> SEQUENCE: 116
tcaagtggtc atgtactagt caa 23

<210> SEQ ID NO 117
<211> LENGTH: 97
<212> TYPE: DNA
<213> ORGANISM: Artificial Sequence
<220> FEATURE:
<223> OTHER INFORMATION: RNA aptamer library
<220> FEATURE:
<221> NAME/KEY: misc_feature
<222> LOCATION: (24)..(43)
<223> OTHER INFORMATION: n is a, c, g, or t
<220> FEATURE:
<221> NAME/KEY: misc_feature
<222> LOCATION: (65)..(74)
<223> OTHER INFORMATION: n is a, c, g, or t

<400> SEQUENCE: 117
cctctctatg ggcagtcggt gatnnnnnnn nnnnnnnnnn nnntttctgc agcgattctt 60
gtttnnnnnn nnnnggagaa tgaggaaccc agtgcag 97

<210> SEQ ID NO 118
<211> LENGTH: 43
<212> TYPE: DNA
<213> ORGANISM: Artificial Sequence
<220> FEATURE:
<223> OTHER INFORMATION: forward primer for RNA SELEX

<400> SEQUENCE: 118
taatacgact cactataggg cctctctatg ggcagtcggt gat 43

<210> SEQ ID NO 119
<211> LENGTH: 23
<212> TYPE: DNA
<213> ORGANISM: Artificial Sequence
<220> FEATURE:
<223> OTHER INFORMATION: reverse primer for RNA SELEX

<400> SEQUENCE: 119
ctgcactggg ttcctcattc tcc 23

<210> SEQ ID NO 120
<211> LENGTH: 23
<212> TYPE: DNA
<213> ORGANISM: Artificial Sequence
<220> FEATURE:
<223> OTHER INFORMATION: forward blocking sequence for RNA SELEX

<400> SEQUENCE: 120
atcaccgact gcccatagag agg 23

<210> SEQ ID NO 121
<211> LENGTH: 23
<212> TYPE: DNA
<213> ORGANISM: Artificial Sequence
<220> FEATURE:
<223> OTHER INFORMATION: reverse blocking sequence for RNA SELEX

<400> SEQUENCE: 121
ctgcactggg ttcctcattc tcc 23

<210> SEQ ID NO 122

-continued

```
<211> LENGTH: 15
<212> TYPE: DNA
<213> ORGANISM: Artificial Sequence
<220> FEATURE:
<223> OTHER INFORMATION: capture sequence for RNA SELEX

<400> SEQUENCE: 122

caagaatcgc tgcag                                                   15
```

ANTI-CD3 APTAMERS FOR USE IN CELL TARGETING AND LABELING

CROSS-REFERENCE TO RELATED APPLICATIONS

This application claims priority to U.S. Provisional Application No. 62/879,401, filed 26 Jul. 2019; and to U.S. Provisional Application No. 62/879,413, filed 26 Jul. 2019; and to PCT Application No. PCT/IB2019/000890, filed 26 Jul. 2019. Each of the aforementioned applications is hereby incorporated by reference in its entirety.

INCORPORATION BY REFERENCE

The content of the TXT file of the sequence listing named "Sequence-Listing-12267-0503.txt", having a size of 27335 bytes and a creation date of 4 Oct. 2020, and electronically submitted via Patent Center on 25 Jan. 2022, is incorporated herein by reference in its entirety.

BACKGROUND

Cluster of differentiation 3 (CD3) is a protein complex containing one γ subunit, one δ subunit, and two ε subunits, which form CD3γε and CD3δε heterodimers that associate with the T cell receptor (TCR) and transmit an intracellular signal when the TCR binds to a peptide-MHC complex. The CD3 subunits are highly homologous, and each has a small cytoplasmic domain and a transmembrane domain containing negatively charged residues, through which it associates with positively charged residues in the transmembrane region of the TCR. The TCR contains α, β, ζ, and η subunits and exists as αβ heterodimers associated with ζζ homodimers or ζη heterodimers. The TCR in turn is associated with CD3γε and CD3δε heterodimers.

Aptamers are short, single-stranded oligonucleotides with unique three-dimensional configurations. Like antibodies, aptamers bind to targets with high specificity and can often modulate the biological activity of a target. Aptamers offer many advantages relative to antibodies, including lack of immunogenicity, well controlled and inexpensive chemical synthesis, high stability, and good tissue penetration. Aptamers also can be attached to nanoparticles, drugs, imaging agents, and other nucleic acids for use as targeting moieties.

SUMMARY

The present technology provides DNA and RNA aptamers that bind to CD3 and can be used to target, label or sort T cells.

Accordingly, in one aspect, the technology provides an aptamer that binds to CD3 ε/γ or CD3 ε/δ protein complexes. The aptamer comprises a polynucleotide having any of several nucleic acid sequences described herein.

Another aspect of the invention is a method of labeling, purifying, or sorting cells expressing CD3. The cells are incubated with an anti-CD3 aptamer which carries a label, such as a fluorescent label or radioisotope.

Another aspect of the technology is a delivery vehicle for in vitro or in vivo targeting T cells comprising the above anti-CD3 aptamer.

Yet another aspect of the technology is a method of targeting the delivery vehicle to T cells in a subject. The method comprises administering the delivery vehicle to the subject.

Further, the technology provides a pharmaceutical composition comprising the above-described drug delivery vehicle.

The present technology can be further summarized in the following list of features.

1. An aptamer comprising the sequence $GX_1X_2TX_3GX_4X_5X_6X_7X_8X_9GGX_{10}CTGG$, wherein $X_1$ is G or A; $X_2$ and $X_6$ are A, T, or G; $X_3$ is T, or G; $X_4$ and $X_9$ are G or C; $X_5$ is C or T; $X_7$ is T, G, or C; and $X_8$ and $X_{10}$ are C, T, or A (SEQ ID NO:109) or a variant thereof; and wherein the aptamer binds to CD3 ε/γ or CD3 ε/δ.
2. An aptamer comprising the sequence $GGGX_1TTGGCX_2X_3X_4GGGX_5CTGGC$, wherein $X_1$ and $X_2$ are A, T, or G; $X_3$ is T, C, or G; $X_4$ and $X_5$ are A, T, or C (SEQ ID NO:110) or a variant thereof, and wherein the aptamer binds to CD3 ε/γ or CD3 ε/δ.
3. An aptamer comprising the sequence $GX_1TTX_2GX_3X_4X_5X_6CX_7GGX_8CTGGX_9G$, wherein $X_1$ is A or G; $X_2$ is T or G; $X_3$ and $X_7$, $X_9$ are G or C; $X_4$ is T or C; $X_5$ is A or T; $X_6$ is T, C, or G; $X_8$ is A or C (SEQ ID NO:111) or a variant thereof, and wherein the aptamer binds to CD3 ε/γ or CD3 ε/δ.
4. An aptamer comprising the sequence $GGGTTTGGCAX_1CGGGCCTGGC$, wherein $X_1$ is G, C, or T (SEQ ID NO:112) or a variant thereof, and wherein the aptamer binds to CD3 ε/γ or CD3 ε/δ.
5. An aptamer comprising the sequence $GCAGCGAUUCUX_1GUUU$, wherein $X_1$ is U or no base (SEQ ID NO:113) or a variant thereof, and wherein the aptamer binds to CD3 ε/γ or CD3 ε/δ.
6. The aptamer of any of features 1-5, wherein the aptamer binds to human CD3 ε/γ and/or CD3 ε/δ with a dissociation constant of about 0.2 pM to about 250 nM.
7. The aptamer of any of features 1-5, wherein the aptamer binds to a non-human form of CD3 ε/γ and/or CD3 ε/δ with a dissociation constant of about 20 nM to about 800 nM.
8. The aptamer of any of features 1-7 comprising a sequence selected from SEQ ID NOS: 1 to 108.
9. The aptamer of any of features 1-8 comprising a variant of said sequence, wherein one or more of said bases are substituted with a non-naturally occurring base or wherein one or more of said bases is omitted or the corresponding nucleotide is replaced with a linker.
10. The aptamer of feature 9, wherein the one or more non-naturally occurring bases are selected from the group consisting of methylinosine, dihydrouridine, methyl guanosine, and thiouridine.
11. The aptamer of any of features 1-10 that binds to but does not activate CD3+ T cells.
12. A vehicle for delivering an agent, a dye, a functional group for covalent coupling or a biologically active agent to T cells, wherein the vehicle comprises the aptamer of any of features 1-11.
13. The vehicle of feature 11 or feature 12 that comprises a polymeric nanoparticle.
14. The vehicle of feature 13, wherein the polymeric nanoparticle comprises a poly(beta amino ester) (PBAE).
15. The vehicle of feature 13 or feature 14, wherein the aptamer is covalently linked to the polymer.
16. The vehicle of any of features 13-15, wherein the agent is a T cell modulator or an imaging agent.
17. The vehicle of feature 16, wherein the T cell modulator is a viral vector carrying a transgene; wherein the viral vector is coated with the polymer; and wherein the aptamer is covalently linked to the polymer.

18. The vehicle of feature 17, wherein the viral vector is a lentiviral vector.
19. The vehicle of feature 17 or feature 18, wherein the transgene encodes a chimeric antigen receptor.
20. The vehicle of feature 16, wherein the T cell modulator is selected from the group consisting of dasatinib, an MEK1/2 inhibitor, a PI3K inhibitor, an HDAC inhibitor, a kinase inhibitor, a metabolic inhibitor, a GSK3 beta inhibitor, an MAO-B inhibitor, and a Cdk5 inhibitor.
21. A method of delivering an agent to T cells in a subject, the method comprising administering the vehicle of any of features 16-20 to the subject.
22. A pharmaceutical composition comprising the vehicle of any of features 16-20 and one or more excipients.
23. A method of isolating T cells from a subject, the method comprising using the vehicle of any of features 1-12 to isolate T cells from the subject.

BRIEF DESCRIPTION OF THE DRAWINGS

FIG. 1 shows the first 45 nucleic acid sequences (SEQ ID NOS:1-45, from top to bottom) of anti-CD3 DNA aptamers (clusters) obtained by performing SELEX on a mixture of recombinant human CD3 ε/γ and human CD3 ε/δ proteins. Each complex was prepared as a C-terminal Fc fusion. hIgG1 Fc was used as a counter target. The clusters are arranged from top to bottom in the order of decreasing frequency of occurrence in a given round of SELEX.

FIGS. 5A and 5D show binding of CELTIC_2 and CELTIC_2s, respectively, to the cells. FIGS. 5B and 5E show binding of CELTIC_3 and CELTIC_3s, respectively, to the cells. FIGS. 5C and 5F show binding of CELTIC_21 and CELTIC_21s to the cells. Binding of the aptamers to Ramos cells (CD3 negative cells; control) is shown for comparison.

FIG. 6 shows the alignment of the sequences of clusters 1, 2, 3, and 21 (SEQ ID NOS:1, 2, 3, and 21, respectively), and that of clusters 1, 2, and 3 to show the core region of homology. Multiple sequence alignment was performed with ClustalW algorithm. Nucleotides found conserved in each cluster are marked with an *.

FIGS. 9A and 9B are bar graphs showing comparisons of the results of binding of several selected aptamers to Jurkat cells (CD3 positive cells) and Ramos cells (CD3 negative cells; control) at concentrations of 3 nM (FIG. 9A) and 10 nM (FIG. 9B). Anti-CD3 OKT3 monoclonal antibody (32 nM) was included as positive control.

FIGS. 10A-10D show the stability of aptamers CELTIC_1s (FIG. 10A), CELTIC_4 s (FIG. 10B), CELTIC_11s (FIG. 10C) and CELTIC_19s (FIG. 10D) in presence of serum. Integrity of aptamers was determined by agarose gel electrophoresis after incubating the aptamers in serum, in SELEX buffer containing 5% serum or in RPMI medium containing 10% serum for different periods of time (24 h, 4 h, 2 h, 1 h, 30 min, 10 min, or 0 h) at 37° C.

FIGS. 11A and 11B are bar graph showing the stability of aptamers CELTIC_1s, CELTIC_4s, CELTIC_9s, CELTIC_11s, CELTIC_19s and CELTIC_22s in presence of serum. Stability was determined by incubating the aptamers in serum or in SELEX buffer containing 5% serum for different periods of time (24 h, 4 h, 2 h, 1 h, 0.5 h, 10 min, or 0 h) at 37° C., followed by measuring binding of the aptamers to Jurkat cells (CD3 positive cells) by flow cytometry. Anti-CD3 OKT3 monoclonal antibody (32 nM) was included as positive control.

3 nM, 10 nM, 30 nM, 100 nM, and 300 nM. Anti-CD3 OKT3 monoclonal antibody (32 nM) was included as positive control.

FIGS. 13A-13D are bar graphs showing results of binding of aptamers CELTIC_1s, CELTIC_4s, CELTIC_9s and CELTIC_19s obtained by the SELEX procedure (FIG. 1) to mouse CD3-positive EL4 cells to estimate binding saturation and $K_D$. The binding was tested at three concentrations of the aptamers: 3 nM, 10 nM, 30 nM, 100 nM, and 300 nM. For comparison, binding of the aptamers at a concentration of 300 nM and of the anti-CD3 145-2C11 monoclonal antibody (32 nM) to human Jurkat cells is also shown (grey bars).

Figure 14J:
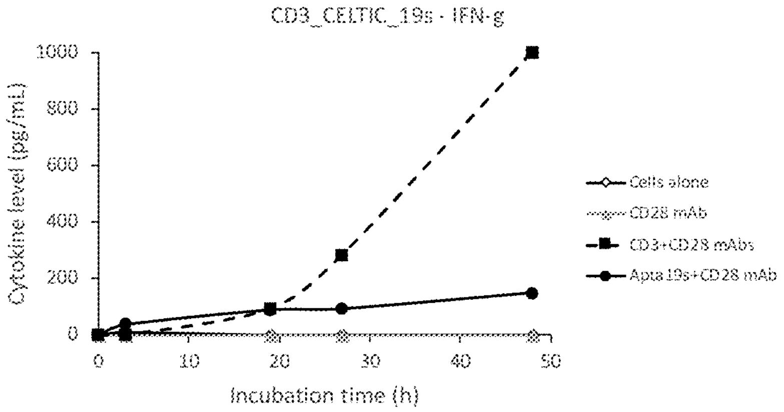
Figure 14K:
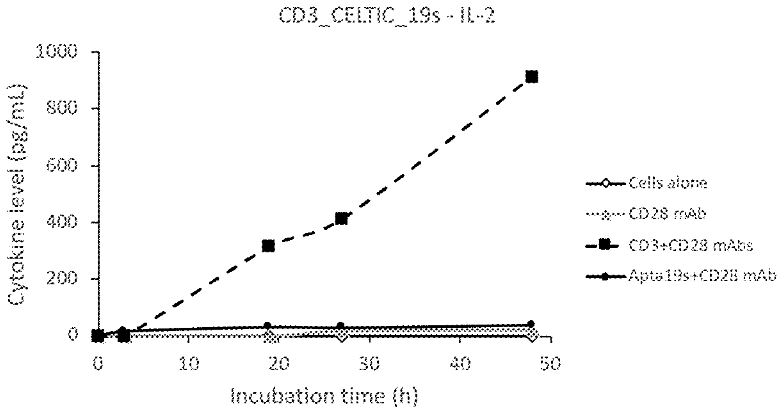
Figure 14L:
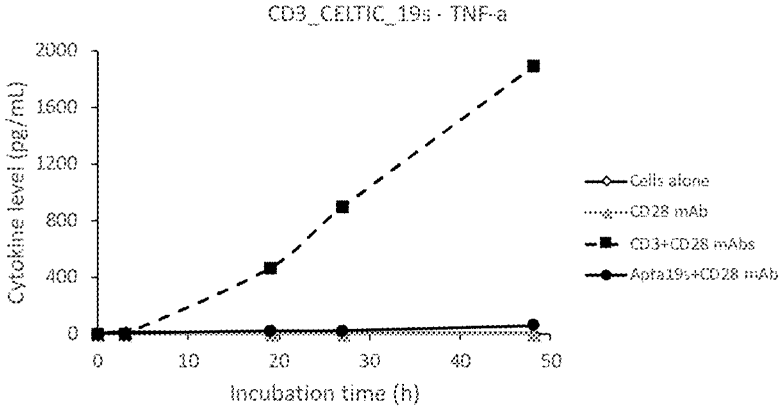

FIGS. 14A-14L are graphs showing activation of human lymphocytes by anti-CD3 DNA aptamers at 1 μm concentration, as measured by secretion of cytokines. Levels of secreted cytokines were determined by ELISA after incubating the aptamers in presence of costimulatory anti-CD28 antibody in RPMI medium containing 10% serum for different periods of time (0 h, 3 h, 19 h, 27 h or 48 h) at 37° C. FIGS. 14A, 14B, and 14C show secretion of IFN-γ, IL-2, and TNF-α, respectively, by the aptamer CELTIC_1s. FIGS. 14D, 14E, and 14F show secretion of IFN-γ, IL-2, and TNF-α, respectively, by the aptamer CELTIC_4s. FIGS. 14G, 14H, and 14I show secretion of IFN-γ, IL-2, and TNF-α, respectively, by the aptamer CELTIC_11s. FIGS. 14I, 14K, and 14L show secretion of IFN-γ, IL-2, and TNF-α, respectively, by the aptamer CELTIC_19s. For comparison, activation of anti-CD3 monoclonal antibody with or without costimulatory anti-CD28 antibody is also shown.

FIGS. 15A-15C are bar graphs showing activation of human lymphocytes by anti-CD3 DNA aptamers at 1 μm concentration, as measured by expression of CD25 and CD69 activation markers. Levels of CD25 and CD69 surface markers on CD4- and CD8-positive T lymphocytes were determined by flow cytometry after incubating the aptamers with or without costimulatory anti-CD28 antibody in RPMI medium containing 10% serum for 48 h at 37° C. FIG. 15A shows expression results obtained with cells treated with CELTIC_1s, CELTIC_4s, CELTIC_11s or CELTIC_19s alone. FIG. 15B shows expression results obtained with cells treated with the same aptamers mixed with costimulatory anti-CD28 antibody. FIG. 15C shows expression results obtained with cells treated with fresh aptamer solutions mixed with anti-CD28 antibody added to culture medium after 3 h, 19 h and 27 h incubation in order to keep the concentration of reagents constant.

FIGS. 16A-16C are bar graphs showing activation of human lymphocytes by anti-CD3 DNA aptamers at 1 μm concentration, as measured by secretion of cytokines. Levels of secreted cytokines were determined with Human Th1/Th2 Cytometric Bead Array after incubating the aptamers in presence of costimulatory anti-CD28 antibody in RPMI medium containing 10% serum for 48 h at 37° C. FIG. 16A shows secretion of IFN-γ, IL-2, IL-4, IL-5, IL-10 and TNF-α for cells treated with CELTIC_1s, CELTIC_4s, CELTIC_11s or CELTIC_19s alone. FIG. 16B shows cytokine secretion profile of cells treated with the same aptamers mixed with costimulatory anti-CD28 antibody. FIG. 16C shows cytokine secretion profile of cells treated with fresh aptamer solutions mixed with anti-CD28 antibody added to culture medium after 3 h, 19 h and 27 h incubation in order to keep the concentration of reagents constant.

FIGS. 17.1A-17.3B are bar graphs showing results of binding of aptamers CELTIC_1s, CELTIC_4s, CELTIC_11s and CELTIC_19s obtained by the SELEX procedure (FIG. 1) and antibodies specific for CD3 epitopes to Jurkat cells (CD3 positive cells) in order to map regions of CD3 recognized by aptamers. The binding was performed in presence of saturating concentrations of competitors. In FIGS. 17.1A, 17.2A and 17.3A binding of PE-labeled monoclonal OKT3, UCHT1 and HIT3a antibodies specific for CD3 was tested at one concentration (0.1 nM for OKT3 and HIT3a or 1 nM for UCHT1) and in absence or in presence of saturating concentrations of unlabeled antibodies (32 nM for OKT3 and HIT3a or 10 nM for UCHT1) or biotinylated aptamers (300 nM). In FIGS. 17.1B, 17.2B and 17.3B binding of biotinylated aptamers was tested at a concentration of 300 nM in absence or in presence of saturating concentrations of unlabeled antibodies (32 nM for OKT3 and HIT3a or 10 nM for UCHT1) and in presence of PE labeled streptavidin.

FIG. 17.4 is a bar graph showing results of binding of aptamer CELTIC_core corresponding to the computed conserved motif found among top 45 sequence families isolated during SELEX (FIG. 7C) to Jurkat cells (CD3 positive cells). For comparison, binding of the aptamer to Ramos cells (CD3 negative cells; control) is also shown. The binding was tested at the following aptamer concentrations: 3 nM, 5 nM, 10 nM, 20 nM, 30 nM, 40 nM, 50 nM 75 nM and 100 nM. Anti-CD3 OKT3 monoclonal antibody (32 nM) was included as positive control.

Figure 7A:
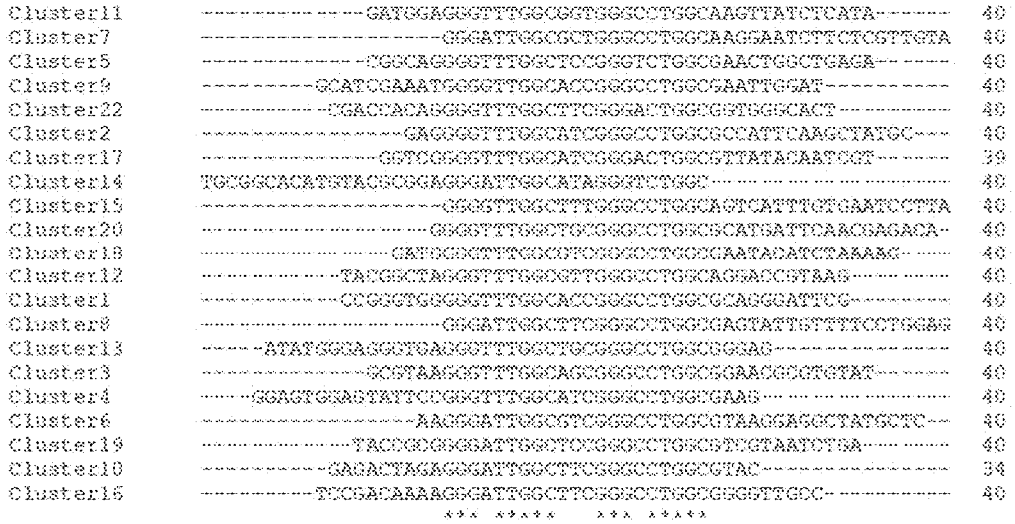
FIGS. 7A and 7B show DNA sequences of several additional clusters (SEQ ID NOS:11, 7, 5, 9, 22, 2, 17, 14, 15, 20, 18, 12, 1, 8, 13, 3, 4, 6, 19, 10, and 16 from top to bottom of FIG. 7A, SEQ ID NOS:1-22 from top to bottom of FIG. 7B) obtained by the SELEX procedure (FIG. 1) and an alignment of the sequences excluding and including the sequence of cluster 21 (FIG. 7A and FIG. 7B, respectively). Multiple sequence alignments were performed with ClustalW algorithm. Nucleotides found conserved in each cluster are marked with an *.
Figure 7B:
Figure 7C:
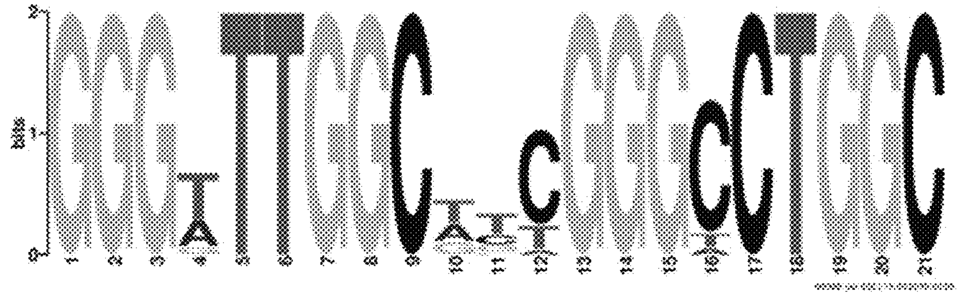
FIG. 7C shows the core sequence (SEQ ID NO:57) and base distribution identified by MEME (Multiple Em for Motif Elicitation) among the first 45 clusters obtained by the SELEX procedure (FIG. 1).
Figures 8A, 8B, 8C, 8D, 8E, 8F:
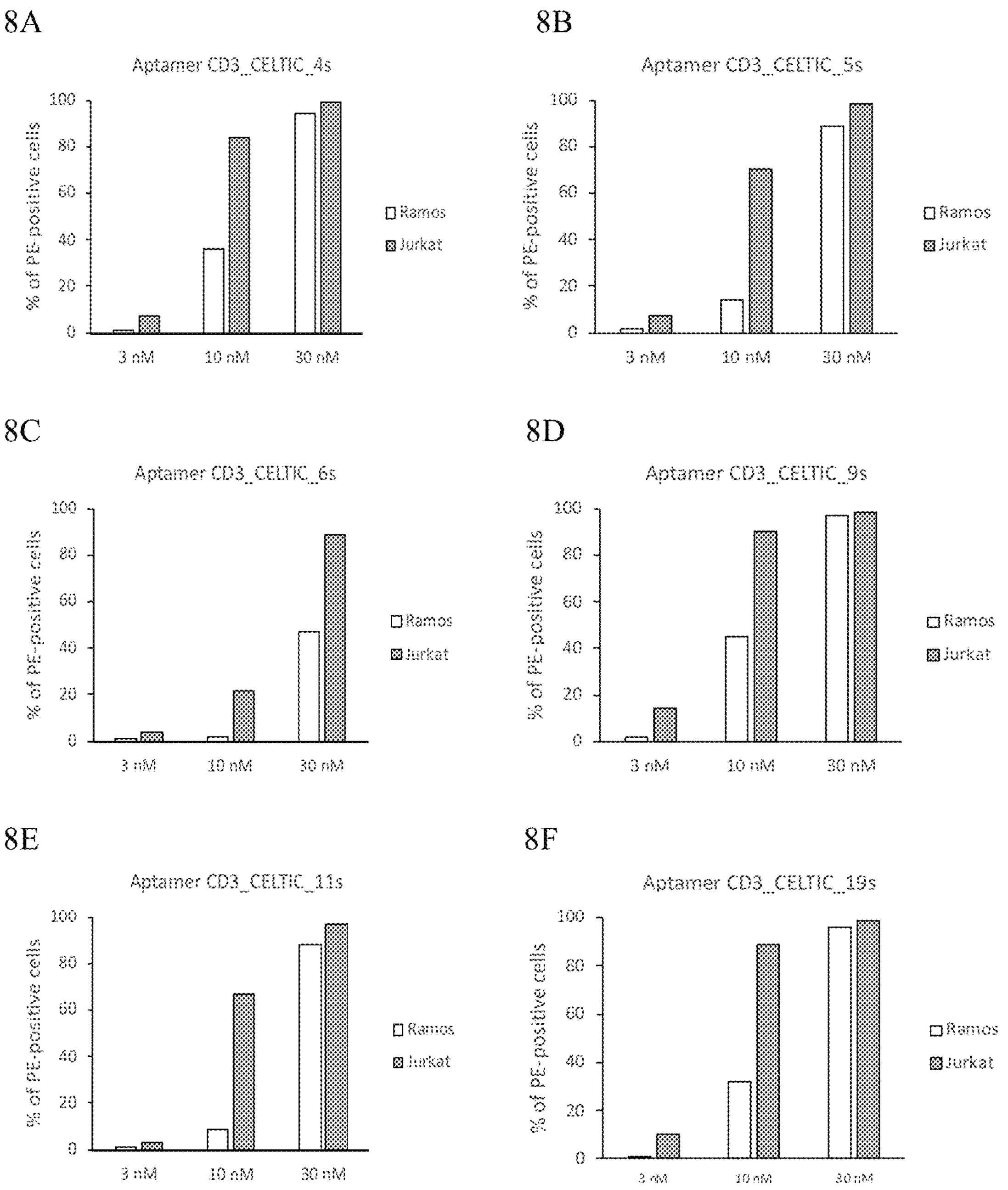
FIGS. 8A-8G are bar graphs showing results of binding of aptamers (without the 5' and 3' flanking regions) CELTIC_4s (SEQ ID NO:50), CELTIC_5s (SEQ ID NO:51), CELTIC_6s (SEQ ID NO:52), CELTIC_9s (SEQ ID NO:53), CELTIC_11s (SEQ ID NO:54), CELTIC_19s (SEQ ID NO:55), and CELTIC_22s (SEQ ID NO:56), obtained by the SELEX procedure (FIG. 1) to Jurkat cells (CD3 positive cells) to estimate binding saturation and $K_D$. The binding was tested at three concentrations of the aptamers: 3 nM, 10 nM, and 30 nM. For comparison, binding of the aptamers to the Ramos cells (CD3 negative cells; control) is also shown.
Figure 8G:
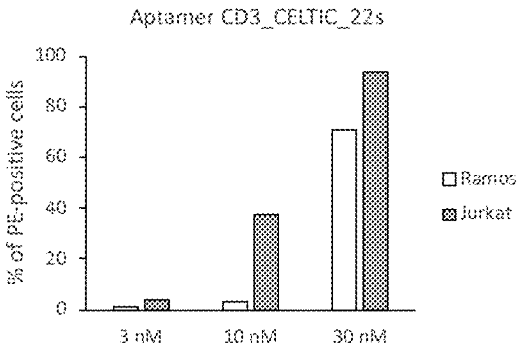

FIG. 17.5 lists the sequences of the different variants (1 to 13) (SEQ ID NOS:58-71, respectively) of aptamer CELTIC_core (top sequence, SEQ ID NO:57) corresponding to the computed conserved motif found among top 45 sequence families isolated during SELEX (FIG. 7C). Underscore refers to positions in the sequence where the base has been replaced by a C3 spacer therefore creating an abasic site. Mutations introduced in the original core sequence are highlighted in bold.

FIGS. 176A-17.6N are bar graphs showing results of binding of aptamers CELTIC_core1, CELTIC_core2, CELTIC_core3, CELTIC_core4, CELTIC_core5, CELTIC_core6, CELTIC_core7, CELTIC_core8, CELTIC_core9, CELTIC_core10, CELTIC_core11, CELTIC_core12, CELTIC_core13 and CELTIC_coreT carrying modifications compared to CELTIC_core (FIG. 17.5) to Jurkat cells (CD3 positive cells). The binding was tested at the two aptamer concentrations (50 nM and 100 nM) and compared to cell staining obtained with CELTIC_core (50 and 100 nM) and full length CD3_CELTIC_1s (10 and 50 nM). For comparison, binding of the aptamers to Ramos cells (CD3 negative cells; control) is also shown. Anti-CD3 OKT3 monoclonal antibody (32 nM) was included as positive control.

FIG. 18 lists the sequences of the different variants (1 to 44, SEQ ID NOS:58-102, including the 13 mutants already described in FIG. 17.5 and evaluated in FIGS. 17.6A to 17.6N) of aptamer CELTIC_core ("0", SEQ ID NO:57) corresponding to the computed conserved motif found among top 45 sequence families obtained during SELEX (FIG. 7C). Underscore refers to positions in the sequence where the base has been replaced by a C3 spacer therefore creating an abasic site. Mutations introduced in the original core sequence are highlighted in bold.

FIGS. 19A-19D are bar graphs showing results of binding of aptamers CELTIC_core14 to CELTIC_core44 carrying modifications compared to CELTIC_core (FIG. 17.5) to Jurkat cells (CD3 positive cells). The binding was tested at the two aptamer concentrations: 50 nM (FIG. 19.A for mutants 14 to 37 and 19.0 for mutants 38 to 44) and 100 nM (FIG. 19.B for mutants 14 to 37 and 19.D for mutants 38 to 44) and compared to cell staining obtained with CELTIC_core (50 and 100 nM) and full length CD3_CELTIC_1s and CD3 CELTIC_19s (10 and 50 nM). For comparison, binding of the aptamers to Ramos cells (CD3 negative cells; control) is also shown. Anti-CD3 OKT3 and anti-CD19 monoclonal antibodies (32 nM each) were included as positive controls.

FIG. 20 summarizes the results of binding of aptamers CELTIC_core1 to CELTIC_core44 (SEQ ID NOS:58-102) carrying above-described modifications compared to CELTIC_core (SEQ ID NO:57) (FIG. 17.5) to Jurkat cells (CD3 positive cells).

FIGS. 21A-21F are bar graphs showing results of binding of aptamers CELTIC_core12, CELTIC_core40HEGt, CELTIC_core42HEGt to Jurkat cells (CD3 positive cells) and antibodies specific for CD3 epitopes in presence of saturating concentrations of competitors in order to map regions of CD3 recognized by aptamers. In FIGS. 21A, 21C and 21E. a binding of PE-labeled monoclonal OKT3, UCHT1 and HIT3a antibodies specific for CD3 was tested at one concentration (0.1 nM for OKT3 and HIT3a or 1 nM for UCHT1) and in absence or in presence of saturating concentrations ofunlabeled antibodies (32 nM for OKT3 and HIT3a or 10 nM for UCHT1) or biotinylated aptamers (300 nM). In FIGS. 21.B 21.D and 21.F binding of biotinylated aptamers was tested at a concentration of 300 nM in absence or in presence of saturating concentrations of unlabeled antibodies (32 nM for OKT3 and HIT3a or 10 nM for UCHT1) and in presence of PE labeled streptavidin. The results are compared with cell staining obtained with full length CD3_CELTIC_1s.

FIGS. 22A-22F show the stability of aptamers CELTIC_coreHEG (FIG. 22A), CELTIC_core12 (FIG. 22B), CELTIC_core24HEG (FIG. 22C), CELTIC_core29HEG (FIG. 22D), CELTIC_core40HEG (FIG. 22E) and CELTIC_core42HEG (FIG. 22F) in presence of serum. Integrity of aptamers was determined by agarose gel electrophoresis after incubating the aptamers in serum, in SELEX buffer containing 5% serum or in RPMI medium containing 10% serum for different periods of time (24 h, 4 h, 2 h, 1 h, 30 min, 10 min, or 0 h) at 37° C.

Figure 23C:
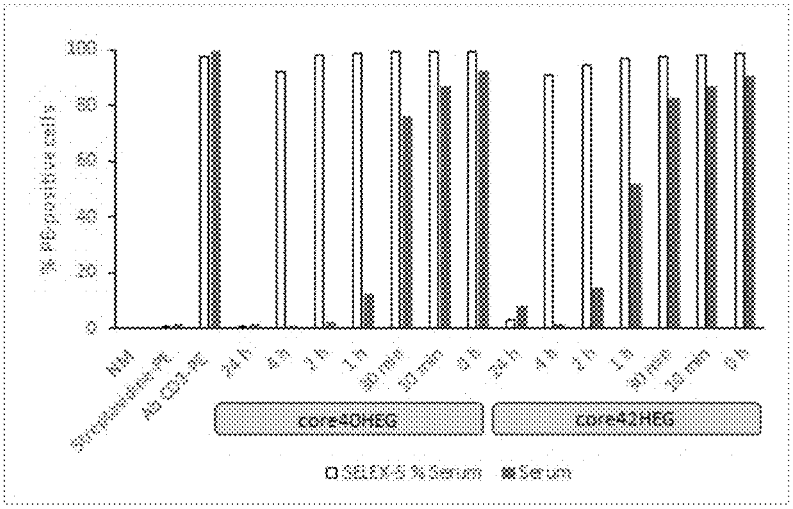

FIGS. 23A-C are bar graph showing the stability of aptamers CELTIC_coreHEG, CELTIC_core12 (FIG. 23A), CELTIC_core24HEG, CELTIC_core29HEG (FIG. 23B), CELTIC_core40HEG and CELTIC_core42HEG (FIG. 23C) in presence of serum. Stability was determined by incubating the aptamers in serum or in SELEX buffer containing 5% serum for different periods of time (24 h, 4 h, 2 h, 1 h, 0.5 h, 10 min, or 0 h) at 37° C., followed by measuring binding of the aptamers to Jurkat cells (CD3 positive cells) by flow cytometry. Anti-CD3 OKT3 monoclonal antibody (32 nM) was included as positive control.

FIGS. 24A-D show the stability of aptamers CELTIC_core40HEG (FIG. 24A), CELTIC_core40HEGt (FIG. 24B), CELTIC_core42HEG (FIG. 24C) and CELTIC_core42HEGt (FIG. 24D) in presence of serum. Integrity of aptamers was determined by agarose gel electrophoresis after incubating the aptamers in serum, in SELEX buffer containing 5% serum or in RPMI medium containing 10% serum for different periods of time (24 h, 4 h, 2 h, 1 h, 30 min, 10 min, or 0 h) at 37° C.

FIGS. 25A-25B are bar graphs showing the stability of aptamers CELTIC_core40HEG, CELTIC_core40HEGt (FIG. 25A), CELTIC_core42HEG and CELTIC_core42HEGt (FIG. 25B) in presence of serum. Stability was determined by incubating the aptamers in serum or in SELEX buffer containing 5% serum for different periods of time (24 h, 4 h, 2 h, 1 h, 0.5 h, 10 min, or 0 h) at 37° C., followed by measuring binding of the aptamers to Jurkat cells (CD3 positive cells) by flow cytometry. Anti-CD3 OKT3 monoclonal antibody (32 nM) was included as positive control.

Figure 26:
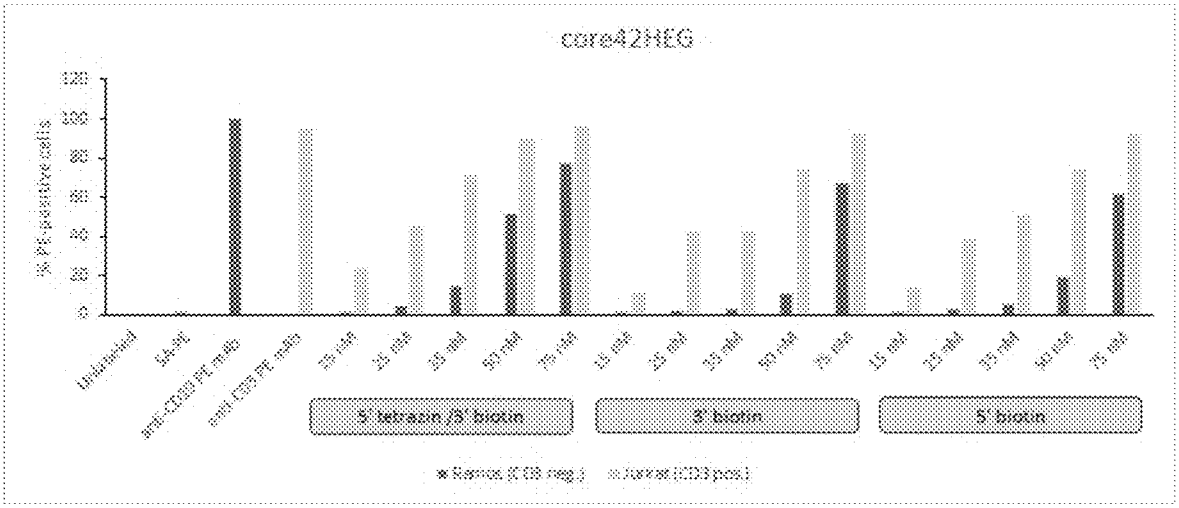

FIG. 26 is a bar graph showing results of binding of aptamer CELTIC_core42HEG carrying chemical modifications on extremities: tetrazin group at the 5' end and biotin at the 3' end to Jurkat cells (CD3 positive cells). The binding was tested at the aptamer concentrations: 15 nM, 25 nM, 35 nM, 50 nM and 75 nM and compared to cell staining obtained with aptamer CELTIC_core42HEG modified with biotin at the 3' or 5' end. For comparison, binding of the aptamers to Ramos cells (CD3 negative cells; control) is also shown. Anti-CD3 OKT3 and anti-CD19 monoclonal antibodies (32 nM each) were included as positive controls.

FIG. 27 shows the alignment of nucleic acid sequences (SEQ ID NOS:103-107, top to bottom) of the five most frequent nucleic acid sequences of anti-CD3 RNA aptamers (clusters) obtained by SELEX performed on a mixture of recombinant CD3 6/7 and CD3 do proteins, each prepared as a C-terminal Fc fusion. hIgG1 Fc was used as the counter target. The last three rounds of this SELEX were performed on Jurkat (CD3 positive) cells as target and Ramos (CD3 negative) cells as counter target. Multiple sequence alignment was performed with ClustalW algorithm. Nucleotides found conserved in each cluster is marked with an *.

Figure 28:
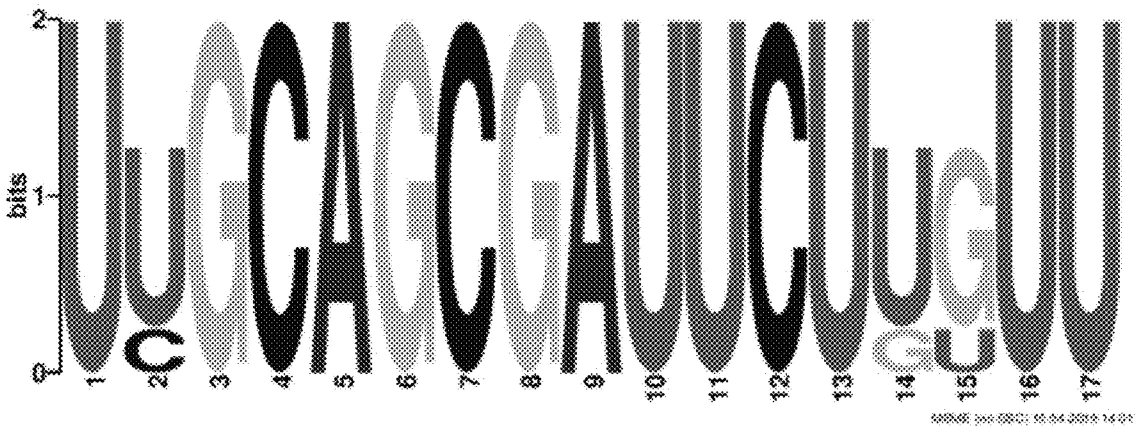

FIG. 28 shows the core sequence (SEQ ID NO:108) and base distribution identified by MEME (Multiple Em for Motif Elicitation) among the first 5 clusters obtained by the SELEX procedure (FIG. 27).

FIGS. 29A-29B shows sequence and Mfold predicted secondary structure of ARACD3-0010209 (SEQ ID NO:103), ARACD3-0270039 (SEQ ID NO:105), ARACD3-2980001 (SEQ ID NO:104), ARACD3-3130001 (SEQ ID NO:106) and ARACD3-3700006 (SEQ ID NO:107). Numbering indicates base numbers of aptamers lacking the flanking region nucleotides. Secondary structure of the core sequence found in the 5 clusters obtained by the SELEX is also depicted. The secondary structure and free energy for each aptamer was computed by Quikfold 3.0 (Zuker et al. 2003) at 37° C., 1 M Nat.

FIGS. 30A-30E are bar graphs showing results of binding of aptamers ARACD3-0010209, ARACD3-0270039, ARACD3-2980001, ARACD3-3130001 and ARACD3-3700006 obtained by the SELEX (FIG. 27) to Jurkat cells (CD3 positive cells). For comparison, binding of the aptamers to Ramos cells (CD3 negative cells; control) is also shown. The binding was tested at three concentrations of the aptamers: 30 nM, 100 nM, and 300 nM.

FIGS. 31A-31C are sensorgrams showing results of binding of biotinylated aptamers ARACD3-3700006, ARACD3-0010209, and ARACD3-3130001 immobilized on a Series Sensor SA Chip to CD3 ε/γ (left column), CD3 ε/δ (middle column), and control hIgG1 Fc (right column). Binding was measured by surface plasmon resonance using a single cycle kinetic protocol. Serial injections of aptamer at concentrations of 3 nM, 10 nM, 30 nM, 100 nM, and 300 nM were performed.

FIGS. 32A-32C show the stability and integrity of the anti-CD3 RNA aptamers ARACD3-3700006 and ARACD3-0010209 in the presence of serum. In FIG. 32A (graph bars) stability was determined by incubating the aptamers in serum or in DPBS containing 5% serum for different periods of time (24 h, 4 h, 2 h, 1 h, 30 min, 10 min, or 0 h) at 37° C., followed by measuring binding of aptamers to Jurkat cells (CD3 positive cells) by flow cytometry. FIGS. 32 B-C show the integrity of aptamers determined by agarose gel electrophoresis after incubating the aptamers in serum, in DPBS buffer containing 5% serum or in RPMI medium containing 10% serum for different periods of time (24 h, 4 h, 2 h, 1 h, 30 min, 10 min, or 0 h) at 37° C.

Figure 33:
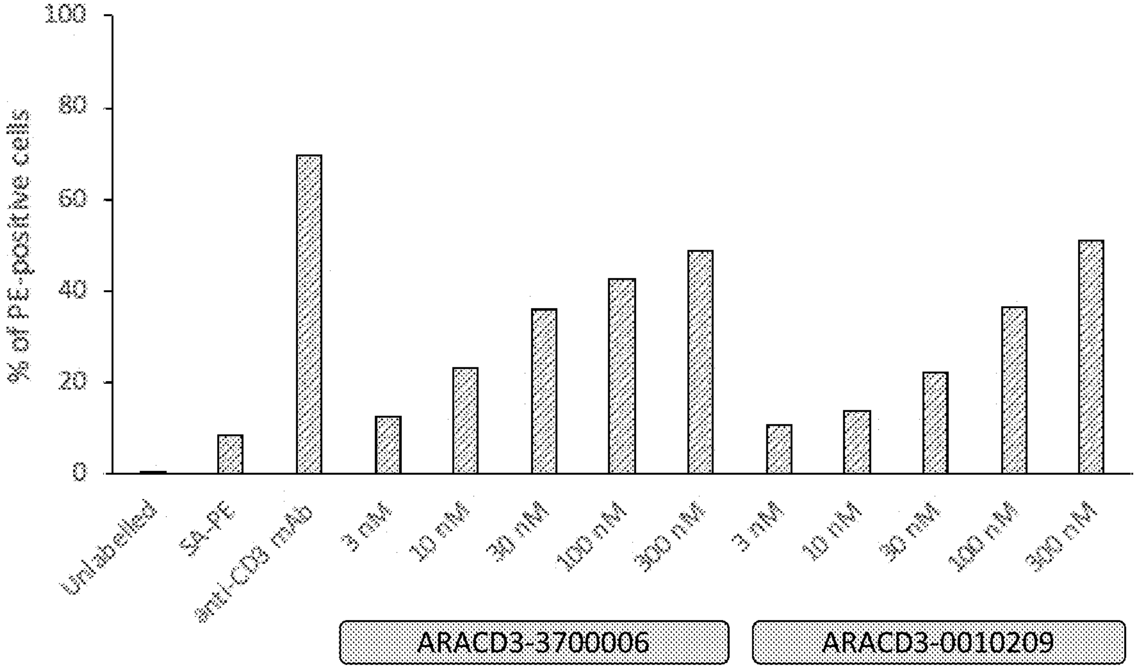

FIG. 33 shows results of binding of aptamers ARACD3-3700006 and ARACD3-0010209 obtained by the SELEX procedure (FIG. 27) to peripheral blood mononuclear cells isolated from healthy donors. The binding was tested at the following aptamer concentrations: 3 nM, 10 nM, 30 nM, 100 nM, and 300 nM.

FIGS. 34A-34B are bar graphs showing results of binding of aptamers ARACD3-3700006 and ARACD3-0010209 obtained by the SELEX (FIG. 27) to mouse CD3-positive EL4 cells to estimate binding saturation and $K_D$. The binding was tested at the following aptamer concentrations: 3 nM, 10 nM, 30 nM, 100 nM, and 300 nM. For comparison, binding of the aptamers at a concentration of 300 nM to human Jurkat cells is also shown.

FIGS. 35A-35F are graphs showing activation of lymphocytes by anti-CD3 RNA aptamers at 1 μm concentration, as measured by secretion of cytokines. Levels of secreted cytokines was determined by ELISA after incubating the aptamers in the presence of costimulatory anti-CD28 antibody in RPMI medium containing 10% serum for different periods of time (0 h, 16 h, 24 h or 48 h) at 37° C. FIGS. 35A, 35B, and 35C show secretion of IFN-γ, IL-2, and TNF-α, respectively, by the aptamer ARACD3-3700006. FIGS. 35D, 35E, and 35F show secretion of IFNγ, IL-2, and TNF-α, respectively, by the aptamer ARACD3-0010209. For comparison, activation of anti-CD3 monoclonal antibody with or without costimulatory anti-CD28 antibody is also shown.

FIGS. 36A-36C are bar graphs showing activation of human lymphocytes by anti-CD3 RNA aptamers at 1 μm concentration, as measured by expression of CD25 and CD69 activation markers. Levels of CD25 and CD69 surface markers on CD4- and CD8-positive T lymphocytes were determined by flow cytometry after incubating the aptamers with or without costimulatory anti-CD28 antibody in RPMI medium containing 10% serum for 48 h at 37° C. FIG. 36A shows expression results obtained with cells treated with ARACD3-3700006 or ARACD3-0010209 alone. FIG. 36B shows expression results obtained with cells treated with the same aptamers mixed with costimulatory anti-CD28 antibody. FIG. 36C shows expression results obtained with cells treated with fresh aptamer solutions mixed with anti-CD28 antibody added to culture medium after 3 h, 19 h and 27 h incubation in order to keep the concentration of reagents constant.

FIGS. 37A-37C are bar graphs showing activation of human lymphocytes by anti-CD3 RNA aptamers at 1 μm concentration, as measured by secretion of cytokines. Levels of secreted cytokines were determined with Human Th1/Th2 Cytometric Bead Array after incubating the aptamers in presence of costimulatory anti-CD28 antibody in RPMI medium containing 10% serum for 48 h at 37° C. FIG. 37A shows secretion of IFN-γ, IL-2, IL-4, IL-5, IL-10 and TNF-α for cells treated with ARACD3-3700006 or ARACD3-0010209 alone. FIG. 37B shows cytokine secretion profile of cells treated with the same aptamers mixed with costimulatory anti-CD28 antibody. FIG. 37C shows cytokine secretion profile of cells treated with fresh aptamer solutions mixed with anti-CD28 antibody added to culture medium after 3 h, 19 h and 27 h incubation in order to keep the concentration of reagents constant.

FIGS. 38A-38F are bar graphs showing results of binding of aptamers ARACD3-3700006 and ARACD3-0010209 obtained by the SELEX procedure (FIG. 27) to Jurkat cells (CD3 positive cells) and antibodies specific for CD3 epitopes in presence of saturating concentrations of competitors in order to map regions of CD3 recognized by aptamers. In FIGS. 38A, 38C and 38E binding of PE-labeled monoclonal OKT3, UCHT1 and HIT3a antibodies specific for CD3 was tested at one concentration (0.1 nM for OKT3 and HIT3a or 1 nM for UCHT1) and in absence or in presence of saturating concentrations of unlabeled antibodies (32 nM for OKT3 and HIT3a or 10 nM for UCHT1) or biotinylated aptamers (300 nM). In FIGS. 38B, 38D and 38F binding of biotinylated aptamers was tested at a concentration of 300 nM in absence or in presence of saturating concentrations of unlabeled antibodies (32 nM for OKT3 and HIT3a or 10 nM for UCHT1) and in presence of PE labeled streptavidin.

DETAILED DESCRIPTION

The present technology relates to anti-CD3 aptamers. Methods for isolating CD3-specific aptamers are disclosed, as well as various uses of the anti-CD3 aptamers including as targeting moieties for delivery vehicles for therapeutic agents directed to T cells and as components of pharmaceutical compositions.

Embodiments of the anti-CD3 aptamers of the present technology can be described using several consensus sequences. DNA aptamers can include the following consensus sequences or variants thereof:

1.

(SEQ ID NO: 109)

$GX_1X_2TX_3GX_4X_5X_6X_7X_8X_9GGX_{10}CTGG$, wherein $X_1$ is G or A; $X_2$ and $X_6$ are A, T, or G; $X_3$ is T, or G; $X_4$ and $X_9$ are G or C; $X_5$ is C or T; $X_7$ is T, G, or C; and $X_8$ and $X_{10}$ are C, T, or A.

2.

(SEQ ID NO: 110)

$GGGX_1TTGGCX_2X_3X_4GGGX_5CTGGC$, wherein $X_1$ and $X_2$ are A, T, or G; $X_3$ is T, C, or G; $X_4$ and $X_5$ are A, T, or C.

3.

(SEQ ID NO: 111)

$GX_1TTX_2GX_3X_4X_5X_6CX_7GGX_8CTGGX_9G$, wherein $X_1$ is A or G; $X_2$ is T or G; $X_3$ and $X_7$, $X_9$ are G or C; $X_4$ is T or C; $X_5$ is A or T; $X_6$ is T, C, or G; $X_8$ is A or C.

4.

(SEQ ID NO: 112)

$GGGTTTGGCAX_1CGGGCCTGGCG$, wherein $X_1$ is G, C, or T.

5.

(SEQ ID NO: 113)

$GCAGCGAUUCUX_1GUUU$, wherein $X_1$ is U or no base.

Aptamers are DNA and RNA oligonucleotides having secondary and tertiary structures that impart high affinity and specific binding to a target molecule. Generation of aptamers using molecule capture technologies is known (see A. D. Ellington and J. W. Szostak. Nature 346: 818-822, 1990; and C. Tuerk and L. Gold. Science 249: 505-510, 1990). Aptamers can be used as targeting devices for delivery of molecular agents to specific target sites. Certain tumors are associated with specific antigens based on which tumor-binding aptamers may be designed to aid tumor targeting for diagnostic or therapeutic purposes.

Generally, aptamers are identified and isolated from pools of nucleic acid sequences using known methods. A pool of nucleic acid sequences is incubated with a target molecule, bound oligonucleotides are selected and, in the next step, amplified, e.g., by polymerase chain reaction (PCR). The product is further purified using affinity column composed of target molecules. The aptamer can comprise DNA, RNA or PNA, and the bases can be natural as well as non-natural. Natural bases are adenine (A), guanine (G), cytosine (C), thymine (T), inosine (I), and uracil (U). Non-naturally occurring bases include, for example, methylinosine, dihydrouridine, methylguanosine, thiouridine, 2'-O-Methyl purines, 2'-fluoro pyrimidines and many others well known to those of ordinary skill in the art. PNA bases can include natural or non-natural bases attached to an amide (peptide-like backbone). The backbone of nucleic acid sequence can be an amide such as PNA, or a phosphodiester such as in DNA or RNA, a thiophosphodiester, a phosphorothioate, a methylene phosphorothioate, or a modification of these chemical structures.

The nucleic acid sequence of the aptamer can comprise only the target-binding sequences which can include both a constant and a variable region or only a variable region. Constant region sequences can be used to facilitate binding, amplification, replication or cleavage of the sequence.

Aptamers can be coupled to agents that are delivered to the target or target site for various purposes, e.g., detection, imaging, diagnostic, therapeutic, or prophylactic. The agents include cells, nanoparticles, hormones, vaccines, haptens, toxins, enzymes, immune system modulators, anti-oxidants, vitamins, functional agents of the hematopoietic system, proteins, such as streptavidin or avidin or mutations thereof, metals and other inorganic substances, virus particles, antigens such as amino acids, peptides, saccharides and polysaccharides, receptors, paramagnetic and fluorescent labels, pharmaceutical compounds, radioisotopes and radionuclides such as is 93P, 95mTc, 99Tm, 186Re, 188Re, 189Re, 111In, 14C, 32P, 3H, 60C, 125I, 35S, 65Zn, 124I and 226Ra, and stable isotopes such as 3He, 6Li, 10B, 113Cd, 135Xe, 149Sm, 151Eu, 155Gd, 174Hf, 199Hg, 235U, 241Pu, and 242Am.

Pharmaceutical compounds that can be coupled to aptamers include, for example, conventional chemotherapeutic agents, antibiotics, corticosteroids, mutagens (e.g., nitroureas), antimetabolites, and hormonal antagonists.

Macromolecules that can be coupled to an aptamer include mitogens, cytokines, and growth factors. Potentially useful cytokines include tumor necrosis factor (TNF), the interleukins (IL-1, IL-2, IL-3, etc.), the interferon proteins, IFN IFN-α, INF-β, and IFN-M, hormones including glucocorticoid hormones, cytosine arabinoside, and anti-virals such as acyclovir and gancyclovir.

An aptamer can be coupled to an agent using well-known methods, including chemical and biological techniques. Both covalent and non-covalent bonds can be created (C.-P. D. Tu et al., Gene 10:177-83, 1980; A. S. Boutorine et al., Anal. Biochem. Bioconj. Chem. 1:350-56, 1990; S. L. Commerford Biochem, 10:1993-99, 1971; D. J. Hnatowich et al., J. Nucl. Med. 36:2306-14, 1995). Covalent bonds can be formed using, for example, chemical conjugation reactions, chelators, or bonds formed from phosphodiester linkages. Non-covalent bonds include molecular interactions such as those between streptavidin and biotin, hydrogen-bonding, and other forms of ionic interaction. Exemplary chelators include DTPA, SHNH and multidentate chelators such as N2S2 and N3S (A. R. Fritzberg et al., J. Nucl. Med. 23:592-98, 1982). Aptamers may also be bound to the cell surface or to a nanoparticle to guide the cell or the nanoparticle to a specific location in vitro or in vivo.

Aptamers are selected using an approach called the selective evolution of ligands by exponential enrichment (SELEX) process (Ellington et al., 1990; Tuerk et al., 1990). SELEX is a method for screening very large combinatorial libraries of oligonucleotides by a repetitive process of in vitro selection and amplification. The method involves selection from a mixture of candidates and stepwise iterations of structural improvement, using the same general selection theme, to achieve virtually any desired criterion of binding affinity and selectivity. Starting from a mixture of nucleic acids, preferably comprising a segment of randomized sequence, the method includes steps of contacting the mixture with the target under conditions favorable for binding, partitioning (i.e., separating) unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

SELEX is based on the insight that within a nucleic acid mixture containing a large number of possible sequences and structures there is a wide range of binding affinities for a given target. A nucleic acid mixture comprising, for example a 20-nucleotide randomized segment can have 420 candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The iterative selection/amplification method is sensitive enough to allow isolation of a single sequence variant in a mixture containing at least 65,000 sequence variants. The method is even capable of isolating a small number of high affinity sequences in a mixture containing $10^{14}$ sequences. The method could, in principle, be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain sub portions of conserved sequence incorporated with randomized sequence. Sequence variation in test nucleic acids can be introduced or increased by mutagenesis before or during the selection/amplification iterations.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family, which will allow the determination of a comprehensive description of the nucleic acid ligand solution.

After a description of the nucleic acid ligand family has been resolved by SELEX, in certain cases it may be desirable to perform a further series of SELEX that is tailored by the information received during the SELEX experiment. For example, in a second series of SELEX, conserved regions of the nucleic acid ligand family may be fixed while all other positions in the ligand structure are randomized. In an alternate embodiment, the sequence of the most representative member of the nucleic acid ligand family may be used as the basis of a SELEX process wherein the original pool of nucleic acid sequences is not completely randomized but contains biases towards the best-known ligand. By these methods it is possible to optimize the SELEX process to arrive at the most preferred nucleic acid ligands.

The aptamers of invention can have any desired length. The aptamers may include at least about 15 oligonucleotides. Preferably, the aptamers may include up to about 80 nucleotides.

Modern techniques allow the identification or generation of aptamers with any desired equilibrium constant ($K_D$). In some embodiments, the aptamer includes equilibrium constant ($K_D$) of about 1 pM up to about 10.0 μM; about 1 pM up to about 1.0 μM; about 1 pM up to about 100 nM; about 100 pM up to about 10.0 μM; about 100 pM up to about 1.0 μM; about 100 pM up to about 100 nM; or about 1.0 nM up to about 10.0 μM; about 1.0 nM up to about 1.0 μM; about 1 nM up to about 200 nM; about 1.0 nM up to about 100 nM; about 500 nM up to about 10.0 μM; or about 500 nM up to about 1.0 μM.

The target molecule may include a small molecule, a protein, or a nucleic acid. For the aptamers described herein, target molecule is CD3 ε/γ and/or CD3 ε/δ proteins.

The aptamers of invention can be used in a pharmaceutical composition.

Definitions

Nucleic acid means DNA, RNA, XNA single-stranded or double-stranded and any chemical modifications thereof.

Aptamer (or ligand) means a nucleic acid that binds another molecule (target). In a population of candidate nucleic acids, an aptamer is one which binds with greater affinity than that of the bulk population. Among a plurality of candidate aptamer sequences there can exist more than one aptamer for a given target. The aptamers can differ from one another in their binding affinities for the target molecule.

A variant of a nucleic acid sequence, such as an aptamer sequence, can include sequences having at least 80%, at least 85%, at least 90%, at least 95%, at least 97%, at least 98%, or at least 99% sequence identity as determined by a sequence identity algorithm, such as a BLAST algorithm. A variant can also include substitution of one or more bases by non-naturally occurring bases, or elimination of one or more bases, optionally with replacement of the nucleotide by a linker or a bond. A variant also can include a modified nucleic acid backbone, such as that found in peptide nucleic acids (PNA).

A plurality of candidate aptamer sequences is a plurality of nucleic acids of differing sequence, from which to select a desired aptamer. The source of candidate sequences can be from naturally-occurring nucleic acids or fragments thereof, chemically synthesized nucleic acids, enzymatically synthesized nucleic acids or nucleic acids made by a combination of the foregoing techniques.

Target molecule means any compound of interest for which a ligand is desired. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation. A target can also be a cell expressing a desired protein to which the aptamers sought specifically bind. Aptamer selection using cells can be referred to as cell-SELEX (Chen C et al., *npj Precision Oncology* (2017) 1-37). Cell-SELEX uses living cell as target. Aptamers bind with living cell membrane proteins. The procedure of cell-SELEX includes positive selection and negative selection. For positive selection, single strand DNA or RNA library is incubated with target cells and the bound sequences are collected. The bound sequences are incubated with negative cell, and the unbound sequences are collected to be used for amplification, sequencing, and cloning. Aptamers are obtained after several alternate cycles. The present disclosure includes selection of anti-CD3 aptamers by incorporating use of live cells as target. CD3 positive Jurkat cells and CD3 negative Ramos cells were used for positive and negative selection, respectively.

Separation (or partitioning) means any process whereby ligands bound to target molecules, termed aptamer-target pairs or sequence-target complexes herein, can be separated from nucleic acids not bound to target molecules. Separation can be accomplished by various methods known in the art. Nucleic acid-protein pairs can be bound to nitrocellulose filters while unbound nucleic acids are not. Columns which specifically retain sequence-target complexes (or specifically retain bound aptamer complexed to an attached target) can be used for partitioning. Liquid-liquid partition can also be used as well as filtration gel retardation, and density gradient centrifugation. The choice of separation method will depend on properties of the target and of the sequence-target complexes and can be made according to principles and properties known to those of ordinary skill in the art.

Amplifying means any process or combination of process steps that increases the amount or number of copies of a molecule or class of molecules. Amplifying RNA molecules in the disclosed examples was carried out by a sequence of three reactions: making cDNA copies of selected RNAs, using polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the initial mixture.

Randomized is a term used to describe a segment of a nucleic acid having, in principle any possible sequence over a given length. Randomized sequences will be of various lengths, as desired, ranging from about eight to more than 100 nucleotides. The chemical or enzymatic reactions by which random sequence segments are made may not yield mathematically random sequences due unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into randomized sequence, for example, by altering the molar ratios of precursor nucleoside (or deoxynucleoside) triphosphates of the synthesis reaction. A deliberate bias may be desired, for example, to approximate the proportions of individual bases in a given organism, to affect secondary structure, or to influence melting pH or pH sensitivity. The sequences may be biased to contain a higher percentage of AT than CG base pairs, thus decreasing their melting pH.

EXAMPLES

Example 1: Anti-CD3 DNA Aptamers

Library and Primers

Single-stranded DNA (ssDNA) library designed for the DNA aptamer selection was purchased from TriLink Biotechnologies. The library consisted of a 40-nucleotide random region (N40) flanked with two constant regions: 5'-TAGGGAAGAGAAGGACATATGAT-(N40)-TTGACTAGTACATGACCACTTGA-3' (SEQ ID NO:114), which was used as a template for PCR amplification. The primers sequences for PCR reaction were: 5'-TAGGGAAGAGAAGGACATATGAT-3' (SEQ ID NO:115) (forward primer) and 5 'biotin-TCAAGTGGTCATGTACTAGTCAA-3' (SEQ ID NO:116) (reverse primer). During selection, the library was amplified in Eppendorf Mastercycler Nexus using AmpliTaq Gold 360 polymerase kit (Applied Biosystems) according to manufacturer's protocol. The following conditions were used: polymerase activation and initial denaturation at 95° C. for 10 min, denaturation at 95° C. for 30 s, annealing at 45° C. for 30 s (with increment of 0.2° C. for each PCR cycle), extension at 72° C. for 1.5 min and final extension at 72° C. for 7 min. The modification of reverse primer with biotin at the 5' end allowed generation of a ssDNA library for each successive round of the selection from amplified double-stranded DNA (dsDNA) using streptavidin-coupled magnetic beads. Both primers were HPLC grade purified and purchased from Eurogentec.

DNA Aptamers Selection

SELEX process consisted of six selection rounds and was performed on recombinant c chain of CD3 protein consisting in CD3 epsilon/gamma (CD3 ε/γ) and CD3 epsilon/delta (CD3 ε/δ) dimers purchased as C-terminal fusions with constant Fc domain of human Immunoglobulin G1. Consequently, the Fc fragment of human Immunoglobulin G1 (IgG1 Fc) was used for negative selection. All proteins were purchased from AcroBiosystems. Each round of selection included the following steps: counter selection, incubation of the ssDNA library with the target, PCR amplification of sequences that recognized the target and separation of dsDNA on streptavidin-modified magnetic beads. Prior to each cycle, ssDNA library (2.5 nmol for the initial cycle) was denatured at 95° C. for 5 min and then immediately cooled at 4° C. for 5 min in the selection (SELEX) buffer (20 mM HEPES, 150 mM NaCl, 5 mM KCl, 1 mM $MgCl_2$, and 1.5 mM $CaCl_2$), pH 7.2, DNase and RNase free purchased from Sigma-Aldrich). To eliminate Fc domain specific sequences, ssDNA library was incubated with IgG1-Fc protein (0.5 nmol, 1 μM) at 37° C. for 90 min in a thermocycler (Eppendorf Mastercycler Nexus). The reaction mixture was then filtered through a nitrocellulose acetate membrane (0.45 μm HAWP membrane, 25 mm diameter, Millipore) which was inserted in a 25 mm diameter support filter holder from Millipore and washed with selection buffer. Prior to filtration, HAWP membranes were soaked in selection buffer for at least 30 min. After filtration, the membranes with attached IgG1-Fc/ssDNA complex and non-specific ssDNA sequences bound to the filter, was discarded. The filtrate containing unbound sequences was concentrated using 10 kDa AMICON Ultra-15 MWCO filters followed by incubation with the positive target. In the first cycle, aptamers were selected against the recombinant CD3 ε/γ (0.15 nmol, 0.3 μM) and CD3 ε/δ (0.15 nmol, 0.3 μM) domains in a volume of 500 μL at 37° C. for 120 min in a thermocycler. From the second round, CD3 ε/γ and CD3 ε/δ were used alternately in each cycle. The reaction mixture was then filtered through nitrocellulose acetate membrane. The filter was washed with 8 mL of selection buffer to remove all low-affinity and low-specificity sequences attached to the proteins. The ssDNA that bound to the proteins retained on the filter was eluted by incubating the membrane in 1 mL of 7 M urea at 75° C. for 5 min, twice. The recovered ssDNA solution was diluted two times in DNase and RNase free water (Invitrogen) and concentrated using 10 kDa AMICON Ultra-4 MWCO filters. The sequences were re-diluted in water and re-concentrated. The solution obtained was purified on Micro Bio-Spin P-6 columns (in SSC buffer, Bio-Rad) and precipitated in ethanol (HPLC grade, Fisher) and 3 M of sodium acetate pH 5.2 (ThermoScientific, Waltham, MA, USA) in the presence of 5 μL of linear polyacrylamide (Invitrogen). After incubation at −25° C. for around 1 h, eluted ssDNA was centrifuged at 21000 g at 4° C. for 20 min. The supernatant was discarded, the pellet with ssDNA was diluted in 200 μL of DNase and RNase free water and left in air for 20 min to evaporate the ethanol. The selected ssDNA sequences were amplified in a PCR reaction (AmpliTaq Gold 360, Applied Biosystems) in the presence of un-modified forward primers and biotinylated reverse primers. The optimal number of PCR cycles was chosen individually for each round of the selection. For this purpose, the progress of the amplification was followed by migration of dsDNA samples obtained after various number of PCR cycles on an agarose gel (3% with SYBR-Safe in TBE buffer, Invitrogen). PCR reaction was stopped when the band corresponding to dsDNA appeared on the agarose gel. The PCR mixture with amplified dsDNA was then collected, diluted in water to obtain a final volume of 15 mL and concentrated using 10 kDa AMICON Ultra-15 MWCO membranes. An aliquot of the concentrated sample was stored at −20° C. for sequencing analysis. In order to purify and generate ssDNA chains for the next cycle of the selection, the remaining sample was bound to the streptavidin coated magnetic beads (MyOne Streptavidin Dynabeads) through biotin present on the amplified dsDNA. Incubation was performed at room temperature for 18 min in binding buffer (1 M NaCl, 5 mM Tris, 0.5 mM EDTA pH 8.0, DNase and RNase free purchased from Sigma-Aldrich), according to manufacturer's protocol. 3 mg of magnetic beads were used for 20 μg of dsDNA. Afterwards, magnetic beads with dsDNA were separated from solution and washed five times with binding buffer (double volume used for incubation) to eliminate any remaining non-specifically bound library species and PCR reaction residues. Separation of the DNA chains occurred by denaturation under basic conditions and was carried-out by incubation of modified beads in a solution of 50 mM NaOH (BioUltra from Sigma-Aldrich) for 3 min. As a result, biotinylated DNA chain remained attached to the magnetic beads and un-modified chain of interest was released to the solution and recovered. The obtained ssDNA was then diluted in water to a final volume of 4 mL and concentrated using a 10 kDa AMICON Ultra-4 MWCO to remove NaOH. The exchange to selection buffer was performed using Micro Bio-Spin columns (P-6; BioRad). The quality of recovered ssDNA library was analysed by migration on agarose gel (3% in TBE buffer) and the concentration was calculated using NanoDrop One (ThermoScientific, Waltham, MA, USA) by measuring the absorbance at 260 nm.

During successive rounds of the SELEX process, the stringency of the selection was gradually increased (see Table 1). For example, the concentration of the target and ssDNA library was decreased, incubation time with protein was reduced, volume of buffer for membranes washing after the selection was increased and for the last selection round non-specific competitor (yeast total RNA, Sigma-Aldrich) was added.

TABLE 1

SELEX conditions used for each selection round of DNA aptamers

| Round | Counter selection | Target | Target quantity (pmol) | ssDNA quantity (pmol) | Membranes washing (mL) | Incubation time (min) | Competitor (tRNA) |
|---|---|---|---|---|---|---|---|
| 1 | 1 μM IgG1 Fc | CD3 e/g + CD3 e/d | 150 + 150 | 200 | 8 | 120 | — |
| 2 | 0.5 μM IgG1 Fc | CD3 e/g | 150 | 400 | 10 | 45 | — |
| 3 | 0.5 μM IgG1 Fc | CD3 e/d | 125 | 400 | 10 | 30 | — |
| 4 | 0.5 μM IgG1 Fc | CD3 e/g | 75 | 230 | 12 | 30 | — |
| 5 | 0.5 μM IgG1 Fc | CD3 e/d | 50 | 230 | 13 | 25 | — |
| 6 | 0.5 μM IgG1 Fc | CD3 e/g | 50 | 180 | 15 | 20 | 20 μg/mL |

PCR aliquots obtained after each SELEX cycle as well as initial ssDNA library were analyzed by next generation sequencing using Illumina NextSeq MidOutput (150 cycle) system. This analysis was performed at the Genome Technology Center, New York University. Data from high throughput sequencing was analyzed using Galaxy project web site. Based on the sequencing results, aptamer candidates were chosen for affinity and specificity test.

The nucleic acid sequences of these aptamers are shown in FIGS. 1, 6 and 7A-7B. DNA aptamers with or without the flanking regions used in PCR amplification were obtained from Eurogentec Kaneka (Liege Belgium) as HPLC-RP purified single stranded oligos synthetized via standard solid phase phosphoramidite chemistry. Biotin was added to the 5'-end of aptamers as a Biotin-TEG that introduces a 16-atom mixed polarity spacer between the aptamer sequence and the biotin flag. For all aptamers, molecular weight, purity and integrity were verified by HPLC-MS by the manufacturer.

The same synthetic approach was followed in order to introduce mutations in the core sequence CELTIC_core and shown in FIG. 17.5 and FIG. 18. Abasic sites were created at various positions along the core sequence by incorporating C3 spacer arms during the solid phase synthesis. When required, further hexaethylene glycol (HEG) linkers were inserted between the 5'-end modifying functional groups and the first nucleotide the aptamers in 5' position in order to minimize steric hindrance. Further modifications of the core sequence variants involved the addition of 3'-3' deoxythymidine as a strategy to enhance resistance to nuclease degradation.

Finally, the 5'-ends of the aptamers were functionalized with primary amines via a C6 amino modifier added to terminal phosphates. Tetrazine functional groups were added as Tetrazine-PEG5-NHS esters via standard NHS/EDC chemistry, introducing a 16-atom mixed polarity spacer between the aptamer sequence and the tetrazine flag.

Example 2: Anti-CD3 RNA Aptamers

Library and Primers

The initial RNA library template and primers were synthesized by IDT (Coralville, IA, USA) as ssDNA: 5'-CCTCTCTATGGGCAGTCGGTGAT-(N20)-TTTCTGCAGCGATTCTTGTTT-(N10)-GGAGAATGAGGAACCCAGTGCAG-3', (SEQ ID NO:117), 5'-TAATACGACTCACTATAGGGCCTCTCTATGGGCAGTCGGTGAT-3', (SEQ ID NO:118) (forward primer), 5'-CTGCACTGGGTTCCTCATTCTCC-3' (reverse primer) (SEQ ID NO:119). Two short "blocking" sequences (purchased from IDT) complementary to the 5'- and 3'-constant primer regions were synthetized to minimize the effect of primers on secondary structure: 5'-ATCACCGACTGCCCATAGAGAGG-3', (SEQ ID NO:120) (forward blocking sequence), 5'-CTGCACTGGGTTCCTCATTCTCC-3', (SEQ ID NO:121) (reverse blocking sequence). An additional biotinylated "capture" sequence, complimentary to the constant center region of the library was also synthesized by IDT: 5'-Biotin-GTC-PEG-6 Spacer-CAAGAATCGCTGCAG-3' (SEQ ID NO:122). All materials were ordered at a 250 nmole scale and underwent desalting purification.

The RNA library for RNA aptamer selection was modified with 2'Fluoro- (2'F-) pyrimidines for greater stability in the final application. T7 primer was combined with library template sequences for primer extension with Titanium Taq DNA polymerase (Clontech; Mountain View, CA, USA). Primer-extended material was then transcribed using the Durascribe® T7 Transcription Kit (Epicentre; Madison, WI, USA), purified on denaturing polyacrylamide with 8 M urea (Sequel NE Reagent, Part A and Part B), which was purchased from American Bioanalytical (Natick, MA, USA). During selection, the library was reverse transcribed using SuperScript IV Reverse Transcriptase (Invitrogen; Carlsbad, CA, USA) according to manufacturer's protocol and amplified using Titanium Taq DNA polymerase from Clontech. During selection, the library was amplified using a following PCR protocol (10 seconds at 95° C., 30 seconds at 60° C., with initial HotStart activation of 60 seconds at 95° C.). RNA library was then transcribed using the Durascribe® T7 Transcription Kit and purified on polyacrylamide gel (PAGE). Gel elution buffer for 4° C. overnight post-purification library recovery was prepared to 0.5 M $NH_4OAc$, 1 mM EDTA (both purchased from Teknova), 0.2% SDS (purchased from Amresco), pH 7.4.

RNA Aptamer Selection

RNA library screening was conducted with nine rounds of the selection using a Melting-Off approach. Rounds 1-6 of the selection were performed on the recombinant £ chain of CD3 protein as a target and with IgG1 Fc fragment as a counter-target, by using the same material as for DNA aptamer selection. From seventh round, the screening was carried out on the Jurkat cells (Acute T Cell Leukemia Human Cell Line—ATCC TIB-152) that express CD3 protein and with Ramos cells (Burkitt's Lymphoma Human Cell Line—ATCC CRL-1596) for the negative selection step (cell-SELEX). Cell lines were obtained from American Type Cell Collection and cultured in RPMI-1640 medium (Gibco Invitrogen), supplemented with 10% FBS (Gibco Invitrogen) and 1% Penicillin/Steptomycin (Gibco Invitrogen). All selections were performed in 1×RPMI medium supplemented with 10% serum matrix and each of the SELEX rounds included the following steps: immobilization of the RNA library on the streptavidin-coated magnetic beads, counter selection, incubation with the target, reverse transcription of sequences that recognized the target, PCR amplification, and transcription to RNA. Prior to each round, an aliquot of streptavidin-coated magnetic beads (MyOne Streptavidin T1 Dynabeads™, typically 1 pmole of biotinylated material is used with every 20 μg of Dynabead™, amount varied depending on the required stringency) was pre-washed three times with 200 μL PBS-T (final concentration of 0.01% Tween 20, pH 7.4) wash buffer. RNA library was refolded in 1×RPMI medium without serum (1-minute denaturing at 90° C., 5-minute annealing at 60° C., then 5 minutes at 23° C.) with twice the library molar amount of both primer-blocking sequences and the capture sequence. This was done to minimize the effects of the constant primer regions on the secondary structure of aptamers, to allow the library to be captured by the magnetic beads through a streptavidin-biotin binding interaction and to protect the ends of the aptamers from exonucleases. After refolding was completed, the library was captured on magnetic beads by incubation for 15 minutes at room temperature. Magnetic beads were then separated from solution and washed three times with 200 μL of the selection buffer at 37° C. to eliminate any remaining PBS-T and non-specifically bound library species. Magnetic beads with immobilized RNA library underwent then a counter selection incubation in 200 μL of the counter-target preparation at 37° C. for 30 minutes which resulted in releasing the non-specific sequences from the magnetic beads. Non-specific library members were then discarded and the magnetic beads were washed six times for 7 min with 200 μL of the selection buffer. Positive selection consisted of the incubation of the magnetic beads RNA library with 200 μL of the positive preparation at 37° C. for 30 minutes. In the first cycle, aptamers were selected against the recombinant CD3 ε/γ and CD3 ε/δ domains (0.1 μM each) and from the second round, CD3 ε/γ and CD3 ε/δ were used alternately. In the sixth round, prior to selection against the cells, the library was split into two positive conditions (against CD3 ε/γ or CD3 ε/δ respectively) to ensure that a response could be observed against both recombinant proteins. The sixth-round positive libraries were then pooled together during recovery and followed by cell selections. For cell-SELEX rounds, target and counter-target cells were thawed, pelleted by centrifugation at 5,000×g, and washed twice with the selection buffer, before being suspended in 200 μL of the selection buffer. The number of cells used for incubation was $15\times10^6$ for counter selection and $1\times10^6$-$15\times10^6$ for positive selection. Once the positive selection was completed, the supernatant containing the sequences that recognized the target was separated from magnetic beads and recovered. The supernatant then underwent a second magnetic separation in order to ensure that the magnetic beads had been completely removed. For cell-SELEX rounds, the targeted Jurkat cells were pelleted by centrifugation at 5,000×g after the second magnetic separation. The pelleted cells were washed once with 200 μL of the selection buffer to remove low-affinity and low-specificity aptamer species. Library was recovered from the cells by heat denaturation at 70° C. Recovered library in all rounds underwent protein precipitation with MPC reagent (Lucigen Corp, Middleton, WI, USA), ethanol precipitation, and concentration of the sample, and were purified by 10% denaturing PAGE with 8 M urea. The library was then reverse-transcribed using SuperScript IV Reverse Transcriptase according to the manufacturer's instructions, amplified using Titanium® Taq DNA polymerase, and transcribed using the Durascribe® T7 Transcription Kit according to the manufacturer's instructions. Transcription products were then purified by 10% denaturing polyacrylamide gel electrophoresis (PAGE) with 8 M urea. Gel slices were excised, eluted overnight at 4° C. in gel elution buffer, and the concentration of RNA library was calculated by measuring the absorbance at 260 nm on NanoDrop-1000.

During successive rounds of the SELEX process, the concentration of the RNA library was gradually decreased. Additional parallel assessments and "cross over fitness test" were performed to facilitate identification of good aptamer candidates during post-selection bioinformatic analysis.

Aptamer candidates were chosen by next generation sequencing using MiniSeq Mid Output (150 cycle) system (Illumina). Several aptamers were selected for further testing. For this purpose, 2'-Deoxy-2'-fluoro-thymidine-modified RNA aptamers were purchased from Integrated DNA Technologies (IDT, Coralville, USA). Biotin was added to the 5'-end of aptamers as a Biotin-TEG that introduces a 16-atom mixed polarity spacer between the aptamer sequence and the biotin flag. Molecular weight, purity and integrity were verified by HPLC-MS. The nucleic acid sequences of these aptamers are shown in FIG. 27.

Example 3: Determination of the Affinity and Specificity of Anti-CD3 DNA Aptamers to CD3 Protein Expressed on the Cells The affinity and specificity of DNA aptamer candidates to CD3 protein expressed on the cells were evaluated by flow cytometry. These studies were performed on CD3 positive Jurkat (Acute T Cell Leukemia Human Cell Line—ATCC TIB-152), EL4 (Lymphoma Mouse Cell Line—ATCC CRL-2638) and CD3 negative Ramos (Burkitt's Lymphoma Human Cell Line—ATCC CRL-1596) cells by incubation with biotinylated candidate aptamers in selection (SELEX) buffer, supplemented with 5% of FBS. Cells were cultured in RPMI-1640 medium (Gibco Invitrogen), supplemented with 10% FBS (Gibco Invitrogen) and 1% Penicillin/Steptomycin (Gibco Invitrogen) prior to use. Prior to experiment, Jurkat, EL4 and Ramos cells ($2.5\times10^5$ cells/well) were seeded in 96-well plates and centrifuged at 2500 rpm for 2 min. The supernatant was discarded, and the pelleted cells were washed twice with 200 μL of SELEX-5% FBS buffer preheated at 37° C. Each washing step was followed by centrifugation at 2500 rpm for 2 min. Candidate aptamers were denatured at 95° C. for 5 min and immediately placed on ice block of 4° C. for 5 min. Test samples were subsequently diluted at two different concentration ranges: 3, 10, 30 nM and 1, 2.5, 5, 7.5, 10 nM followed by addition of 100 nM phycoerythrin-labelled streptavidin (streptavidin-PE, eBioscience) to each solution. For incubation with EL4 cells, aptamers were additionally diluted to 100 and 300 nM.

Jurkat, EL4 and Ramos cells were resuspended in the DNA dilutions (100 μL/well) and incubated at 37° C. for 30 min in a 5% $CO_2$ humidified atmosphere. As controls, cells were incubated with CD3 monoclonal antibodies (PE-labelled, OKT3 human anti-CD3, Invitrogen), PE-streptavidin or the respective buffers without additional reagents. After incubation, cells were centrifuged at 2500 rpm for 2 min and the supernatant with unbound sequences was discarded. The pelleted cells were washed with SELEX-5% FBS buffer (200 μL/well) and centrifuged twice in order to remove all weakly and non-specifically attached sequences. The cells were then washed with 1 mg/mL salmon sperm DNA solution (100 μL/well) at 37° C. in a 5% $CO_2$ humidified atmosphere. After 30 min, the salmon sperm solution was removed by centrifugation at 2500 rpm for 2 min and the cells were additionally washed twice with SELEX-5% buffer (200 μL/well) followed by centrifugation. Jurkat, EL4 and Ramos cells with attached DNA sequences were then fixed (BD CellFIX solution #340181) and the fluorescence-positive cells were counted by flow cytometry (AttuneNXT; Invitrogen, Inc.) on the YL-1 channel.

The results of the binding studies are shown in FIGS. 2A-2E. Five aptamers, CELTIC_1, CELTIC_1s, CELTIC_2, CELTIC_3, and CELTIC_21 were analyzed. CELTIC_1s differs from CELTIC_1 in that it lacks certain flanking region nucleotides. For comparison, binding of the aptamers to CD3 negative Ramos cells (Burkitt's Lymphoma Human Cell Line—ATCC CRL-1596) was also measured. All aptamers show preferential binding to CD3 positive cells. CELTIC_3 showed saturation binding at 10 nM. It showed significant binding at 3 nM with much greater specificity. Based on these results, the apparent $K_D$ of the binding of CELTIC_3 to Jurkat cells is between 3 nM and 10 nM. These aptamers were tested also at lower concentrations for binding to Jurkat cells, which confirmed preferential binding to Jurkat cells. See FIGS. 3A-3E. In another cell binding assay, binding to cells of aptamers CELTIC_2, CELTIC_3, and CELTIC_21 was compared to the binding of their shorter versions CELTIC2s, CELTIC_3s, and CELTIC_21s to cells. The improvement of the aptamers' specificity was observed when flanking regions were removed. See FIGS. 5A-5F. In yet another cell binding assay, binding of aptamers CELTIC_4s, CELTIC_5s, CELTIC_6s, CELTIC_9s, CELTIC_11s, CELTIC_19s, and CELTIC_21s to cells was measured, showing higher specificity to Jurkat then Ramos cells. The binding was tested at aptamer concentrations 3 nM, 10 nM, and 30 nM. See FIGS. 8A to 8G. A comparison of the results of binding of all the aptamers to Jurkat and Ramos cells at concentrations 3 nM and 10 nM is shown in FIGS. 9A and 9B, respectively. In a further cell binding assay, binding of aptamers CELTIC_1s, CELTIC_4s, CELTIC_9s, and CELTIC_19s to mouse EL4 cells was evaluated. The results of the binding studies are shown in FIGS. 13A-13D. The dose-dependent staining of cells obtained in this assay suggests that these aptamers are cross-specific and recognize both human and murine CD3 protein.

The same experimental set-up was used to evaluate the binding affinity and specificity of aptamer CELTIC_core corresponding to the computed conserved motif found among top 45 sequence families isolated during SELEX (FIG. 7C). As shown in FIG. 17.4, the shortening of aptamers down to the strictly conserved 21 nucleotides resulted in a highly improved recognition specificity for CD3 receptor. For each tested concentration, signal on CD3-positive Jurkat cells was measured when it was negligible on CD3-negative Ramos cells. This gain in specificity was achieved at the expense of affinity as apparent $K_D$ observed in this experiment was above 50 nM when parental sequences such as CELTIC_1s, CELTIC_4s, CELTIC_9s, and CELTIC_19s reached saturation of the signal above 10 nM.

Because this conserved motif exhibits GGG/C repeats that define a so-called "G-quadruplex" organization, we designed a set of mutants to eventually confirm the importance of the G residues in the predicted conformation, to identify the key positions involved in binding specificity and affinity, and to introduce mutations that may improve aptamer properties. Several sequence variants CELTIC_core_1 to CELTIC_core_13 (FIG. 17.5) were synthetized and tested on Jurkat and Ramos cells at concentrations of 50 and 100 nM as previously described. As comparison, unmodified core sequence CELTIC_core (50 and 100 nM) and full length CD3_CELTIC_1s (10 and 50 nM) were included in these analyses. Results disclosed in FIG. 17.6.A to 17.6.N indicate that each modification had a significant and unpredictable impact on the biological activity of the aptamers: adding GC or G at the 3'end of the conserved motif (CELTIC_core_1 or CELTIC_core_4) resulted in loss of specificity. Some mutations disrupted the interaction with CD3 receptor (CELTIC_core_2, CELTIC_core_5, CELTIC_core_6 and CELTIC_core_13). Loss of binding also occurred when G/C nucleotides at some positions were replaced by abasic sites (CELTIC_core_7 to CELTIC_core_11) while the creation of an abasic site at position 16 yielded an aptamer with a better affinity but reduced specificity.

The addition of a TTT triplet at the 5'-end (CELTIC_core_T) had no impact on the binding properties of the core sequence indicating that it was possible to introduce some space between the biotine label and the aptamer without any steric hindrance. This observation prompted us to evaluate further sequence variants all carrying HEG linkers at the 5'-end that introduce a longer C18 spacer. Sequence variants CELTIC_core_14 to CELTIC_core_44 were synthetized (FIG. 18) and tested on Jurkat and Ramos cells at concentrations of 50 and 100 nM as previously described (FIG. 19A-D). As comparison, unmodified core sequence CELTIC_core (50 and 100 nM) and full length CD3_CELTIC_1s and CD3_CELTIC_19s (10 and 50 nM) were included in these analyses. For most of positions an abasic site or base substitution disrupted the binding to CD3 receptor expressed the surface of Jurkat cells. Removal of nucleosides at positions 10 and 12 reduced the affinity (CELTIC_core_23 and CELTIC_core_25) whereas the same modification at positions 11 (CELTIC_core_24) or 16 (CELTIC_core_29) that are not part of the GGG/C triplets that define the "G-quadruplex" architecture yielded aptamers with equal or improved affinities and specificities respectively. Unexpectedly, substitution of the original C at position 16 by a G reduced the affinity of the aptamer (CELTIC_core_39) when an A had no impact (CELTIC_core_38) and a T translated into an improved affinity and specificity (CELTIC_core_40). Simultaneous modifications of positions 11 and 16 caused a gain in affinity and specificity (CELTIC_core_42) or an affinity loss (CELTIC_core_44). All together these results from conformation-function studies and summarized in FIG. 20 suggest that improved versions of the core sequence can be empirically engineered by substituting and introducing abasic sites at positions located outside of the GGG/C triplets that form the "G-quadruplex" structure.

Example 4: Determination of the Affinity and Specificity of Anti-CD3 RNA Aptamers to CD3 Protein Expressed on the Cells Anti-CD3 RNA aptamers were evaluated for binding to Jurkat and EL4 cells to determine their apparent $K_D$ of binding. The binding was carried out generally as described in Example 3 except that instead of the SELEX buffer DPBS was used. The aptamers were used at three concentrations, 30 nM, 100 nM, and 300 nM. For incubations with EL4 cells aptamers were also diluted to 3 nM and 10 nM. The results of the binding studies are shown in FIGS. 30A-E. Five aptamers, ARACD3-3700006, ARACD3-0010209, ARACD3-3130001, ARACD3-2980001, and ARACD3-0270039 were analyzed. Binding of the aptamers to CD3 negative Ramos cells (control) was also measured for evaluating specificity of the aptamers. In yet another cell binding assay, binding of aptamers ARACD3-3700006 and ARACD3-0010209 to mouse EL4 cells was evaluated. The results of the binding studies are shown in FIGS. 34A-B. The dose-dependent staining of cells obtained in this assay suggests that these aptamers are cross-specific and recognize both human and murine CD3 protein.

Figures 2A, 2B, 2C, 2D, 2E:
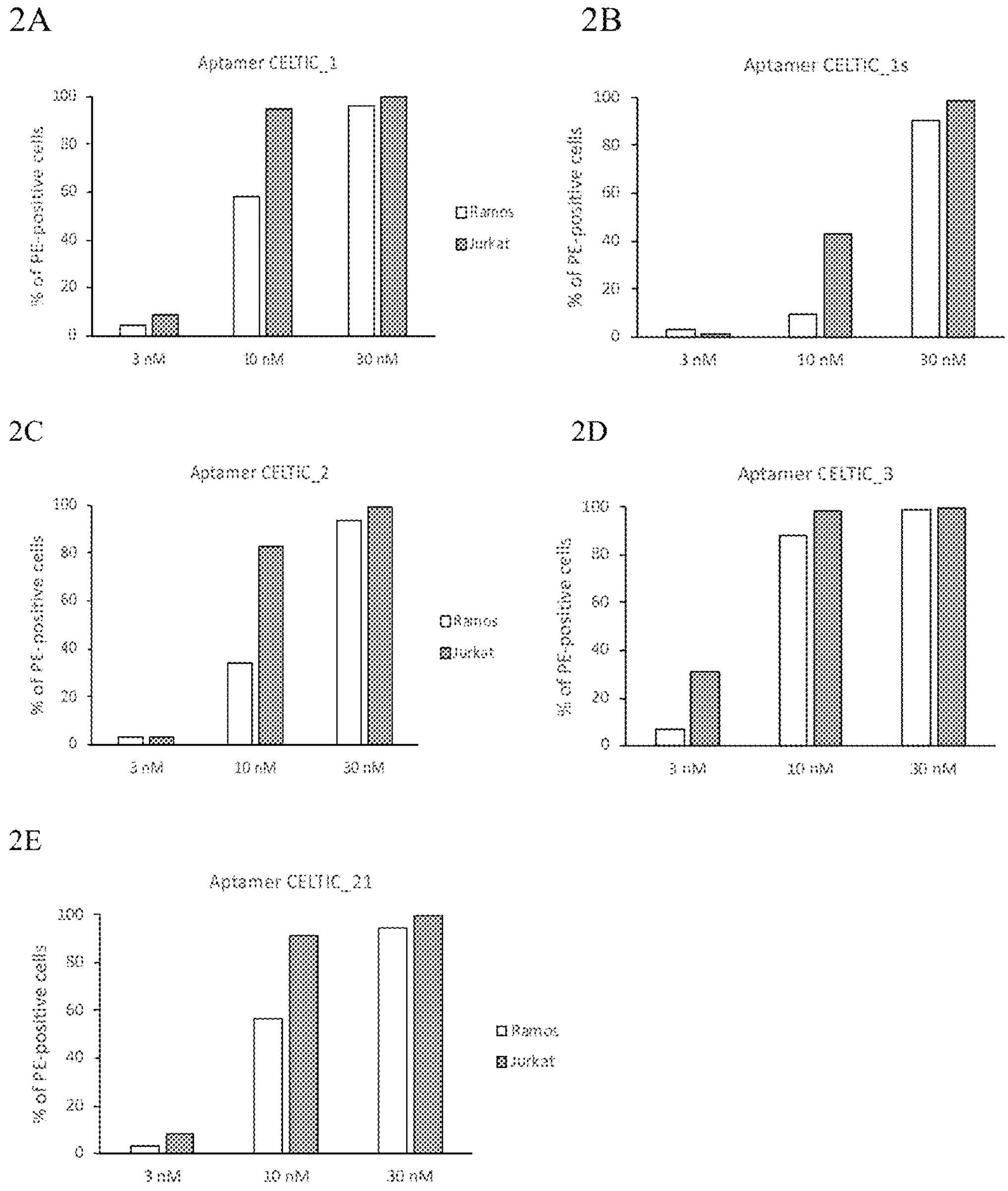
FIGS. 2A-2E are bar graphs showing results of binding of aptamers Cluster_1 (SEQ ID NO:1), Cluster_1s (SEQ ID NO:46, equivalent to Cluster_1 in which the 5' and 3' flanking regions have been removed), Cluster 2 (SEQ ID NO:2), Cluster_3 (SEQ ID NO:3), and Cluster_21 (SEQ ID NO:21) obtained by the SELEX procedure (FIG. 1) to Jurkat cells (human CD3 positive cells). For comparison, binding of the aptamers to Ramos cells (human CD3 negative cells; control) is also shown. The binding was tested at three concentrations of the aptamers: 3 nM, 10 nM, and 30 nM.
Figures 3A, 3B, 3C, 3D, 3E:
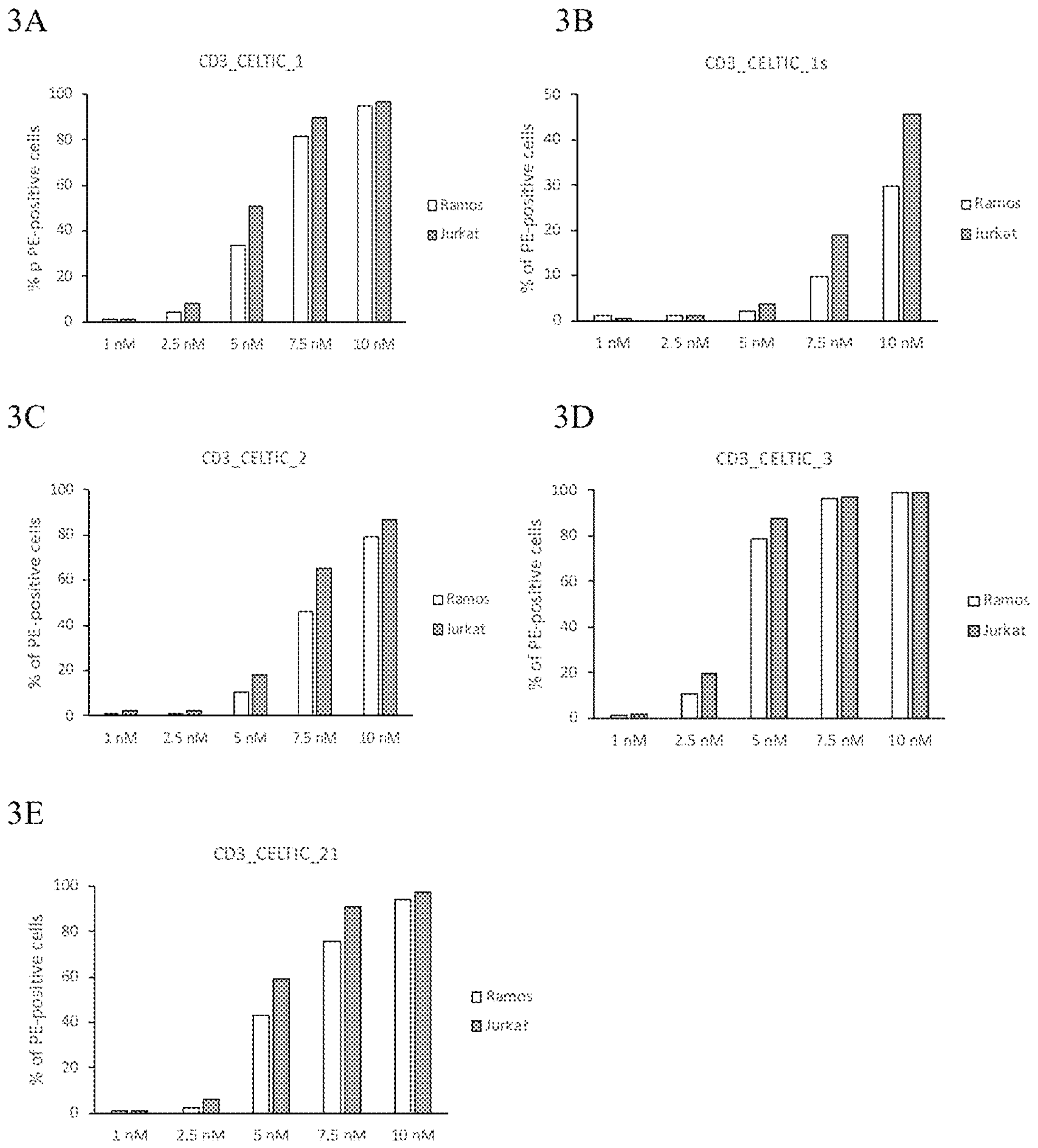
FIGS. 3A-3E are bar graphs showing results of binding of aptamers CELTIC_1 (SEQ ID NO:1), CELTIC_1s (SEQ ID NO:46), CELTIC_2 (SEQ ID NO:2), CELTIC_3 (SEQ ID NO:3), and CELTIC_21 (SEQ ID NO:21) obtained by the SELEX procedure (FIG. 1) to Jurkat cells (CD3 positive cells). For comparison, binding of the aptamers to Ramos cells (CD3 negative cells; control) is also shown. The binding was tested at the following aptamer concentrations: 1 nM, 2.5 nM, 5 nM, 7.5 nM, and 10 nM.
Figure 4A:
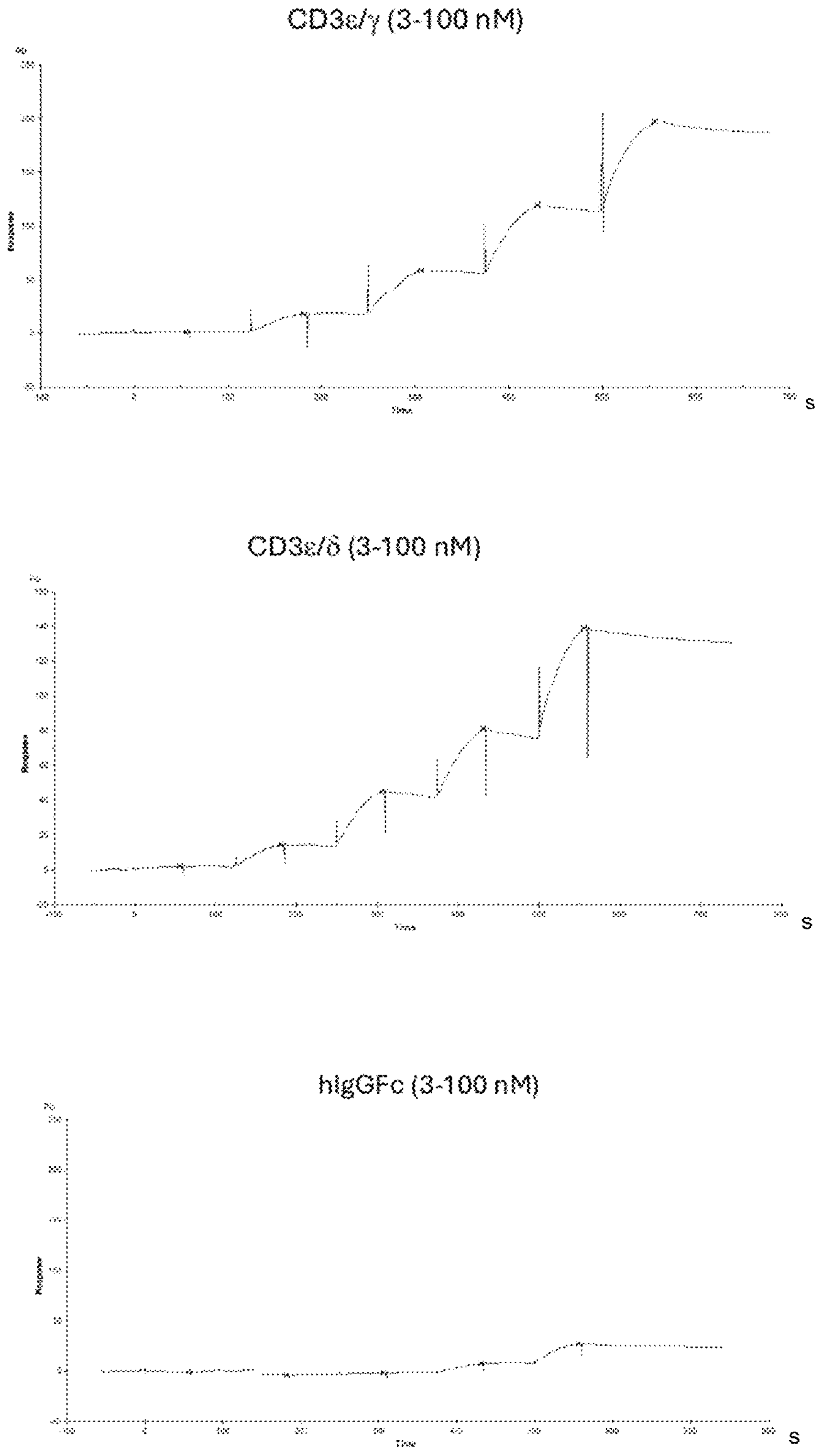
FIGS. 4A-4C are sensorgrams showing results of binding of each of biotinlylated aptamers CELTIC_1 (SEQ ID NO:1), CELTIC_3 (SEQ ID NO:3), and CELTIC_21 (SEQ ID NO:21) immobilized on a Series Sensor SA Chip to CD3 Ely (left column), CD3 (middle column), and control hIgG1 Fc (right column). Binding was measured by surface plasmon resonance using a single cycle kinetic protocol. Serial injections of aptamer at concentrations 3 nM, 10 nM, 30 nM, 50 nM, and 100 nM were performed.
Figure 4B:
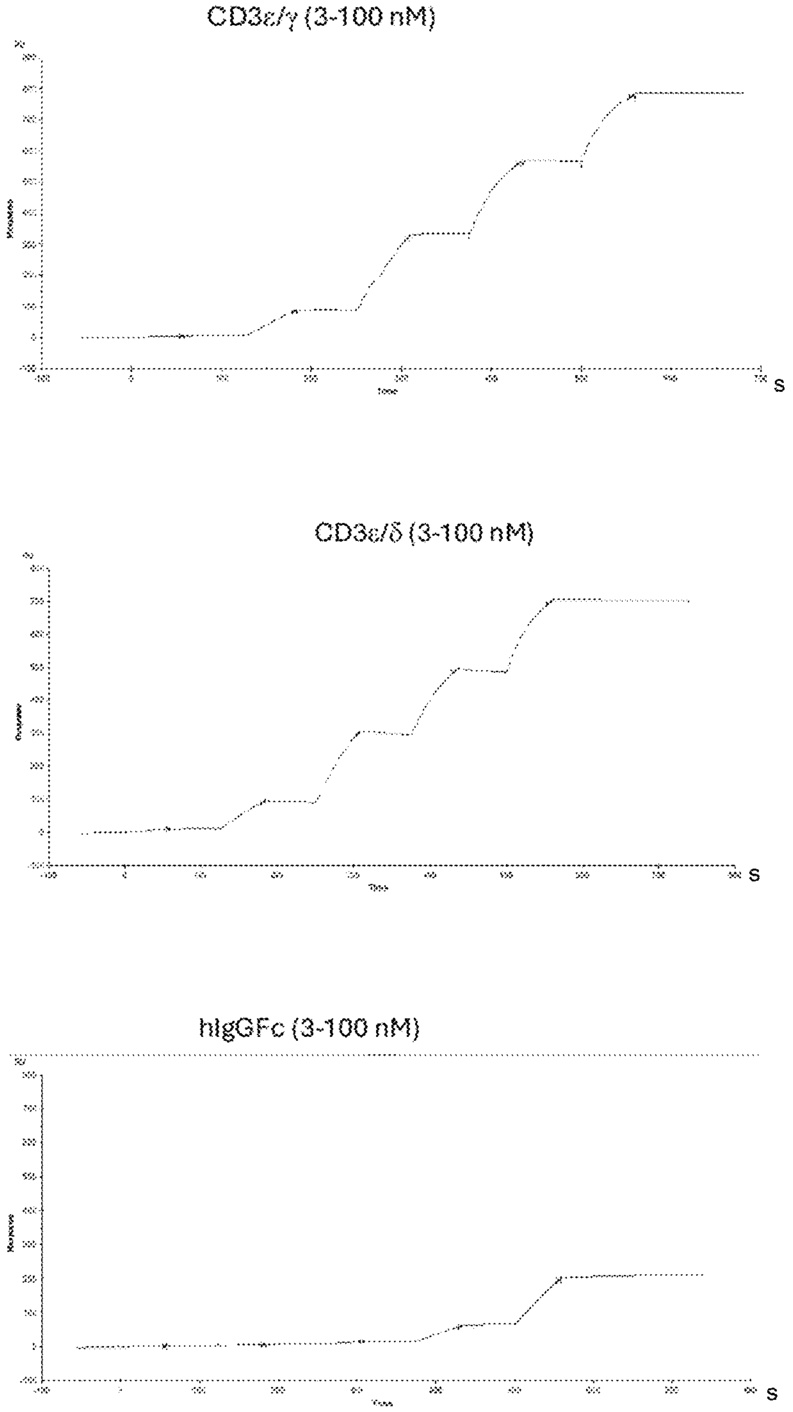
Figure 4C:
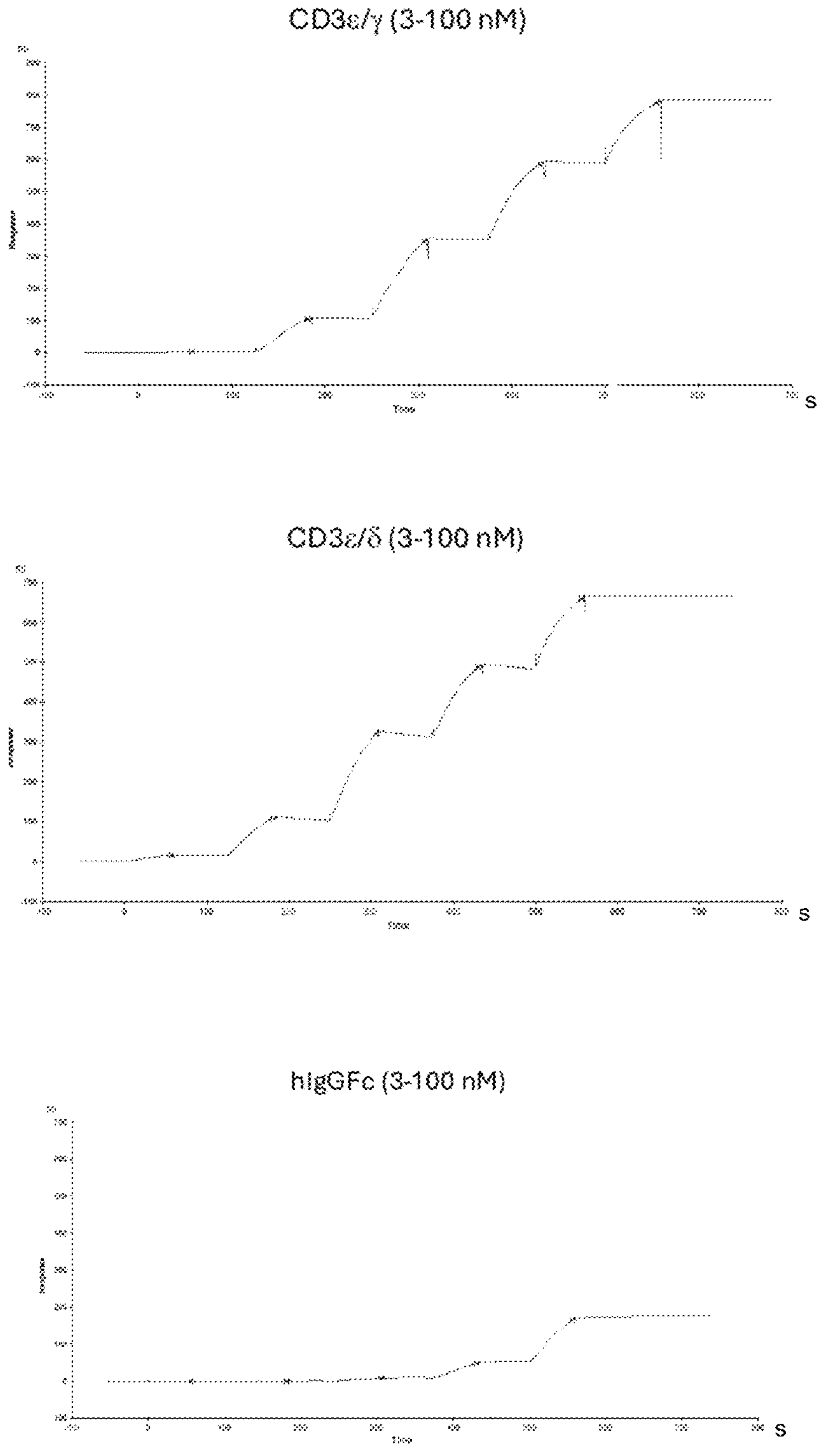
Figures 5A, 5B, 5C, 5D, 5E, 5F:
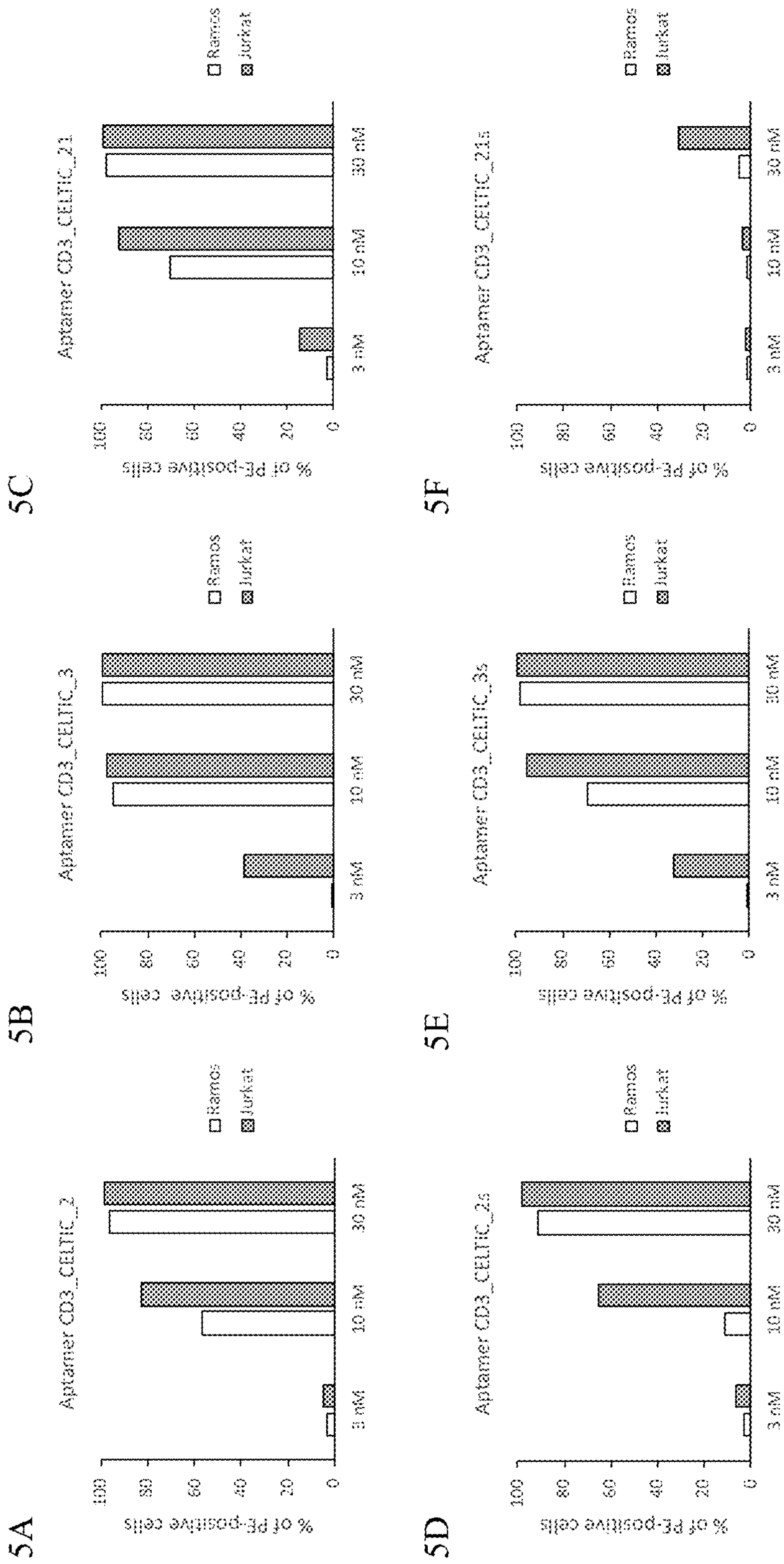
FIGS. 5A-5F are bar graphs showing results of binding of each of aptamers CELTIC_2 (SEQ ID NO:2), CELTIC_3 (SEQ ID NO:3), and CELTIC_21 (SEQ ID NO:21), and their shorter versions lacking flanking region nucleotides CELTIC_2s (SEQ ID NO:47), CELTIC_3s (SEQ ID NO:48), and CELTIC_21s (SEQ ID NO:49), to Jurkat cells (CD3 positive cells). Binding was measured at aptamer concentrations 3 nM, 10 nM, and 30 nM.

Example 5: Binding of Anti-CD3 DNA Aptamers as Measured by Surface Plasmon Resonance Binding affinity measurements were performed using a BIAcore T200 instrument (GE Healthcare). To analyze interactions between aptamers and CD3 proteins, 1000 Resonance Units of biotinylated aptamers were immobilized on Series S Sensor chips SA (GE Healthcare) according to manufacturer's instructions (GE Healthcare). SELEX buffer was used as the running buffer. The interactions were measured in the "Single Kinetics Cycle" mode at a flow rate of 30 μl/min and by injecting different concentrations of human CD3 ε/γ, CD3 ε/δ, IgG1 Fc and mouse CD3 ε/δ (Sino Biological). The highest protein concentration used was 100 nM. Other concentrations were obtained by 3-fold dilution. All kinetic data of the interaction were evaluated using the BIAcore T200 evaluation software. Examples of binding profiles obtained from these measurements are shown in FIGS. 4A-4C. Table 3 below provides a summary of $K_D$ values obtained from surface plasmon resonance measurements.

TABLE 3

$K_D$ values determined by surface plasmon resonance for the first 5 anti-CD3 DNA aptamers

| Aptamer | Human CD3ε/γ | Human CD3ε/δ | Human Fc IgG | Murine CD3ε/δ |
|---|---|---|---|---|
| CELTIC_CD3_1 | — | — | — | — |
| CELTIC_CD3_1s | 5 nM | 3.7 nM | 56.3 mM | 297.6 nM |
| CELTIC_CD3_2 | — | — | — | — |
| CELTIC_CD3_3 | 65.4 nM | 86.5 nM | 57.2 nM | 237 nM |
| CELTIC_CD3_21 | 43.6 nM | 62.2 nM | 58.9 nM | 136.5 nM |

Comparison of $K_D$ values for binding to human and murine CD3 ε/δ shows that the aptamers bind also to murine CD3 ε/δ but with lesser affinity. Further, it was observed that compared to the aptamer CELTIC_1 (CD3-1 in Table 1), CELTIC_1s (CD3-1s) bound to the CD3 proteins more strongly. Table 4 below provides a summary of $K_D$ values obtained from another set of surface plasmon resonance measurements. It includes $K_D$ values of the first five aptamers with and without flanking regions.

TABLE 4

$K_D$ values determined by surface plasmon resonance for the first 5 anti-CD3 DNA aptamers with or without ("s") flanking regions. From the recorded sensorgrams, data were computed with the steady-state analysis mode.

| Aptamer | Human CD3ε/γ | Human CD3ε/δ | Human Fc IgG | Murine CD3ε/δ |
|---|---|---|---|---|
| CELTIC_CD3_1 | NA | NA | NA | NA |
| CELTIC_CD3_1s | 53 nM | 125 nM | NA | 142 nM |
| CELTIC_CD3_2 | NA | NA | NA | NA |
| CELTIC_CD3_2s | 627 nM | 260 nM | NA | 237 nM |
| CELTIC_CD3_3 | 65.4 nM | 86.5 nM | NA | 237 nM |
| CELTIC_CD3_3s | 156 nM | 409 nM | NA | 109 nM |
| CELTIC_CD3_21 | 56.4 nM | 49.8 nM | NA | 313 nM |
| CELTIC_CD3_21s | 155 nM | 405 nM | NA | 104 nM |

Tables 5 and 6 below provide a summary of $K_D$ values of a few more aptamers. While the $K_D$ values listed in Tables 4 and 5 were obtained by performing measurements in a steady state analysis mode, those in Tables 3 and 6 were obtained by measurements performed in a kinetic analysis mode.

TABLE 5

$K_D$ values determined by surface plasmon resonance for the different anti-CD3 DNA aptamers without flanking regions. From the recorded sensorgrams, data were computed with the steady-state analysis mode.

| Aptamer | Human CD3ε/γ | Human CD3ε/δ | Human Fc IgG | Murine CD3ε/δ |
|---|---|---|---|---|
| CELTIC_CD3_1s | 53 nM | 125 nM | NA | 142 nM |
| CELTIC_CD3_21 | 56.4 nM | 49.8 nM | NA | 313 nM |
| CELTIC_CD3_2s | 627 nM | 260 nM | NA | 237 nM |
| CELTIC_CD3_3s | 156 nM | 409 nM | NA | 109 nM |
| CELTIC_CD3_4s | 117 nM | 144 nM | NA | 189 nM |
| CELTIC_CD3_5s | 182 nM | 120 nM | NA | 151 nM |
| CELTIC_CD3_6s | 287 nM | 168 nM | NA | 630 nM |
| CELTIC_CD3_9s | 47.3 nM | 60.5 nM | NA | 216 nM |
| CELTIC_CD3_11s | 94 nM | 138 nM | NA | 122 nM |
| CELTIC_CD3_19s | 104 nM | 150 nM | NA | 107 nM |
| CELTIC_CD3_21s | 155 nM | 405 nM | NA | 104 nM |
| CELTIC_CD3_22 | 162 nM | 164 nM | NA | 153 nM |

TABLE 6

$K_D$ values determined by surface plasmon resonance for the different anti-CD3 DNA aptamers without flanking regions. From the recorded sensorgrams, data were computed with the kinetic analysis mode.

| Aptamer | Human CD3ε/γ | Human CD3ε/δ | Human Fc IgG | Murine CD3ε/δ |
|---|---|---|---|---|
| CELTIC_CD3_1s | 5.2 nM | 9.9 nM | NA | 3.2 pM* |
| CELTIC_CD3_21 | 2.8 nM | 3.4 nM | NA | 0.01 nM* |
| CELTIC_CD3_2s | 65.2 nM | 3.2 μM | NA | 6.3 nM |
| CELTIC_CD3_3s | 0.01 nM* | 41.1 nM | NA | 0.01 nM* |
| CELTIC_CD3_4s | 4.1 nM | 3.4 nM | NA | 0.01 nM* |
| CELTIC_CD3_5s | 3.2 pM* | 3.2 pM* | NA | 0.2 nM* |
| CELTIC_CD3_6s | 0.02 nM* | 29.3 pM* | NA | 0.01 nM* |
| CELTIC_CD3_9s | 3.8 nM | 3.7 nM | NA | 0.01 nM* |
| CELTIC_CD3_11s | 3.9 nM | 3.2 nM | NA | 0.2 nM* |
| CELTIC_CD3_19s | 9.5 pM | 8.2 nM | NA | 11.9 nM |
| CELTIC_CD3_21s | 2.1 pM* | 23.3 nM | NA | 42.3 pM* |
| CELTIC_CD3_22 | 2.3 nM | 2.7 nM | NA | 3.4 nM |

Entries with the "*" label refer to overestimated values due to suboptimal fitting of sensorgrams.
NA = not applicable as no interaction was observed.

Example 6: Binding of Anti-CD3 RNA Aptamers as Measured by Surface Plasmon Resonance Binding of anti-CD3 RNA aptamers to each of purified recombinant human CD3 ε/γ and CD3 ε/δ proteins was measured using surface plasmon resonance. Binding studies were performed generally as described in Example 5 except that SELEX buffer was replaced by DPBS. The highest protein concentration used was 300 nM. Other concentrations were obtained by 3-fold dilution. Binding to hIgG1 Fc was used as control. Binding to murine CD3 ε/δ (mCD3 ε/δ) was also measured. The results of these studies are shown in Table 7 below.

TABLE 7

$K_D$ values determined by surface plasmon resonance for the different anti-CD3 RNA aptamers. From the recorded sensorgrams, data were computed with the kinetic analysis mode.

| Aptamer | Human CD3ε/γ | Human CD3ε/δ | Human Fc IgG | Murine CD3ε/δ |
|---|---|---|---|---|
| ARACD3-370006 | 21 nM | 75 nM | NA | 24.2 nM |
| ARACD3-0010209 | 20.6 nM | 22 nM | NA | ND |
| ARACD3-3130001 | 332 nM | NA | NA | ND |
| ARACD3-2980001 | 231 nM | 239 nM | NA | 26.5 nM |
| ARACD3-0270039 | 150 nM | 189 nM | NA | 17.7 nM |

ND = not determined.

The binding profiles of aptamers ARACD3-3700006, ARACD3-0010209, and ARACD3-3130001 are shown in FIGS. 31A-32C.

Example 7: T Cell Activation by Anti-CD3 DNA Aptamers

For measuring T cell activation by anti-CD3 DNA aptamers, the aptamers were used at 1 μM concentration together with CD28 co-stimulation of T cells. Cytokines secreted by the cells in response to the activation were measured by ELISA and Human Th1/Th2 Cytometric Bead Array (CBA). Expression of CD25 and CD69 activation markers at the surface of T cells was measured by flow cytometry. The results obtained are shown in FIGS. 14A-14L, 15A-15C and 16A-16C respectively.

T cell activation assays were carried out on peripheral blood mononuclear cells (PBMCs). Freshly prepared PBMCs were isolated from buffy coats obtained from healthy donors (Etablissement Francais du Sang, Division Rhones-Alpes). After diluting the blood with DPBS, the PBMCs were separated over a FICOLL density gradient (FICOLL-PAQUE PREMIUM 1.084 GE Healthcare), washed twice with DPBS, resuspended to obtain the desired cell density and cultured in RPMI-1640 medium (Gibco Invitrogen), supplemented with 10% FBS (Gibco Invitrogen) and 1% Penicillin/Steptomycin (Gibco Invitrogen) at 37° C., 5% $CO_2$.

Figure 12:
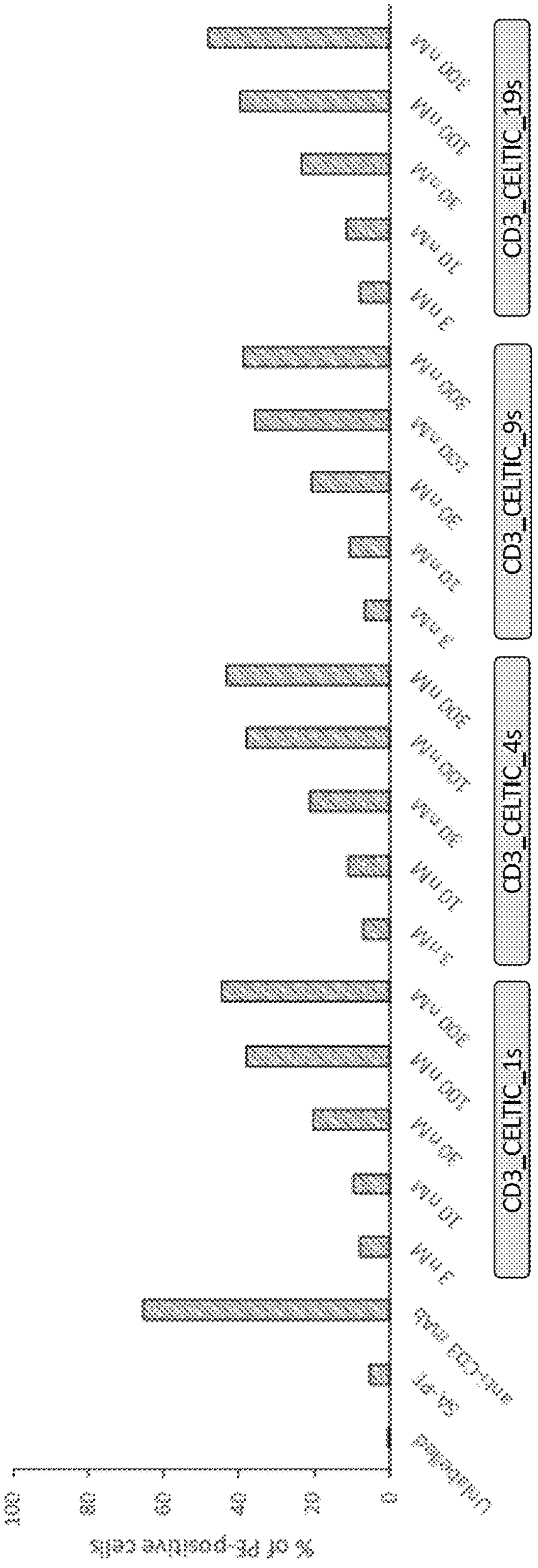
FIG. 12 is a bar graph showing results of binding of aptamers CELTIC_1s, CELTIC_4s, CELTIC_9s and CELTIC_19s obtained by the SELEX (FIG. 1) to peripheral blood mononuclear cells isolated from healthy donors. The binding was tested at the following aptamer concentrations.
Figures 13A, 13B, 13C, 13D:
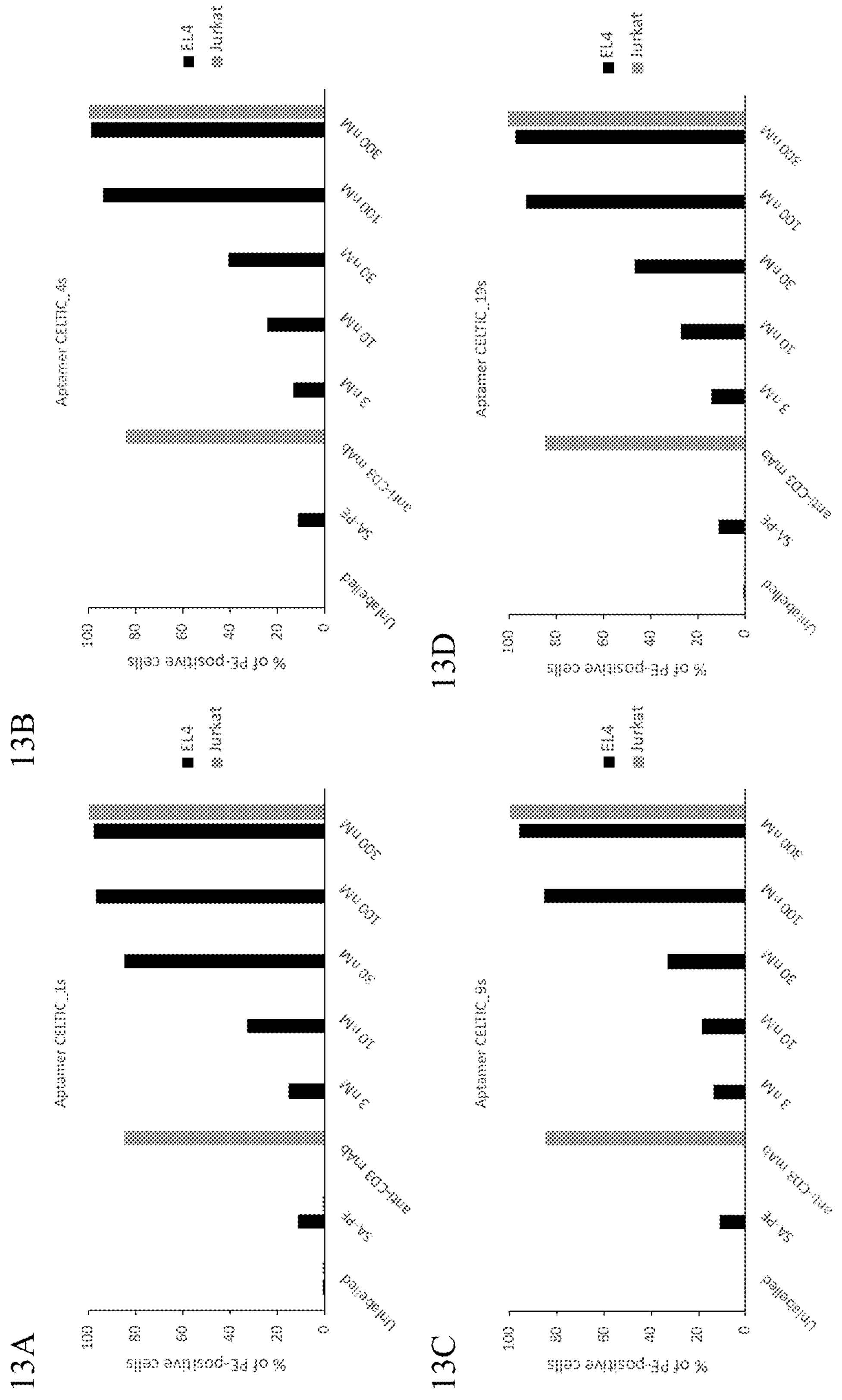

Before evaluating the T cell activation properties, the binding of anti-CD3 DNA aptamers to human PBMCs was first verified by flow cytometry as described in Example 3 except that SELEX buffer was replaced by RPMI-1640 medium supplemented with 10% FBS and 1% Penicillin/Steptomycin. Four aptamers, CELTIC_1s, CELTIC_4s, CELTIC_9s, and CELTIC_19s were used at concentration of 3 nM, 10 nM, 30 nM, 100 nM and 300 nM. The results of the binding studies are shown in FIG. 12.

PBMCs activation assays were carried out on four aptamers, CELTIC_1s, CELTIC_4s, CELTIC_11s, and CELTIC_19s with or without anti-CD28 monoclonal antibodies (Invitrogen) as co-stimulatory agent. A third condition with addition of fresh aptamer solution in presence of anti-CD28 mAb after 3 h, 19 h and 27 h was included to keep the concentration of reagents constant. Prior to experiment, PBMCs were seeded in 24-well plates at a density of $2.5\times10^5$ cells per well in 400 μL of RPMI medium containing 10% FBS and 1% penicillin/streptomycin and incubated for 4 h at 37° C., 5% $CO_2$. Candidate aptamers were denatured at 95° C. for 5 min and immediately placed on ice block of 4° C. for 5 min. After sampling 100 μL of supernatant (cytokine basal level condition), 100 μL of the stimulation solutions containing 1 μM DNA aptamers and 0.5 μg/mL CD28 mAb diluted in RPMI was added to the wells. Cells were incubated at 37° C., 5% $CO_2$ for 16, 24 or 48 h. Alternatively, PBMCs were incubated with 100 μL of a mix containing 2 μg/mL CD3 mAb and 5 μg/mL CD28 mAb (Invitrogen), a solution containing 2 μg/mL CD3 mAb or RPMI medium without reagents (negative control). The samples were then centrifuged at 320 g for 5 min and the supernatant was recovered. PBMC activation was assessed by measuring the levels of secreted Interleukin 2 (IL-2), Tumor Necrosis Factor alpha (TNF-α), and Interferon gamma (IFN-g) in culture supernatants collected at different intervals. Sandwich ELISAs (DUO SET ELISA R&D Systems) were used for the measurements. 100 μL of undiluted samples or cytokine standards were added to each well previously coated overnight with a capture antibody. IL-2, TNF-α, or IFN-g cytokine binding was detected with biotinylated detection antibodies revealed with a streptavidin-HRP conjugate and TMB substrate. Following the addition of stop solution, the ELISA plates were read at 450 nm on a VARIOSCAN LUX plate reader and the levels of cytokines determined against a reference standard curve. The results obtained are shown in FIGS. 14A-14L. Levels of secreted Interleukin 2 (IL-2), Interleukin 4 (IL-4), Interleukin 5 (IL-5), Interleukin 10 (IL-10), Tumor Necrosis Factor alpha (TNF-α) and Interferon gamma (IFN-g) in culture supernatants collected after 48 h were measured with Human Th1/Th2 Cytometric Bead Array (CBA) (Becton Dickinson Biosciences) according to manufacturer's instructions. The results obtained are shown in FIGS. 16A-16C.

Finally, activation of PBMCs was evaluated by analysing the expression of CD25 and CD69 activation markers at the surface of CD4- and CD8-positive T cells. After 48 h incubation in presence of the different test conditions and collection of culture supernatants for ELISA and CBA analysis, PBMCs were transferred into 96-well plates and centrifuged at 2500 rpm for 2 min. The supernatant was discarded, and the pelleted cells were washed twice with 200 μL of DPBS-0.2% BSA. Each washing step was followed by centrifugation at 2500 rpm for 2 min. Cells were then incubated with anti-CD4, anti-CD8, anti-CD25 and anti-CD69 monoclonal antibodies (Miltenyi) diluted in DPBS-0.2% BSA (1 μl/test). After 10 min incubation at 4° C., cells were centrifuged at 2500 rpm for 2 min and washed twice with DPBS-0.2% BSA (200 μL/well). Cells were fixed with CellFix solution (BD Biosciences) and the fluorescence-positive cells were counted by flow cytometry (AttuneNXT; Invitrogen, Inc.) on BL3 (anti-CD4-PerCP-Vio700), YL1 (CD69-PE), YL2 (CD8-PE-Vio-615) and YL4 (CD25-PE-Vio770) channels. The results obtained are shown in FIGS. 15A-15C.

Cells treated with anti-CD3 monoclonal antibodies combined with or without anti-CD28 monoclonal antibodies exhibited an increased secretion all measured cytokines except IL-5 and upregulation of surface expression of CD25 and CD69 activation markers. None of the tested aptamers was able to activate cytokine secretion of surface marker expression even when combined with costimulatory anti-CD28 antibody. Keeping aptamers concentrations constant by adding fresh solutions in a repeated manner to compensate for degradation in serum did not result in a more sustained activation profile.

Example 8: T Cell Activation by Anti-CD3 RNA Aptamers

T cell activation by anti-CD3 RNA aptamers was measured by incubating cells with aptamer at 1 μM concentration together with CD28 co-stimulation using the procedures described in Example 7. Cytokines secreted by the cells in response to the activation was measured by ELISA and Human Th1/Th2 Cytometric Bead Array. Expression of CD25 and CD69 activation markers at the surface of T cells was measured by flow cytometry. The results obtained are shown in FIGS. 35A-F, 37A-C and 36A-C respectively.

As already observed in Example 7, cells treated with anti-CD3 monoclonal antibodies combined with or without anti-CD28 monoclonal antibodies exhibited an increased secretion all measured cytokines except IL-5 and upregulation of surface expression of CD25 and CD69 activation markers. None of the tested aptamers was able to activate cytokine secretion of surface marker expression even when combined with costimulatory anti-CD28 antibody. Keeping aptamers concentrations constant by adding fresh solutions in a repeated manner to compensate for degradation in serum did not result in a more sustained activation profile.

Example 9: Functional Stability of Anti-CD3 DNA Aptamers

Stability of anti-CD3 DNA aptamers (CELTIC_1s, CELTIC_4s, CELTIC_9s, CELTIC_11s, CELTIC_19s and CELTIC_22 s) was measured in SELEX buffer containing 5% FBS or the FBS alone. Biotinylated aptamers were denatured at 95° C. for 5 min and then immediately cooled on ice block to 4° C. for 5 min. The sequences were then diluted to a final concentration of 2 μM in SELEX buffer supplemented with 5% of FBS or in pure FBS. Samples were incubated at 37° C. for 10 min, 30 min, 1 h, 2 h, 4 h or 24 h; the control samples contained the freshly prepared aptamers without incubation at 37° C. 100 nM streptavidin-PE was then added to each solution and aptamers were incubated with positives CD3 Jurkat cells as previously described. The half-life of aptamers in SELEX buffer containing 5% FBS or in pure FBS was then determined using flow cytometry on the YL-1 channel, based on the variation of the fluorescence-positives cells number as a function of the incubation time at 37° C. The results of the measurements are shown in FIGS. 11A and 11B. All the aptamers incubated in SELEX buffer containing 5% serum were stable, even when incubated for 24 h. Dilution of DNA aptamers in pure FBS shows gradual degradation of the sequences from 2 h of incubation at 37° C.

Example 10: Functional Stability of Anti-CD3 RNA Aptamers

Stability of aptamers ARACD3-3700006 and ARACD3-0010209 was measured in Dulbecco's phosphate-buffered saline (DPBS) containing 5 FBS or the FBS alone. The procedure described in Example 9 was used except that denaturation was carried out at 85° C. The results of the measurements are shown in FIG. 32-A. Both aptamers incubated in DPBS containing 5% serum were stable, even when incubated for 24 h. When incubated in pure serum half of the binding activity was lost after 30 min.

Example 11: Serum Stability of Anti-CD3 DNA Aptamers Using Gel Electrophoresis

Stability of anti-CD3 DNA aptamers (CELTIC_1s, CELTIC_4s, CELTIC_11s, CELTIC_19 s) was studied in selection (SELEX) buffer containing 5% fetal bovine serum (FBS), RPMI medium containing 10% FBS or pure FBS. Aptamers were denatured at 95° C. for 5 min and then immediately cooled on ice block to 4° C. for 5 min. The sequences were then diluted to a final concentration of 2 μM in SELEX buffer supplemented with 5% of FBS, RPMI medium supplemented with 10% FBS or in pure FBS serum. Samples were incubated at 37° C. for 10 min, 30 min, 1 h, 2 h, 4 h or 24 h; the control samples contained the freshly prepared aptamers without incubation at 37° C. Half-life of aptamers in their respective buffers was then determined by migration on agarose gel using electrophoresis method as follows: aptamer sample from different incubation times were mixed with loading buffer (ThermoScientific, Waltham, MA, USA) and 15 μL of each sample was placed on freshly prepared 3% agarose gel containing SYBRsafe (Invitrogen) as a DNA stain marker. The migration of DNA aptamers on agarose gel was performed in 1×TBE buffer (Invitrogen) by applying 100 V during 20 min. The gels were visualized using Bio-Rad imaging system and the results are shown in FIGS. 10A-10D. All tested aptamers were stable in SELEX-5% FBS buffer for at least 24 h. Incubation in RPMI medium containing 10% FBS caused degradation of CELTIC_4s and CELTIC_11s after 24 h at 37° C. However, dilution of DNA aptamers in pure serum resulted in a decrease of the intensity after 1 h of incubation. These results are in perfect agreement with stabilities reported with flow cytometry in Example 9.

Example 12: Serum Stability of Anti-CD3 RNA Aptamers Using Gel Electrophoresis

Stability of anti-CD3 RNA aptamers (ARACD3-3700006 and ARACD3-0010209) was studied in DPBS buffer containing 5% FBS, RPMI medium containing 10% FBS or pure FBS. Aptamers were denatured at 85° C. for 5 min and then immediately cooled on ice block to 4° C. for 5 min. The sequences were then diluted to a final concentration of 2 μM in DPBS buffer supplemented with 5% of FBS, RPMI medium supplemented with 10% FBS or in pure FBS serum. Samples were incubated at 37° C. for 10 min, 30 min, 1 h, 2 h, 4 h or 24 h; the control samples contained the freshly prepared aptamers without incubation at 37° C. Half-life of aptamers in their respective buffers was then determined by migration on agarose gel using denaturing electrophoresis method as follows: aptamer sample from different incubation times were mixed with formamide-containing loading buffer (ThermoScientific, Waltham, MA, USA) and after denaturation at 85° C. for 5 min, 15 μL of each sample was placed on freshly prepared 3% agarose gel containing SYBRsafe (Invitrogen) as a RNA stain marker. The migration of RNA aptamers on agarose gel was performed in 1×TBE buffer (Invitrogen) by applying 100 V during 20 min. The gels were visualized using Bio-Rad imaging system and the results are shown in FIGS. 32B-C. Both aptamers were stable in DPBS-5% FBS and RPMI-10% FBS for at least 4 h. Incubation of RNA aptamers in pure serum resulted in a decrease of the intensity after 30 min. These results are in perfect agreement with stabilities reported with flow cytometry in Example 10.

Example 13: Epitope Mapping of Anti-CD3 DNA Aptamers by Competition Binding Assay with Anti-CD3 Monoclonal Antibodies In order to gather more information on the region recognized by CELTIC_1s, CELTIC_4s, CELTIC_11s, CELTIC_19s aptamers, competition binding assays with reference monoclonal antibodies were performed on CD3-positive Jurkat cells essentially as already described in Example 3 but with the following changes.

Jurkat cells were incubated with PE-labelled monoclonal antibody (OKT3-PE—0.1 nM; UCHT1-PE-1 nM or HIT3a-PE—0.1 nM—all purchased from ThermoScientific, Waltham, MA, USA) for 30 min at 37° C. in presence of an excess of various competitors (unlabeled OKT3—32 nM; unlabeled UCHT1—10 nM; unlabeled HIT3a—32 nM—all purchased from ThermoScientific, Waltham, MA, USA and aptamers -300 nM). Binding of the labelled anti-CD3 monoclonal antibodies on cells was then evaluated by flow cytometry.

In a reverse experimental setting, Jurkat cells were incubated with CELTIC_1s, CELTIC_4s, CELTIC_11s, CELTIC_19s DNA aptamers (fixed concentration of 300 nM) with or without a saturating concentration of unlabeled monoclonal antibodies (OKT3—32 nM; UCHT1—10 nM; unlabeled HIT3a—32 nM). Binding of the biotinylated aptamers on cells was then evaluated by flow cytometry after detection with Streptavidin-PE.

Binding results of PE-labelled anti-CD3 monoclonal antibodies with or without saturating concentrations of competitors are shown in FIGS. 17.1.A, 17.2.A and 17.3.A. For each of tested antibodies, using an excess of its unlabeled form inhibited or completely abolished the binding of its PE-labeled version which validated the experimental conditions. Maximal signal was measured when aptamers were used as competitors suggesting that tested candidates failed to interfere with the binding of the three reference antibodies.

Binding results of anti-CD3 aptamers with or without saturating concentrations of monoclonal antibodies are shown in FIGS. 17.1.B, 17.2.B and 17.3.B. Similar signals were measured when aptamers were incubated with and without competitors suggesting that antibodies failed to interfere with the binding of tested sequences.

The lack of competition seen between anti-CD3 aptamers and the tested reference monoclonal antibodies suggests that the regions of human CD3 receptor targeted by aptamers differ from OKT3, HIT3a and UCHT1 epitopes. OKT3 and UCHT1 antibodies have been reported to activate T lymphocytes upon binding. The recognition of alternative CD3 epitopes by CELTIC_1s, CELTIC_4s, CELTIC_11s, CELTIC_19s is in line with the absence of activating properties observed on human PBMCs in Example 7.

Example 14: Epitope Mapping of Anti-CD3 RNA Aptamers by Competition Binding Assay with Anti-CD3 Monoclonal Antibodies In order to gather more information on the region recognized by ARACD3-3700006 and ARACD3-0010209 aptamers, competition binding assays with reference monoclonal antibodies were performed on CD3-positive Jurkat cells essentially as already described in Example 13 except that DPBS-5% FCS was used instead of SELEX buffer -5% FCS.

Binding results of PE-labelled anti-CD3 monoclonal antibodies with or without saturating concentrations of competitors are shown in FIGS. 38-A, 38-C and 38-E For each of tested antibodies, using an excess of its unlabeled form inhibited or completely abolished the binding of its PE-labeled version which validated the experimental conditions. Maximal signal was measured when aptamers were used as competitors suggesting that tested candidates failed to interfere with the binding of the three reference antibodies.

Binding results of anti-CD3 aptamers with or without saturating concentrations of monoclonal antibodies are shown in FIGS. 38.B, 38-D and 38-F. Similar signals were measured when aptamers were incubated with and without competitors suggesting that antibodies failed to interfere with the binding of tested sequences.

The lack of competition seen between anti-CD3 aptamers and the tested reference monoclonal antibodies suggests that the regions of human CD3 receptor targeted by aptamers differ from OKT3, HIT3a and UCHT1 epitopes. OKT3 and UCHT1 antibodies have been reported to activate T lymphocytes upon binding. The recognition of alternative CD3 epitopes by ARACD3-3700006 and ARACD3-0010209 is in line with the absence of activating properties observed on human PBMCs in Example 8.

Example 15: Engineering of Stability-Improved Anti-CD3 DNA Aptamers Derived from the Core Sequence Based on the results obtained in binding studies performed on CD3-positive and CD3-negative cells and described in Example 3, a short list of sequence-optimized anti-CD3 aptamers derived from the core sequence and with improved apparent affinity and target specificity was selected in order to further investigate their stability in serum. These analyses were carried out with aptamers CELTIC_core, CELTIC_core_12 and 5'-end HEG modified CELTIC_core_24, CELTICcore_29, CELTIC_core_40 and CELTIC_core_42 incubated in selection (SELEX) buffer containing 5% fetal bovine serum (FBS), RPMI medium containing 10% FBS or pure FBS. After various incubation times, fraction of undegraded aptamers was quantified by flow cytometry and agarose gel electrophoresis as previously described in Examples 11 and 13 respectively.

As shown in FIGS. 22 A-F and 23 A-C aptamers CELTIC_core, CELTIC_core_24 and CELTIC_core_29 appeared very unstable in each of the tested serum condition with no integral/functional aptamer left after 4 h incubation in SELEX-5% FBS or 30 min in pure serum. As already observed in Examples 11 and 13, there was a perfect consistency in results obtained by both methods. As a comparison, parental full-length CELTIC_1s and CELTIC_19 s sequences were stable 24 h in SELEX-5% FBS and at least 1 h in pure serum. On the other hand, CELTIC_core_12, CELTIC_core_40 and CELTIC_core_42 performed much better in both stability read-outs. CELTIC_core_12 was by far the most stable aptamer being totally undegraded after 24 h incubation in SELEX-5% FBS and RPMI medium containing 10% FBS. In pure serum, its degradation started to occur only after 4 h. CELTIC_core_40 and CELTIC_core_42 were intermediate cases being more stable that the unmodified CELTIC_core sequence but totally degraded in pure serum after 4 h incubation. It is noteworthy that although CELTIC_core_12, CELTIC_core_29 and CELTIC_core_42 only differ by one nucleotide at position 11 they exhibit totally different stability properties. Moreover, the introduction a second abasic site in CELTIC_core_29 at position 16 that resulted in CELTIC_core_42 appeared to be a strategy to stabilize the sequence.

As another attempt to improve the stability of HEG-modified CELTIC_core_40 and CELTIC_core_42, the benefit of adding a 3'-3' deoxy-thymidine was investigated. This type of modification at the 3'-end has been reported to enhance the resistance of nucleotidic sequences to nuclease degradation. As shown in FIGS. 32.1 A-D and 32.2 A-B and compared to CELTIC_core_40 and CELTIC_core_42, the aptamers with a 3'-3' deoxy-thymidine at the 3'-end had significantly improved stabilities. Although not outperforming CELTIC_core, these variants were stable 24 h in SELEX-5% FBS and at least 2 h in pure serum. It is worth mentioning that despite the presence of two abasic sites that are commonly believed to be nuclease-sensitive sites, CELTICcore42 was more stable than CELTIC_core_40.

Example 16: Most Stable and Sequence-Optimized Anti-CD3 Core DNA Sequence Derivatives Remain Cross-Specific Binding affinity measurements with the most interesting anti-CD3 aptamers derived from the core sequence were performed using a BIAcore T200 instrument (GE Healthcare) as already described in Example 4. To analyze interactions between aptamers and CD3 proteins, biotinylated aptamers were immobilized at a lower density than in Example 4 (100-500 RU) on Series S Sensor chips SA (GE Healthcare) according to manufacturer's instructions (GE Healthcare). Mouse and Cynomolgus CD3 ε/δ were purchased from AcroBiosystems. For human proteins, the highest concentration used was 100 nM and 1 μM for mouse and cynomolgus antigens. Other concentrations were obtained by 3-fold dilutions.

Table 8 below provides a summary of $K_D$ values obtained from surface plasmon resonance measurements. These results confirm the affinity drop observed in cell binding assays with the core sequence compared to parental sequences CELTIC_CD3_1s and CELTIC_CD3_19s. Variants of the core sequence identified in cell binding assays (CELTIC_core_12, CELTIC_core_24, CELTIC_core_29, CELTIC_core_40 and CELTIC_core_42) were all confirmed to have better affinities than the unmodified aptamer with human CD3 ε/γ. As already observed in Example 4, the affinities were in general slightly lower with CD3 ε/δ which is a consequence of the SELEX strategy that included more rounds on the CD3 ε/γ isoform. None of these sequences did bind to the Fc region of human IgG1. The addition of 3'-3' deoxy-thymidine at the 3'-end of CELTIC_core_24, CELTIC_core_40 and CELTIC_core_42 did not significantly change $K_D$ values.

TABLE 8

$K_D$ values determined by surface plasmon resonance for the sequence-optimized anti-CD3 core DNA sequence derivatives. From the recorded sensorgrams, data were computed with the kinetic analysis mode.

| Aptamer | Human CD3e/g | Human CD3e/d | Human Fc IgG |
|---|---|---|---|
| CELTIC_CD3_1s | 119 pM | 217 pM | NA |
| CELTIC_CD3_19s | 304 pM | 900 pM | NA |
| Core | 845 pM | 1000 pM | NA |
| Core12 | 1.15 pM | 1500 pM | NA |
| Core24 | 67 pM | 41 pM | NA |
| Core24t | 238 pM | 6 pM | NA |
| Core29 | 5.4 pM | 14 pM | NA |
| Core40 | 0.2 pM | 5.2 pM | NA |
| Core40t | 104 pM | 10 pM | NA |
| Core42 | 277 pM | 772 pM | NA |
| Core42t | 43 pM | 275 pM | NA |

Table 9 below provides a summary of $K_D$ values obtained from surface plasmon resonance measurements performed with human CD3 ε/γ and mouse and cynomolgus CD3 ε/δ. In this new experimental set-up, CELTIC_core showed again a lower affinity for human CD3 ε/γ compared to parental sequences CELTIC_core_1s and CELTIC_core_19s when sequence variants CELTICcore12, CELTIC_core_24, CELTIC_core_29, CELTIC_core_40 and CELTIC_core_42 showed improved affinities. In these conditions, 3'-3' deoxy-thymidine-modified versions of the latest four aptamers performed equally well. All these sequenced-optimized aptamers were able to bind the murine and cynomolgus CD3 ε/δ isoforms confirming the cross-specificity of the CD3 aptamers already observed in Examples 3 and 5. In contrast to CELTIC_core, CELTIC_1s or CELTIC_19s, $K_D$ values reported for interactions with mouse and cynomolgus CD3 ε/δ isoforms were in the same range as the human CD3 protein, suggesting that the interactions measured were real. Based on these results, anti-CD3 sequence-optimized aptamers remain cross-specific and bind to mouse, cynomolgus although these were selected against the human receptor.

TABLE 9

$K_D$ values determined by surface plasmon resonance for the sequence-optimized anti-CD3 core DNA sequence derivatives. From the recorded sensorgrams, data were computed with the steady-state analysis mode.

| Aptamer | Human CD3ε/γ | Mouse CD3ε/δ | Cynomolgus CD3ε/δ |
|---|---|---|---|
| CELTIC_CD3_1s | 156 nM | 937 nM | 2220 nM |
| CELTIC_CD3_19s | 99 nM | 437 nM | 889 nM |
| Core | 427 nM | 590686 nM | 1210 nM |
| Core12 | 98 nM | 455 nM | 717 nM |
| Core24 | 218 nM | 589 nM | 752 nM |
| Core24t | 233 nM | 601 nM | 883 nM |
| Core29 | 205 nM | 509 nM | 940 nM |
| Core40 | 129 nM | 552 nM | 1080 nM |
| Core40t | 156 nM | 498 nM | 1080 nM |
| Core42 | 194 nM | 412 nM | 692 nM |
| Core 42t | 176 nM | 341 nM | 572 nM |

Example 17: Most Stable and Sequence-Optimized Anti-CD3 Core DNA Sequence Derivatives Still Recognize Epitopes that are Different from Reference Antibodies In order to gather more information on the region recognized by CELTIC_core_12, CELTIC_core_40 t and CELTIC_42t aptamers, competition binding assays with reference monoclonal antibodies were performed on CD3-positive Jurkat cells essentially as already described in Example 13. As comparison, full length CD3_CELTIC_1s was included in these analyses.

Binding results of PE-labelled anti-CD3 OKT3, UCHT1 and HIT3a monoclonal antibodies with or without saturating concentrations of competitors are shown in FIGS. 21-A, 21-C and 21-E. For each oftested antibodies, using an excess of its unlabeled form inhibited or completely abolished the binding of its PE-labeled version which validated the experimental conditions. Maximal signal was measured when aptamers were used as competitors suggesting that tested candidates failed to interfere with the binding of the three reference antibodies.

Binding results of anti-CD3 aptamers with or without saturating concentrations of monoclonal antibodies are shown in FIGS. 21-B, 21-D and 21-E. Similar signals were measured when aptamers were incubated with and without competitors suggesting that antibodies failed to interfere with the binding of tested sequences.

The lack of competition seen between anti-CD3 aptamers and the tested reference monoclonal antibodies suggests that the regions of human CD3 receptor targeted by aptamers differ from OKT3, HIT3a and UCHT1 epitopes. Taken together these results suggest that sequence-optimized CELTIC_core_12, CELTIC_core_40 t and CELTIC_42t aptamers do not differ from parental sequences in terms of epitope specificity despite variations in nucleotide composition and chemical modifications of 5'- and 3'-ends. The binding to CD3 regions alternative to OKT3 and UCHT1 epitopes that are known to activate T lymphocytes upon binding suggests that CELTIC_core_12, CELTIC_core_40 t and CELTIC_42 t aptamers may not exhibit activating properties.

Example 18: Functionalization of Sequence-Optimized Anti-CD3 Core DNA Sequence Derivatives for Subsequent Grafting by Covalent Chemistry does not Modify Biological Properties We finally set out to evaluate the impact of modifications at 3' and 5'-termini on the biological properties of a given anti-CD3 aptamer. This issue is of particular relevance when considering covalent coupling of functionalized aptamers to a carrier, polymer or surface. To do so, we chose HEG-modified CELTIC_core_42 that we coupled with TEG-biotin via a at the 5'- or 3'-end or introduced at the 5'-end of CELTIC_core_42 a Tetrazine-PEG5 group by solid phase synthesis as already described in Example 1. Such functional groups respectively allow the coupling of aptamers to biotin via affinity interaction (the strongest interaction reported to date with $K_D$ in $10^{15}$ M) or covalent coupling to norbornene/alkene/alkyne-modified partners by click chemistry (Inverse Electron Demand Diels-Alder).

The interaction of these three versions of the same aptamer with CD3 receptor expressed on Jurkat cells was investigated as already described in Example 3. CD3-negative Ramos cells were included as negative control to monitor unspecific interactions mediated by the introduced chemical modifications. Results summarized in FIG. 33 show that both ends of a given aptamer can be modified with a biotin without any impact on the apparent affinity ($K_D$<50 nM) and specificity. The introduction of a tetrazine function at the 5'-end resulted in a slightly improved affinity (apparent $K_D$<25 nM) without any loss of specificity for the CD3 target.

Taken together these results suggest that functionalization of anti-CD3 aptamers for subsequent coupling can be carried out without significantly disturbing their biological properties.

TABLE 10

Summary of Sequences

| Aptamer | Sequence | Length | SEQ ID NO: |
|---|---|---|---|
| Cluster 1 | CCGGGTGGGGGTTTGGCACCGGGCCTGGCGCAGGGATTCG | 40 | 1 |
| Cluster 2 | GAGGGGTTTGGCATCGGGCCTGGCGCCATTCAAGCTATGC | 40 | 2 |
| Cluster 3 | GCGTAAGGGTTTGGCAGCGGGCCTGGCGGAACGCGTGTAT | 40 | 3 |
| Cluster 4 | GGAGTGGAGTATTCCGGGTTTGGCATCGGGCCTGGCGAAG | 40 | 4 |
| Cluster 5 | CGGCAGGGGTTTGGCTCCGGGTCTGGCGAACTGGCTGAGA | 40 | 5 |
| Cluster 6 | AAGGGATTGGCGTCGGGCCTGGCGTAAGGAGGCTATGCTC | 40 | 6 |
| Cluster 7 | GGGATTGGCGCTGGGCCTGGCAAGGAATCTTCTCGTTGTA | 40 | 7 |
| Cluster 8 | GGGATTGGCTTCGGGCCTGGCGAGTATTGTTTTCCTGGAG | 40 | 8 |
| Cluster 9 | GCATCGAAATGGGGTTGGCACCGGGCCTGGCGAATTGGAT | 40 | 9 |
| Cluster 10 | GAGACTAGAGGGATTGGCTTCGGGCCTGGCGTAC | 34 | 10 |
| Cluster 11 | GATGGAGGGTTTGGCGGTGGGCCTGGCAAGTTATCTCATA | 40 | 11 |
| Cluster 12 | TACGGCTAGGGTTTGGCGTTGGGCCTGGCAGGACCGTAAG | 40 | 12 |
| Cluster 13 | ATATGGGAGGGTGAGGGTTTGGCTGCGGGCCTGGCGGGAG | 40 | 13 |
| Cluster 14 | TGCGGCACATGTACGCGGAGGGATTGGCATAGGGTCTGGC | 40 | 14 |
| Cluster 15 | GGGGTTGGCTTTGGGCCTGGCAGTCATTTGTGAATCCTTA | 40 | 15 |

TABLE 10-continued

| Summary of Sequences | | | |
|---|---|---|---|
| Aptamer | Sequence | Length | SEQ ID NO: |
| Cluster 16 | TCCGACAAAAGGGATTGGCTTCGGGCCTGGCGGGGTTGCC | 40 | 16 |
| Cluster 17 | GGTCGGGGTTTGGCATCGGGACTGGCGTTATACAATCGT | 39 | 17 |
| Cluster 18 | GATGGGGTTTGGCGTCGGGCCTGGCGAATACATCTAAAAG | 40 | 18 |
| Cluster 19 | TACCGCGGGGATTGGCTCCGGGCCTGGCGTCGTAATCTGA | 40 | 19 |
| Cluster 20 | GGGGTTTGGCTGCGGGCCTGGCGCATGATTCAACGAGACA | 40 | 20 |
| Cluster 21 | GGTCGGGTGCTACTGAGCGATTGGCTTTCCGGACTGGGGA | 40 | 21 |
| Cluster 22 | CGACCACAGGGGTTTGGCTTCGGGACTGGCGGTGGGACT | 40 | 22 |
| Cluster 23 | CGACCACAGGGGTTTGGCTTCGGGACTGGCGGTGGGCACT | 40 | 23 |
| Cluster 24 | TATGGGTTTGGCATCGGGCCTGGCGGAATGGAAAATGTTA | 40 | 24 |
| Cluster 25 | AGACGGGTTTGGCTGCGGGCCTGGCGGTCGTCATTCCTCT | 40 | 25 |
| Cluster 26 | GAGGGGATTGGCATTTGGGCCTGGCAAATTCATCTATTCT | 40 | 26 |
| Cluster 27 | AGGGGTTTGGCGTCGGGCCTGGCGCAGCTCTTCTTGTGTTT | 41 | 27 |
| Cluster 28 | GGGATTGGCTTCGGGCCTGGCGTATCTTTTACATTACC | 38 | 28 |
| Cluster 29 | GGTGGACGGTATACAGGGGCTGCTCAGGATTGCGGATGAT | 40 | 29 |
| Cluster 30 | CCGTTTGAAGCGTTAGGGTTTGGCATCGGGCCTGGCGCAC | 40 | 30 |
| Cluster 31 | AGGGTTTGGCTACGGGCCTGGCGAGCTGTTTCCGCTACTC | 40 | 31 |
| Cluster 32 | GTGTTATGATACTATGCGTATGGATTGCAAAGGGCTGCTG | 40 | 32 |
| Cluster 33 | GAAGGGTTTGGCATTGGGCCTGGCAAGATAATTTGCAAGT | 40 | 33 |
| Cluster 34 | CGGCGAAGTGGCAGGGTTTGGCTTCGGGTCTGGCGGAACA | 40 | 34 |
| Cluster 35 | GAGGGTTTGGCAGTGGGCCTGGCATCAATTCTTTGTTTTC | 40 | 35 |
| Cluster 36 | TACTGAGGGTTTGGCATTGGGCCTGGCATATTGGTATTT | 39 | 36 |
| Cluster 37 | ATGGGTTTGGCACCGGGTCTGGCGGATTCGATAGGTGGTT | 40 | 37 |
| Cluster 38 | GGGGGTTTGGCTCTGGGCCTGGCATAACGAACCTTCGGAG | 40 | 38 |
| Cluster 39 | TGCCCGAGAGGACTGCTTAGGCTTGCGAGTAGGGAACGCT | 40 | 39 |
| Cluster 40 | AGTGGGATTGGCTTCGGGCCTGGCGTTCGCAACATGTTTA | 40 | 40 |
| Cluster 41 | GGGGATTGGCACTGGGACTGGCACCTTTTTAACATGTATG | 40 | 41 |
| Cluster 42 | GCAATTAAGGGATTGGCTCCGGGCCTGGCGCCACGCATGG | 40 | 42 |
| Cluster 43 | TGGGGTTTGGCAGCGGGTCTGGCGATCATAATGGTGTGCG | 40 | 43 |
| Cluster 44 | ACGGGGGATTGGCTTTGGGCCTGGCAATTAATTTACTGTT | 40 | 44 |
| Cluster 45 | GAGCGCTTGGCAGCCGGTCTGGGGACATCAGAGGTGATGG | 40 | 45 |
| CELTIC_1s | TTTCCGGGTGGGGGTTTGGCACCGGGCCTGGCGCAGGGATTCG | 43 | 46 |
| CELTIC_2s | GAGGGGTTTGGCATCGGGCCTGGCGCCATTCAAGCTATGC | 40 | 47 |
| CELTIC_3s | GCGTAAGGGTTTGGCAGCGGGCCTGGCGGAACGCGTGTAT | 40 | 48 |
| CELTIC_21s | GGTCGGGTGCTACTGAGCGATTGGCTTTCCGGACTGGGGA | 40 | 49 |
| CELTIC_4s | GGAGTGGAGTATTCCGGGTTTGGCATCGGGCCTGGCGAAG | 40 | 50 |
| CELTIC_5s | CGGCAGGGGTTTGGCTCCGGGTCTGGCGAACTGGCTGAGA | 40 | 51 |
| CELTIC_6s | AAGGGATTGGCGTCGGGCCTGGCGTAAGGAGGCTATGCTC | 40 | 52 |

TABLE 10-continued

Summary of Sequences

| Aptamer | Sequence | Length | SEQ ID NO: |
|---|---|---|---|
| CELTIC_9s | GCATCGAAATGGGGTTGGCACCGGGCCTGGCGAATTGGAT | 40 | 53 |
| CELTIC_11s | GATGGAGGGTTTGGCGGTGGGCCTGGCAAGTTATCTCATA | 40 | 54 |
| CELTIC_19s | TACCGCGGGGATTGGCTCCGGGCCTGGCGTCGTAATCTGA | 40 | 55 |
| CELTIC_22s | CGACCACAGGGGTTTGGCTTCGGGACTGGCGGTGGGCACT | 40 | 56 |
| CELTIC core | GGGXTTGGCXXXGGGXCTGGC | 21 | 57 |
| CELTIC core_1 | GGGTTTGGCACCGGGCCTGGCGC | 23 | 58 |
| CELTIC core_2 | GGGTTTGGCACCGGGCCTGGC | 21 | 59 |
| CELTIC core_3 | CCGGGCCTGGCC | 12 | 60 |
| CELTIC core_4 | GGGTTTGGCATCGGGCCTGGCG | 22 | 61 |
| CELTIC core_5 | GGGTTTGGCGGTGGGCCTGGC | 21 | 62 |
| CELTIC core_6 | TTTGGGTTTGGCACCGGGCCTGGC | 24 | 63 |
| CELTIC core_T | TTTGGGTTTGGCATCGGGCCTGGC | 24 | 64 |
| CELTIC core_7 | GGGTTT_GCACCGGGCCTGGC | 21 | 65 |
| CELTIC core_8 | GGGTTTG_CACCGGGCCTGGC | 21 | 66 |
| CELTIC core_9 | GGGTTTGG_ACCGGGCCTGGC | 21 | 67 |
| CELTIC core_10 | GGGTTTGGCACC_GGCCTGGC | 21 | 68 |
| CELTIC core_11 | GGGTTTGGCACCGG_CCTGGC | 21 | 69 |
| CELTIC core_12 | GGGTTTGGCACCGGG_CTGGC | 21 | 70 |
| CELTIC core_13 | GGGTTTGGCACCGGGC_TGGC | 21 | 71 |
| CELTIC core_14 | _GGTTTGGCATCGGGCCTGGC | 21 | 72 |
| CELTIC core 15 | G_GTTTGGCATCGGGCCTGGC | 21 | 73 |
| CELTIC core_16 | GG_TTTGGCATCGGGCCTGGC | 21 | 74 |
| CELTIC core_17 | GGG_TTGGCATCGGGCCTGGC | 21 | 75 |
| CELTIC core_18 | GGGT_TGGCATCGGGCCTGGC | 21 | 76 |
| CELTIC core_19 | GGGTT_GGCATCGGGCCTGGC | 21 | 77 |
| CELTIC core_20 | GGGTTT_GCATCGGGCCTGGC | 21 | 78 |
| CELTIC core_21 | GGGTTTG_CATCGGGCCTGGC | 21 | 79 |
| CELTIC core_22 | GGGTTTGG_ATCGGGCCTGGC | 21 | 80 |
| CELTIC core_23 | GGGTTTGGC_TCGGGCCTGGC | 21 | 81 |
| CELTIC core_24 | GGGTTTGGCA_CGGGCCTGGC | 21 | 82 |
| CELTIC core_25 | GGGTTTGGCAT_GGGCCTGGC | 21 | 83 |
| CELTIC core_26 | GGGTTTGGCATC_GGCCTGGC | 21 | 84 |
| CELTIC core_27 | GGGTTTGGCATCG_GCCTGGC | 21 | 85 |
| CELTIC core_28 | GGGTTTGGCATCGG_CCTGGC | 21 | 86 |
| CELTIC core_29 | GGGTTTGGCATCGGG_CTGGC | 21 | 87 |
| CELTIC core_30 | GGGTTTGGCATCGGGC_TGGC | 21 | 88 |
| CELTIC core_31 | GGGTTTGGCATCGGGCC_GGC | 21 | 89 |
| CELTIC core_32 | GGGTTTGGCATCGGGCCT_GC | 21 | 90 |

TABLE 10-continued

| Summary of Sequences | | | |
|---|---|---|---|
| Aptamer | Sequence | Length | SEQ ID NO: |
| CELTIC core_33 | GGGTTTGGCATCGGGCCTG_C | 21 | 91 |
| CELTIC core_34 | GGGTTTGGCATCGGGCCTGG_ | 21 | 92 |
| CELTIC core_35 | GGGTTTGGGATCGGGCCTGGC | 21 | 93 |
| CELTIC core_36 | GGGTTTGGCATCGGGCCTGGG | 21 | 94 |
| CELTIC core_37 | GGGTTTGGGATCGGGCCTGGG | 21 | 95 |
| CELTIC core_38 | GGGTTTGGCATCGGGACTGGC | 21 | 96 |
| CELTIC core_39 | GGGTTTGGCATCGGGGCTGGC | 21 | 97 |
| CELTIC core_40 | GGGTTTGGCATCGGGTCTGGC | 21 | 98 |
| CELTIC core_41 | GGGTTTGGCATCGGGCTGGC | 21 | 99 |
| CELTIC core_42 | GGGTTTGGCA_CGGG_CTGGC | 21 | 100 |
| CELTIC core_43 | GGGTTTGGCAGCGGGCTGGC | 21 | 101 |
| CELTIC core_44 | GGGTTTGGCAACGGGCTGGC | 21 | 102 |
| ARACD3-0010209 | UCUAAGCAAUAUUGUUUGCUUUUGCAGCGAUUCUGUUUCGAUAUAUUA | 48 | 103 |
| ARACD3-2980001 | UUCAAGAUAAUGUAAUUAUUUUUGCAGCGAUUCUUGUUUUGUUCGAUUU | 49 | 104 |
| ARACD3-0270039 | CAAAGUUCAAGAUUGAGCUUUUUGCAGCGAUUCUUGUUUUAUCAAACGA | 49 | 105 |
| ARACD3-3130001 | GAUGAUAUCUUUAAUAUCAAUUGCAGCGAUUCUUGUUUGAGAAUAAAC | 48 | 106 |
| ARACD3-3700006 | UAUAGACUUUAAUGUCUCAUUUUCGCAGCGAUUCUUGUUUAUUUAACAUA | 50 | 107 |
| Core sequence RNA | UXGCAGCGAUUCUXXUU | 17 | 108 |
| Consensus-1 | $GX_1X_2TX_3GX_4X_5X_6X_7X_8X_9GGX_{10}CTGG$, wherein $X_1$ is G or A; $X_2$ and $X_6$ are A, T, or G; $X_3$ is T, or G; $X_4$ and $X_9$ are G or C; $X_5$ is C or T; $X_7$ is T, G, or C; and $X_8$ and $X_{10}$ are C, T, or A. | | 109 |
| Consensus-2 | $GGGX_1TTGGCX_2X_3X_4GGGX_5CTGGC$, wherein $X_1$ and $X_2$ are A, T, or G; $X_3$ is T, C, or G; $X_4$ and $X_5$ are A, T, or C. | | 110 |
| Consensus-3 | $GX_1TTX_2GX_3X_4X_5X_6CX_7GGX_8CTGGX_9G$, wherein $X_1$ is A or G; $X_2$ is T or G; $X_3$ and $X_7$, $X_9$ are G or C; $X_4$ is T or C; $X_5$ is A or T; $X_6$ is T, C, or G; $X_8$ is A or C. | | 111 |
| Consensus-4 | $GGGTTTGGCAX_1CGGGCCTGGC$, wherein $X_1$ is G, C, or T. | | 112 |
| Consensus-5 | $GCAGCGAUUCUX_1GUUU$, wherein $X_1$ is U or nothing | | 113 |
| DNA aptamer library | TAGGGAAGAGAAGGACATATGAT-(N40)-TTGACTAGTACATGACCACTTGA | | 114 |
| forward primer for DNA SELEX | TAGGGAAGAGAAGGACATATGAT | | 115 |
| reverse primer for DNA SELEX | TCAAGTGGTCATGTACTAGTCAA | | 116 |
| RNA aptamer library | CCTCTCTATGGGCAGTCGGTGAT-(N20)-TTTCTGCAGCGATTCTTGTTT-(N10)-GGAGAATGAGGAACCCAGTGCAG | | 117 |
| forward primer for RNA SELEX | TAATACGACTCACTATAGGGCCTCTCTATGGGCAGTCGGTGAT | | 118 |

TABLE 10-continued

Summary of Sequences

| Aptamer | Sequence | Length | SEQ ID NO: |
|---|---|---|---|
| reverse primer for RNA SELEX | CTGCACTGGGTTCCTCATTCTCC | | 119 |
| forward blocking sequence for RNA SELEX | ATCACCGACTGCCCATAGAGAGG | | 120 |
| reverse blocking sequence for RNA SELEX | CTGCACTGGGTTCCTCATTCTCC | | 121 |
| capture sequence for RNA SELEX | CAAGAATCGCTGCAG | | 122 |

For clusters 1 to 45, flanking regions present at the 5'- and 3'-ends (TAGGGAAGAGAAGGACATATGAT and TTGACTAGTACATGACCACTTGA respectively) and described in SEQ ID NO 114 are present but not shown.

As used herein, “consisting essentially of” allows the inclusion of materials or steps that do not materially affect the basic and novel characteristics of the claim. Any recitation herein of the term “comprising”, particularly in a description of components of a composition or in a description of elements of a device, can be exchanged with “consisting essentially of” or “consisting of”.

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A vehicle for delivering an agent, a dye, a functional group for covalent coupling or a biologically active agent to T cells, wherein the vehicle comprises (i) an aptamer comprising the sequence $GX_1TTX_2GX_3X_4X_5X_6CX_7GGX_8CTGGX_9G$, wherein $X_1$ is A or G; $X_2$ is T or G; $X_3$ and $X_7$, $X_9$ are G or C; $X_4$ is T or C; $X_5$ is A or T; $X_6$ is T, C, or G; $X_8$ is A or C (SEQ ID NO:111) or a variant thereof having one or more of said bases substituted with a non-naturally occurring base or one or more of said bases omitted and wherein the aptamer binds to CD3 ε/γ or CD3 ε/δ, and (ii) said agent, dye, functional group for covalent coupling, or biologically active agent.

2. The vehicle of claim 1 that comprises a polymeric nanoparticle.

3. The vehicle of claim 2, wherein the polymeric nanoparticle comprises a poly(beta amino ester) (PBAE).

4. The vehicle of claim 2, wherein the aptamer is covalently linked to the polymer.

5. The vehicle of claim 2, wherein the agent is a T cell modulator or an imaging agent.

6. The vehicle of claim 5, wherein the T cell modulator is a viral vector carrying a transgene; wherein the viral vector is coated with the polymer; and wherein the aptamer is covalently linked to the polymer.

7. The vehicle of claim 6, wherein the viral vector is a lentiviral vector.

8. The vehicle of claim 6, wherein the transgene encodes a chimeric antigen receptor.

9. The vehicle of claim 5, wherein the T cell modulator is selected from the group consisting of dasatinib, an MEK1/2 inhibitor, a PI3K inhibitor, an HDAC inhibitor, a kinase inhibitor, a metabolic inhibitor, a GSK3 beta inhibitor, an MAO-B inhibitor, and a Cdk5 inhibitor.

10. A method of delivering an agent to T cells in a subject, the method comprising administering the vehicle of claim 5 to the subject.

11. A pharmaceutical composition comprising the vehicle of claim 5 and one or more excipients.

12. A method of isolating T cells from a subject, the method comprising using an aptamer to isolate T cells from the subject, wherein the aptamer comprises the sequence $GX_1TTX_2GX_3X_4X_5X_6CX_7GGX_8CTGGX_9G$, wherein $X_1$ is A or G; $X_2$ is T or G; $X_3$ and $X_7$, $X_9$ are G or C; $X_4$ is T or C; $X_5$ is A or T; $X_6$ is T, C, or G; $X_8$ is A or C (SEQ ID NO: 111) or a variant thereof having one or more of said bases substituted with a non-naturally occurring base or one or more of said bases omitted or the corresponding nucleotide replaced with a linker, and wherein the aptamer binds to CD3 ε/γ or CD3 ε/δ.

13. The vehicle of claim 1, wherein the aptamer binds to but does not activate CD3+ T cells.

14. The vehicle of claim 1, wherein the aptamer binds to human CD3 ε/γ and/or CD3 ε/δ with a dissociation constant of about 0.2 pM to about 250 nM.

15. The vehicle of claim 1, wherein the aptamer binds to a non-human form of CD3 ε/γ and/or CD3 ε/δ with a dissociation constant of about 20 nM to about 800 nM.

16. The vehicle of claim 1, wherein the one or more non-naturally occurring bases are selected from the group consisting of methylinosine, dihydrouridine, methyl guanosine, and thiouridine.

* * * * *